(12) United States Patent
Kohane et al.

(10) Patent No.: US 12,427,196 B2
(45) Date of Patent: Sep. 30, 2025

(54) MACROMOLECULAR PRODRUGS FOR LIGHT-EMITTING DIODES AND USES THEREOF

(71) Applicant: Children's Medical Center Corporation, Boston, MA (US)

(72) Inventors: Daniel S. Kohane, Newton, MA (US); Wei Zhang, Nashua, NH (US)

(73) Assignee: Children's Medical Center Corporation, Boston, MA (US)

( * ) Notice: Subject to any disclaimer, the term of this patent is extended or adjusted under 35 U.S.C. 154(b) by 239 days.

(21) Appl. No.: 17/793,276

(22) PCT Filed: Jan. 15, 2021

(86) PCT No.: PCT/US2021/013628
§ 371 (c)(1),
(2) Date: Jul. 15, 2022

(87) PCT Pub. No.: WO2021/146553
PCT Pub. Date: Jul. 22, 2021

(65) Prior Publication Data
US 2023/0346942 A1 Nov. 2, 2023

Related U.S. Application Data
(60) Provisional application No. 62/962,769, filed on Jan. 17, 2020.

(51) Int. Cl.
*A61K 41/00* (2020.01)
*A61K 47/60* (2017.01)
(Continued)

(52) U.S. Cl.
CPC .......... *A61K 41/0042* (2013.01); *A61K 47/60* (2017.08); *A61K 47/6929* (2017.08);
(Continued)

(58) Field of Classification Search
None
See application file for complete search history.

(56) References Cited

U.S. PATENT DOCUMENTS 4,684,728 A * 8/1987 Mohring ................ A01N 47/36
549/417

FOREIGN PATENT DOCUMENTS

WO WO-2014004278 A1 * 1/2014 ............. A61K 38/28
WO WO-2019109065 A1 * 6/2019 ........... A61K 31/519

OTHER PUBLICATIONS

Gao et al., Photo-controlled release of fipronil from a coumarin triggered precursor. Bioorg Med Chem Lett. Jun. 1, 2017;27(11):2528-35. doi: 10.1016/j.bmcl.2017.03.091. Epub Apr. 1, 2017.
Zhan et al., Ultrasensitive Phototriggered Local Anesthesia. Nano Lett. Feb. 8, 2017;17(2):660-65. doi: 10.1021/acs.nanolett.6b03588. Epub Jan. 6, 2017.

(Continued)

*Primary Examiner* — Karl J Puttlitz
(74) *Attorney, Agent, or Firm* — Wolf, Greenfield & Sacks, P.C.

(57) ABSTRACT

Provided herein are compositions comprising macromolecular photocleavable prodrug compounds of Formula (I), and pharmaceutically acceptable salts, co-crystals, tautomers, stereoisomers, solvates, hydrates, polymorphs, and isotopically enriched derivatives thereof. Also provided are methods, uses, pharmaceutical compositions, and kits involving the inventive compounds or compositions for treating and/or preventing a disease and/or condition (e.g., inflammatory disease, infectious disease, pain) in a subject, optionally comprising illumination of the compound, composition, or pharmaceutical composition with light of an absorption wavelength sufficient to cleave the bonds between each instance of L and each instance of X upon illumination with the light (e.g., light between approximately 200 nm to 500 nm).

16 Claims, 23 Drawing Sheets

(51) Int. Cl.
  *A61K 47/69*    (2017.01)
  *A61P 23/02*    (2006.01)
  A61K 31/166    (2006.01)
  A61K 31/167    (2006.01)
  A61K 31/245    (2006.01)
  A61K 31/445    (2006.01)
(52) U.S. Cl.
  CPC ............ *A61P 23/02* (2018.01); *A61K 31/166* (2013.01); *A61K 31/167* (2013.01); *A61K 31/245* (2013.01); *A61K 31/445* (2013.01)

(56) References Cited

OTHER PUBLICATIONS

Chen et al., Injectable microparticle-gel system for prolonged and localized lidocaine release. II. In vivo anesthetic effects. J Biomed Mater Res A. Sep. 1, 2004;70(3):459-66. doi: 10.1002/jbm.a.30101.
Rwei et al., Photoresponsive nanoparticles for drug delivery. Nano Today. Aug. 1, 2015;10(4):451-467. doi: 10.1016/j.nantod.2015.06.004. Epub Jul. 15, 2015. Author Manuscript, 37 pages.
Zhan et al., Phototriggered Local Anesthesia. Nano Lett. Jan. 13, 2016;16(1):177-81. doi: 10.1021/acs.nanolett.5b03440. Epub Dec. 14, 2015.
Zhang et al., Light-triggered release of conventional local anesthetics from a macromolecular prodrug for on-demand local anesthesia. Nat Commun. May 8, 2020;11(1):2323. doi: 10.1038/s41467-020-16177-w.

\* cited by examiner

MACROMOLECULAR PRODRUGS FOR LIGHT-EMITTING DIODES AND USES THEREOF

This application claims priority under 35 U.S.C. § 119(e) to U.S. Provisional Application, U.S. Ser. No. 62/962,769, filed Jan. 17, 2020, which is incorporated herein by reference.

FEDERALLY SPONSORED RESEARCH

This invention was made with government support under Grant Number GM131728, awarded by the National Institutes of Health. The Government has certain rights in the invention.

RELATED APPLICATIONS

This application is a national stage filing under 35 U.S.C. § 371 of International Application No. PCT/US2021/013628, filed Jan. 15, 2021, which claims priority under 35 U.S.C. § 119 (e) to U.S. Provisional Application, U.S. Ser. No. 62/962,769, filed Jan. 17, 2020, the entire contents of each of which are incorporated herein by reference.

BACKGROUND OF THE INVENTION

Localized pain can be treated by systemic or local medications. The former often include opioids, which have many associated problems and side effects, including nausea, itching, constipation, tolerance, addiction, death by overdose, and the potential for diversion. Local treatments commonly involve local anesthetics. These are very effective but are of relatively brief duration. Moreover, their initial administration is painful (if done in awake patients), and requires skilled personnel in a medical facility. Consequently, there has been interest, for many decades, in developing sustained release systems that would provide prolonged duration local anesthesia.[1-3] However, those systems released drug in a relatively monotonic manner, and did not have a mechanism by which the drug release—and the resulting local anesthesia—could be modulated in real time in response to changing patient needs.

To achieve a local anesthetic release system which could be easily adjusted by patients could be of benefit, other drug delivery systems have been employed that are responsive to external stimuli, in which a therapeutic effect can be achieved at a desired dosage, time and location, ideally repeatedly.[4-6] A variety of "triggers" have been used in the literature, such as light,[7-10] ultrasound[11,12] and magnetic fields[13,14]. Among them, light is a promising trigger because of its tunable wavelength, irradiance, and area and duration of exposure.[15] Liposomal systems have been developed in which local anesthesia was achieved by irradiation of liposomal carriers, such that the time of onset, intensity, and duration of local anesthesia could be determine by the timing, intensity, and duration of irradiation.[16-18] These systems suffered from a problem common to most particulate drug delivery systems: release occurring from the moment of the devices' creation until drug is depleted. Early on, this results in untriggered rapid drug release; in the context of local anesthesia, this may result in extended initial nerve block, which may be undesirable. Subsequently, ongoing release may result in depletion of drug even if the system is not triggered (i.e. basal release), so that it is no longer available for triggered release.

It is important to develop a local anesthetic release system reducing the unwanted initial nerve blockage and basal drug release, in which the timing of the anesthetic release and the intensity of the anesthetic could be easily modulated, based on the needs of the subject.

SUMMARY OF THE INVENTION

Described herein are compositions comprising a compound of Formula (I):

or a pharmaceutically acceptable salt, co-crystal, tautomer, stereoisomer, solvate, hydrate, polymorph, or an isotopically enriched derivative thereof, wherein:
n is an integer of 1 or more;
each instance of X is independently an anesthetic compound;
each instance of L is independently a photocleavable linker; and
P is a polymer.

In some embodiments, the compound of Formula (I) is of Formula (I-A):

or a pharmaceutically acceptable salt, co-crystal, tautomer, stereoisomer, solvate, hydrate, polymorph, or an isotopically enriched derivative thereof. In some embodiments, the compound of Formula (I) is of Formula (I-A): X-L-P-L-X (I-A), or a pharmaceutically acceptable salt thereof. In certain embodiments, the bonds between each instance of photocleavable linker L and each instance of X are cleaved upon illumination with light at an absorption wavelength between approximately 200 nm to 500 nm. In certain embodiments, the composition forms a gel at temperatures above a phase transition temperature; and the phase transition temperature is about 37° C. In certain embodiments, X is a local anesthetic compound, for example, but not limited to, an amino ester compound (e.g., procaine, tetracaine, chloroprocaine, benzocaine, butacaine, dimethocaine) or an amino amide compound (e.g., procainamide, lidocaine). In certain embodiments, the compound described herein and composition thereof are stable for an extended period of time, for example, but not limited to, one week, two weeks, or three weeks. In certain embodiments, the compound described herein and composition thereof are stable for an extended period of time (e.g., one week, two weeks, or three weeks) in the dark. In certain embodiments, n is 1, 2, 3, 4, 5, 6, 7, 8, 9, or 10. In certain embodiments, P is a hydrophilic or amphiphilic polymer.

In some embodiments, the compound is of Formula (I-A):

or a pharmaceutically acceptable salt, co-crystal, tautomer, stereoisomer, solvate, hydrate, polymorph, or an isotopically enriched derivative thereof,
each instance of X is independently a local anesthetic compound;
each instance of L is independently a photocleavable linker; and
P is a hydrophilic or amphiphilic polymer.

In some embodiments, the compound is of the formula:

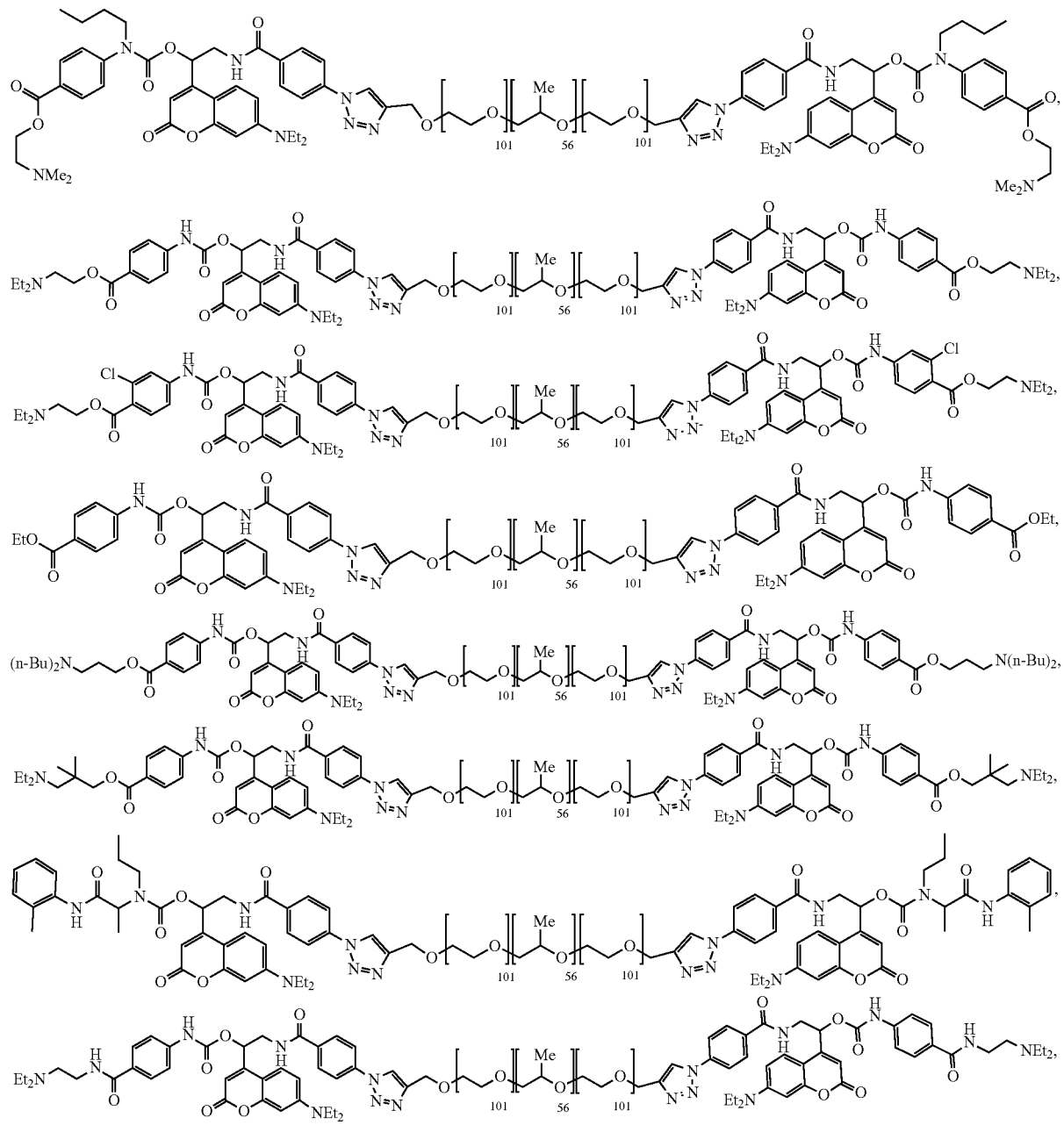

or a pharmaceutically acceptable salt, co-crystal, tautomer, stereoisomer, solvate, hydrate, polymorph, or an isotopically enriched derivative thereof.

Some aspects of the present disclosure provide pharmaceutical compositions comprising a composition of a compound described herein, for treating a disease or condition (e.g., inflammatory disease, infectious disease, pain) in a subject in need thereof.

Other aspects of the disclosure provide methods of treating a disease or condition (e.g., inflammatory disease, infectious disease, pain) in a subject in need thereof comprising administering to the subject a therapeutically effective amount of a composition of a compound described herein, optionally further comprising illumination of the composition or the pharmaceutical composition with light at an absorption wavelength between approximately 200 nm to 500 nm (e.g., with a LED (e.g., blue LED)).

Other aspects of the disclosure provide uses of the compounds, compositions, or pharmaceutical compositions thereof described herein, for treating a disease or condition (e.g., inflammatory disease, infectious disease, pain) in a subject in need thereof, optionally further comprising illumination of the composition or the pharmaceutical composition with light at an absorption wavelength between approximately 200 nm to 500 nm (e.g., with a LED (e.g., blue LED)). Also provided are kits comprising a container with the compounds, compositions, and pharmaceutical compositions described herein, optionally further comprising a light of an absorption wavelength between approximately 200 nm to 500 nm (e.g., with a LED (e.g., blue LED)). The kits described herein may include a single unit or multiple units of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

This disclosure is based in part on the discovery of an on-demand anesthetic that would take effect when needed and where the intensity of anesthesia could be easily adjustable according to patients' needs. Here, a macromolecular prodrug (P407-CM-T) was designed and synthesized in which the local anesthetic tetracaine was attached to the polymer poloxamer 407 (P407) via a photocleavable coumarin linkage. P407-CM-T solution was injectable at low temperature and gelled near body temperature. The macromolecular prodrug showed no anesthetic effect itself unless irradiated with a light emitting diode (LED), for example, a low-power blue LED, resulting in local anesthesia. By adjusting the intensity and duration of irradiation, the anesthetic effect could be modulated. Local anesthesia could be repeatedly triggered. To eliminate the unwanted initial nerve blockage and basal drug release, the drug is conjugated onto macromolecular carriers in a manner that could be reversed by photo-triggering.

A light triggerable polymer-drug conjugate has been designed, which is composed of at least exemplary three parts: a conventional local anesthetic, a polymer carrier, and a photocleavable linkage in between them (See FIG. 1a). Conventional local anesthetics usually consist of a hydrophobic aromatic ring, an intermediate linkage (ester or amide) and a tertiary amine. Some of them, have a primary amine (such as in procaine and chloroprocaine) or secondary amine (such as in tetracaine) substituent group on the aromatic ring, which could be used in chemical reactions. Tetracaine is an exemplary local anesthetic employed due to its relatively high potency in its class.[19] Poloxamer 407 (P407), which is a Food and Drug Administration (FDA) approved polymer, was used as the exemplary polymeric carrier. Apart from acting as the macromolecular component of the prodrug, it has the desirable property of reverse thermal gelation, i.e. a solution of P407 is liquid at low (e.g. room) temperature during injection and gels in the body due to the higher temperature.[20] This gelation encourages persistence of the polymer at the site of injection. 7-(diethylamino) coumarin (DEACM) was selected as the photo-responsive moiety due to its good photocleavage efficiency, relatively long absorption wavelength (near 400 nm, blue light, low phototoxicity) as well as good stability in darkness, which may be beneficial for shelf-life.[15, 21]

It is hypothesized that this system would enable light-triggerable nerve block over an extended period, with minimal untriggered drug release. Consequently, there would be no initial nerve block and no wastage of drug between triggered events. By tuning the intensity and duration of irradiation, the amount of drug released could be adjusted on-demand, allowing modulation of the anesthetic effect. A light emitting diode (LED) was used as the light source, because compared with laser sources, LED's are cheaper and easier to use. Moreover, the lower energies involved suggest a lower risk of thermal injury.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, Stereochemistry of Carbon Compounds (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example, "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^AH(C^BH_2C^CH_3)$— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

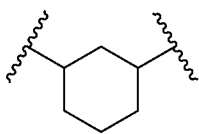 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C—C—CH≡CH— are all examples of a unsubstituted and unsaturated hydrocarbon chain. In certain embodiments, the hydrocarbon chain is unsubstituted (e.g., —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

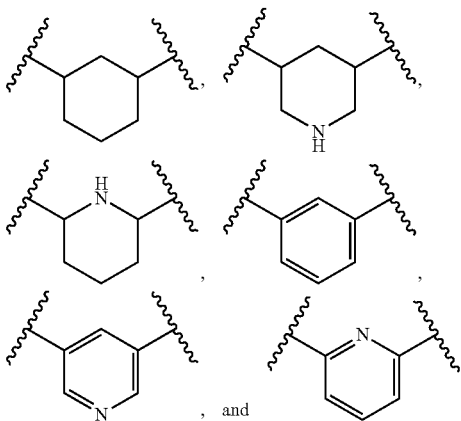

are all examples of a hydrocarbon chain. In contrast, in certain embodiments

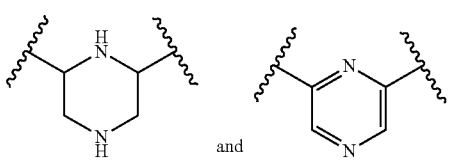 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —CH$_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-9}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{3-10}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from the group consisting of nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from the group consisting of nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from the group consisting of nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from the group consisting of nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from the group consisting of nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation but is not intended to include aromatic groups (e.g., aryl or heteroaryl groups) as defined herein. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R—, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rad groups; wherein X$^-$ is a counterion;

or two geminal hydrogens on a carbon atom are replaced with the group =O, =S, =NN(R$^{bb}$)$_2$, =NNR$^{bb}$C(=O)R—, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of $R^{dd}$ is, independently, selected from halogen, —CN, —NO$_2$, —N$_3$, —SO$_2$H, —SO$_3$H, —OH, —OR$^{ff}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{aa}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$— or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di- alkylamino, mono- or di- heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$$^+$X$^-$, —P(O$R^{cc}$)$_2$, —P(O$R^{cc}$)$_3$$^+$X$^-$, —P(=O)($R^{aa}$)$_2$, —P(=O)(O$R^{cc}$)$_2$, and —P(=O)(N($R^{bb}$)$_2$)$_2$, wherein X$^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —N($R^{bb}$)$_2$, —C(=O)S$R^{aa}$, —C(=O)R—, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P(R)$_3$$^+$X$^-$, —P(OR$^{cc}$)$_2$, —P(OR)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in a heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{aa}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, amines, ammonia, alcohols, ether moieties, sulfur-containing moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$$^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2H$_2$O) and hexahydrates (R·6H$_2$O)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, which have cleavable groups and become pharmaceutically active in vivo, for example, under illumination by light. Such examples include, but are not limited to, ester derivatives and the like. Other prodrugs often offer advantages of solubility, tissue compatibility, or delayed release in the mammalian organism (see, Bundgard, H., *Design of Prodrugs*, pp. 7-9, 21-24, Elsevier, Amsterdam 1985).

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal. A "patient" refers to a human subject in need of treatment of a disease.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. In certain embodiments, an effective amount is an amount of the prodrug compound sufficient to elicit the desired biological response, upon cleavage of the photocleavable linker between the compound X and the polymer P. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses. When an effective amount of a composition is referred herein, it means the amount is prophylactically and/or therapeutically effective, depending on the subject and/or the disease to be treated. Determining the effective amount or dosage is within the abilities of one skilled in the art.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. In certain embodiments, a therapeutically effective amount is an amount of the prodrug compound, alone or in combination with other therapies, which provides a therapeutic benefit in the treatment of the condition, upon cleavage of the photocleavable linker between the compound X and the polymer P. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount of the prodrug compound sufficient to elicit the desired biological response, upon cleavage of the photocleavable linker between the compound X and the polymer P.

A "prophylactically effective amount" of a compound described herein is an amount effective to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. In certain embodiments, a prophylactically effective amount of the prodrug compound means an amount of a prodrug compound, alone or in combination with other therapeutic agents, which provides a prophylactic benefit in the prevention of the condition, upon cleavage of the photocleavable linker between the compound X and the polymer P. The term "prophylactically effective amount" can encompass an amount that improves overall prophylaxis or enhances the prophylactic efficacy of another prophylactic agent.

As used herein, the term "infectious disease" refers to an illness caused by a pathogenic biological agent that results from transmission from an infected person, animal, or reservoir to a susceptible host, either directly or indirectly, through an intermediate plant or animal host, vector, or inanimate environment. See Last J M. ed. A dictionary of epidemiology. 4th ed., New York: Oxford University Press, 1988. Infectious disease is also known as transmissible disease or communicable disease. In certain embodiments, infectious diseases may be asymptomatic for much or even all of their course in a given host. Infectious pathogens include some viruses, bacteria, fungi, protozoa, multicellular parasites, and aberrant proteins known as prions.

A "painful condition" or "pain" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like.

One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition. In certain embodiments, the painful condition is neuropathic pain. The term "neuropathic pain" refers to pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years, even after the original injury has healed. Neuronal injury may occur in the peripheral nerves, dorsal roots, spinal cord or certain regions in the brain. Neuropathic pain conditions include, but are not limited to, diabetic neuropathy (e.g., peripheral diabetic neuropathy); sciatica; non-specific lower back pain; multiple sclerosis pain; carpal tunnel syndrome, fibromyalgia; HIV-related neuropathy; neuralgia (e.g., post-herpetic neuralgia, trigeminal neuralgia); pain resulting from physical trauma (e.g., amputation; surgery, invasive medical procedures, toxins, burns, infection), pain resulting from cancer or chemotherapy (e.g., chemotherapy-induced pain such as chemotherapy-induced peripheral neuropathy), and pain resulting from an inflammatory condition (e.g., a chronic inflammatory condition). Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia). In certain embodiments, the painful condition is non-inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric subjects (e.g., pain where no physical cause may exist), and wandering pain (e.g., wherein the pain repeatedly changes location in the body).

In certain embodiments, the painful condition is inflammatory pain. In certain embodiments, the painful condition (e.g., inflammatory pain) is associated with an inflammatory condition and/or an immune disorder. In certain embodiments, the pain is chronic pain related to one or more of the following conditions, including, but not limited to, lower back pain, arthritis (e.g., osteoarthritis), headaches, multiple sclerosis, fibromyalgia, shingles, cancer, surgery, or other medical procedures, amputation; surgery, invasive medical procedures, toxins, burns, infection, and nerve damage (e.g., neuropathy). In certain embodiments, the pain is pain associated with psychological factors, which is psychogenic pain related to one or more of the following conditions including headaches, muscle pains, back pains, or stomach pains.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

A "chronic disease" refers to a disease lasting for three or more months. Exemplary chronic diseases include, but are not limited to, arthritis, cardiovascular disease such as heart disease, stroke, cancer (e.g., breast cancer or colon cancer), chronic respiratory diseases, diabetes, epilepsy, seizures, obesity, and oral health problems.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows the synthesis of P407-CM-T through alkyne-azide "click" reaction. FIG. 1B shows the photocleavage reaction of P407-CM-T. FIG. 1C shows the $^1$H NMR of P407-CM-T.

FIG. 2A shows the UV-vis absorption spectra of aqueous solutions of P-CM-T (0.3 mg/mL), tetracaine hydrochloride (0.01 mg/mL) and $NH_2$—CM-OH (0.01 mg/mL). FIG. 2B shows the rheology of 20 wt % P-CM-T as a function of temperature.

FIG. 3A shows the liquid chromatography curve of tetracaine, P407-CM-T before and after cleavage under 400 nm LED irradiation. FIG. 3B shows the mass spectrum corresponding to the peak at 5 min in the curve of P407-CM-T+light in panel a. FIG. 3C shows the photocleavage of P407-CM-T solution (10 mg/mL) over time under 400 nm LED at different irradiances.

FIGS. 4A-4B show the cell survival (determined by MTS cell proliferation assay) of C2C12 and PC12 cells in direct contact with various concentrations of tetracaine, P407 and P407-CM-T for 24 h. FIGS. 4C-4D show the cell survival (determined by MTS cell proliferation assay) of C2C12 and PC12 cells exposed to tetracaine (0.5% wt %), P407 (20% wt %) and P407-CM-T (20% wt %) in Transwells® for 24 h.* indicates p<0.05 compared to untreated cells.

FIG. 5A shows the time courses of nerve block after injection of tetracaine, CM-T (tetracaine bound to coumarin without P407) and P407-CM-T with or without 2 min irradiation (as depicted in the graph) at 300 mW/cm$^2$, immediately after injection. FIG. 5B shows the nerve block after irradiation of P407-CM-T with irradiation at various irradiances and durations. (The 300 mW/cm$^2$, 2 min plot is also in FIG. 5A) FIG. 5C shows the effect of energy density on the duration of the triggered nerve block. FIG. 5D shows the representative time course of nerve block with multiple light triggering events (arrows represent LED triggering for 2 min at 300 mW/cm$^2$). FIG. 5E shows the mean duration of block after each triggering event in FIG. 5D. Data are means±SD (n≥4).

DETAILED DESCRIPTION OF CERTAIN EMBODIMENTS

Figure 1A:
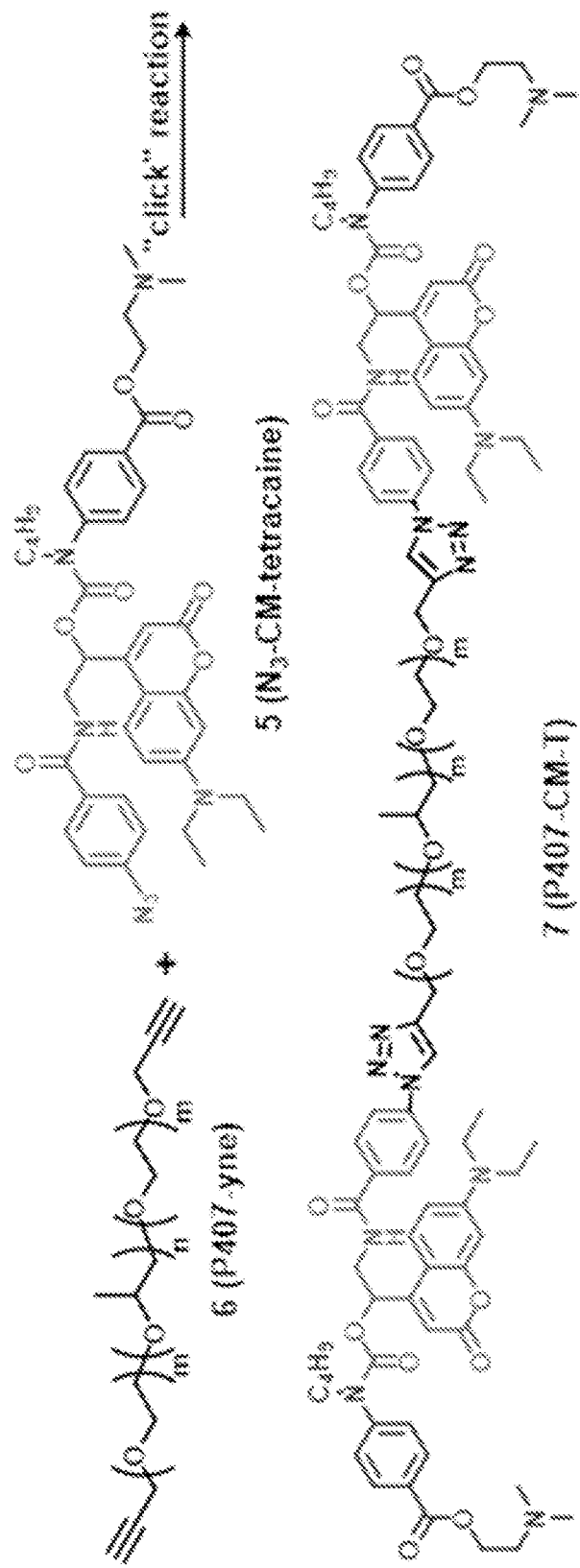
FIGS. 1A-1C show the synthesis and characterization of the light-triggerable tetracaine-polymer prodrug.

The present disclosure provides compositions comprising macromolecular prodrug compounds with photocleavable linkers that may be cleaved to release an anesthetic compound X (e.g., local anesthetic), upon illumination with light, for example, light at an absorption wavelength between approximately 200 nm to 500 nm (e.g., a LED (e.g., a blue LED)). In certain embodiments, the composition forms a gel at temperatures above a phase transition temperature; and the phase transition temperature is about 37° C. In certain embodiments, the composition comprises an anesthetic compound X that is a local anesthetic compound, for example, but not limited to, an amino ester compound (e.g., procaine, tetracaine, chloroprocaine, benzocaine, butacaine, dimethocaine) or an amino amide compound (e.g., procainamide, lidocaine). The composition comprises a polymer P (e.g., hydrophilic or amphiphilic polymer), which in certain embodiments, is a block copolymer comprising at least one polyether, for example, a poloxamer (e.g., poloxamer P407). In certain embodiments, P is a hydrophobic polymer. The composition comprises a photocleavable linker connecting the polymer P and anesthetic compound X, which in certain embodiments, coumarin, o-nitrobenzyl, benzoin, 7-nitroindoline, or p-hydroxyphenacyl, or a derivative thereof.

The present disclosure further provides pharmaceutical compositions comprising a composition of a compound described herein, for treating a disease or condition (e.g., pain) in a subject in need thereof. Other aspects of the disclosure provide methods of treating a disease or condition (e.g., inflammatory disease, infectious disease, or pain) in a subject in need thereof comprising administering to the subject a therapeutically effective amount of a composition of a compound described herein, optionally further comprising illumination of the composition or the pharmaceutical composition with light at an absorption wavelength between approximately 200 nm to 500 nm (e.g., with a LED (e.g., blue LED)). In certain embodiments, the diseases treated and/or prevented include, but are not limited to, inflammatory disease, infectious disease, or pain, for example, pain associated with an infectious disease (e.g., infection by bacteria, virus, or other microbe), ear disease, pain associated with a medical procedure (e.g., surgery (e.g., dental surgery)), pain associated with trauma (e.g., injury), and/or sustained pain. The present disclosure further provides uses of the compounds, compositions, or pharmaceutical compositions thereof described herein, for treating a disease or condition (e.g., inflammatory disease, infectious disease, or pain) in a subject in need thereof, optionally further comprising illumination of the composition or the pharmaceutical composition with light at an absorption wavelength between approximately 200 nm to 500 nm (e.g., with a LED (e.g., blue LED)). Also provided are kits comprising a container with the compounds, compositions, and pharmaceutical compositions described herein, optionally further comprising a light of an absorption wavelength between approximately 200 nm to 500 nm (e.g., with a LED (e.g., blue LED)).

Compositions with Compounds

Certain aspects of the present disclosure relate to the compounds described herein. Provided are compositions comprising macromolecular prodrug compounds described herein. In certain embodiments, a compound described herein is a compound of Formula (I), or a pharmaceutically acceptable salt, co-crystal, tautomer, stereoisomer, solvate, hydrate, polymorph, or an isotopically enriched derivative thereof. In certain embodiments, a compound described herein is a compound of Formula (I), or a pharmaceutically acceptable salt thereof.

In certain embodiments, a composition described herein comprises a compound of Formula (I):

$$P\!-\!(L\!-\!X)_n,\qquad(I)$$

or a pharmaceutically acceptable salt, co-crystal, tautomer, stereoisomer, solvate, hydrate, polymorph, or an isotopically enriched derivative thereof, wherein:
n is an integer of 1 or more;
each instance of X is independently an anesthetic compound;
each instance of L is independently a photocleavable linker; and
P is a polymer.

In certain embodiments, a composition described herein comprises a compound of Formula (I):

$$P\!-\!(L\!-\!X)_n,\qquad(I)$$

or a pharmaceutically acceptable salt, co-crystal, tautomer, stereoisomer, solvate, hydrate, polymorph, or an isotopically enriched derivative thereof, wherein:
n is an integer between 1 and 100,000, inclusive;
each instance of X is independently an anesthetic compound;
each instance of L is independently a photocleavable linker; and
P is a polymer.

In certain embodiments, in Formula (I), n is an integer of 1 or more. In certain embodiments, in Formula (I), n is an integer between 1 and 100,000, inclusive. In certain embodiments, in Formula (I), n is an integer between 1 and 10,000, inclusive. In certain embodiments, in Formula (I), n is an integer between 1 and 9,000, inclusive. In certain embodiments, in Formula (I), n is an integer between 1 and 1,000; between 1,000 and 2,000; between 2,000 and 3,000; between 3,000 and 4,000; between 4,000 and 5,000; between 5,000 and 6,000; between 6,000 and 7,000; between 7,000 and 8,000; between 9,000 and 10,000; between 10,000 and 12,000; between 12,000 and 14,000; between 10,000 and 15,000; between 14,000 and 16,000; between 16,000 and 18,000; between 18,000 and 20,000; between 20,000 and 30,000; between 30,000 and 40,000; between 40,000 and 50,000; between 50,000 and 60,000; between 60,000 and 70,000; between 70,000 and 80,000; between 80,000 and 90,000; or between 90,000 and 100,000. In certain embodiments, in Formula (I), n is an integer between 1 and 200,000, inclusive. In certain embodiments, in Formula (I), n is an integer that is 1 or more, and P is a cross-linked polymer. In certain embodiments, n is 1, 2, 3, 4, 5, 6, 7, 8, 9, or 10. In certain embodiments, n is 1, 2, or 3. In certain embodiments, n is 1, 2, 3, or 4. In certain embodiments, n is 1.

In certain embodiments, a compound of Formula (I) is of Formula (I-A):

X-L-P-L-X  (I-A), or a pharmaceutically acceptable salt, co-crystal, tautomer, stereoisomer, solvate, hydrate, polymorph, or an isotopically enriched derivative thereof.

In some embodiments, the compound is of Formula (I-A):

X-L-P-L-X  (I-A), or a pharmaceutically acceptable salt, co-crystal, tautomer, stereoisomer, solvate, hydrate, polymorph, or an isotopically enriched derivative thereof,
each instance of X is independently a local anesthetic compound;
each instance of L is independently a photocleavable linker; and
P is a hydrophilic or amphiphilic polymer.

In certain embodiments, each instance of L is independently a photocleavable linker; and the bonds between each instance of L and each instance of X is cleaved upon illumination with light at an absorption wavelength between approximately 200 nm to 500 nm.

The terms "sol-gel transition temperature," "phase transition temperature," and "gelation temperature" are used interchangeably. In certain embodiments, the composition forms a gel at a phase transition temperature between about 0° C. and about 40° C. In certain embodiments, the composition forms a gel at a phase transition temperature between about 0° C. and about 39° C. In certain embodiments, the composition forms a gel at a phase transition temperature between about 0° C. and about 37° C. In certain embodiments, the composition forms a gel at a phase transition temperature between about 0° C. and about 35° C. In certain embodiments, the composition forms a gel at temperatures above a phase transition temperature; and the phase transition temperature is about 37° C.

Compounds of Formula (I) include at least two instances of X. In certain embodiments, at least one instance of X is a local anesthetic compound. In certain embodiments, both instances of X are each a local anesthetic compound. In certain embodiments, both instances of X are each the same local anesthetic compound. In certain embodiments, all instances of X are each a local anesthetic compound. In certain embodiments, all instances of X are each the same local anesthetic compound. In certain embodiments, at least one instance of X is an amino ester compound. In certain embodiments, at least one instance of X is a local anesthetic compound that is an amino ester compound with a primary amine group or a local anesthetic compound with a secondary amine group. In certain embodiments, the local anesthetic compound with a primary amine group is of formula:

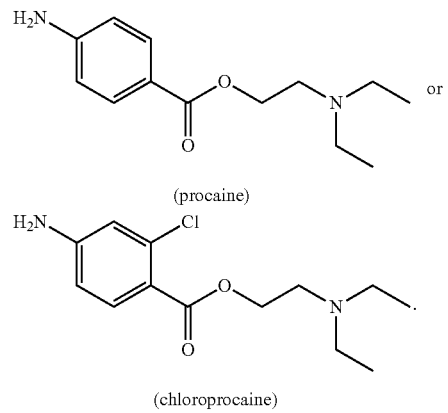

In certain embodiments, the local anesthetic compound with a secondary amine group is of formula:

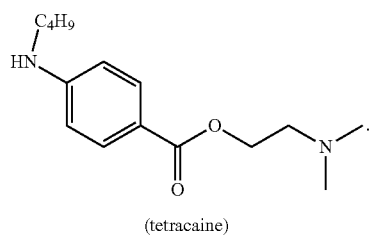

(tetracaine)

In certain embodiments, at least one instance of X is a local anesthetic compound of formula:

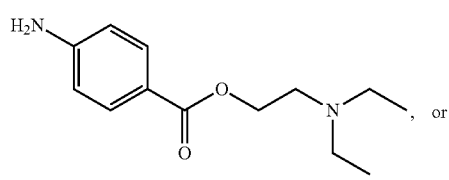

(procaine)

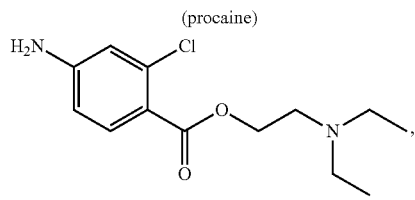

(tetracaine)

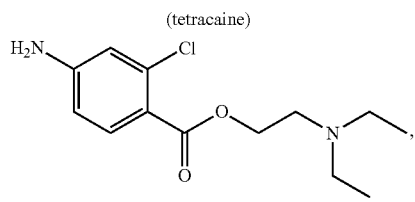

(chloroprocaine)

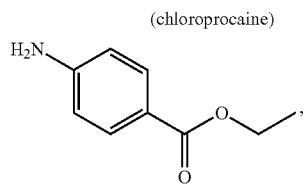

(benzocaine)

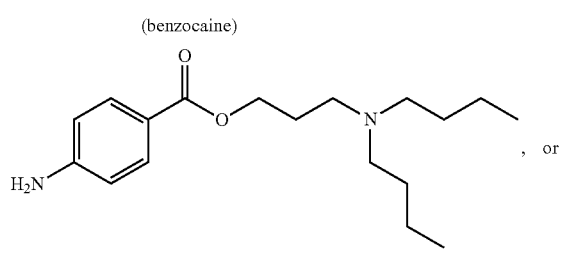

(butacaine)

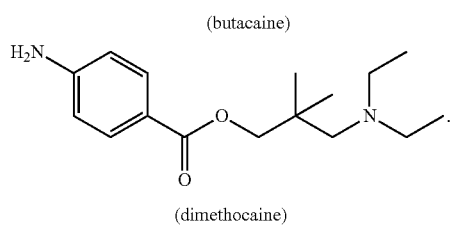

(dimethocaine)

In certain embodiments, the local anesthetic compound with a primary amine group is of formula:

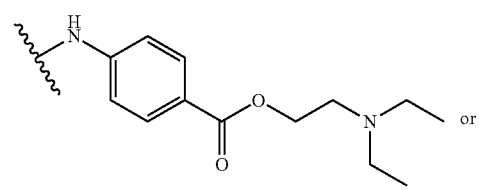

(procaine)

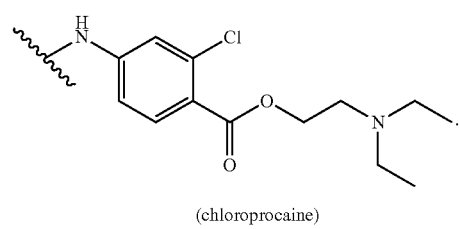

(chloroprocaine)

In certain embodiments, the local anesthetic compound with a secondary amine group is of formula:

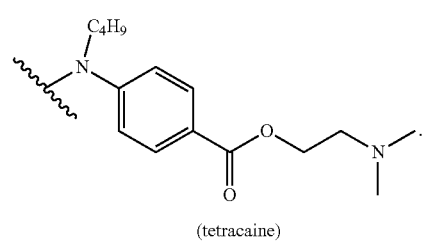

(tetracaine)

In certain embodiments, at least one instance of X is a local anesthetic compound of formula:

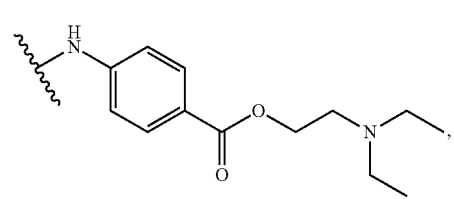

(procaine)

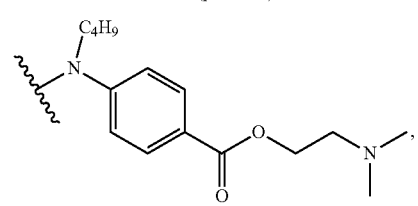

(tetracaine)

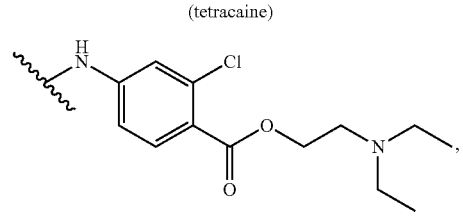

(chloroprocaine)

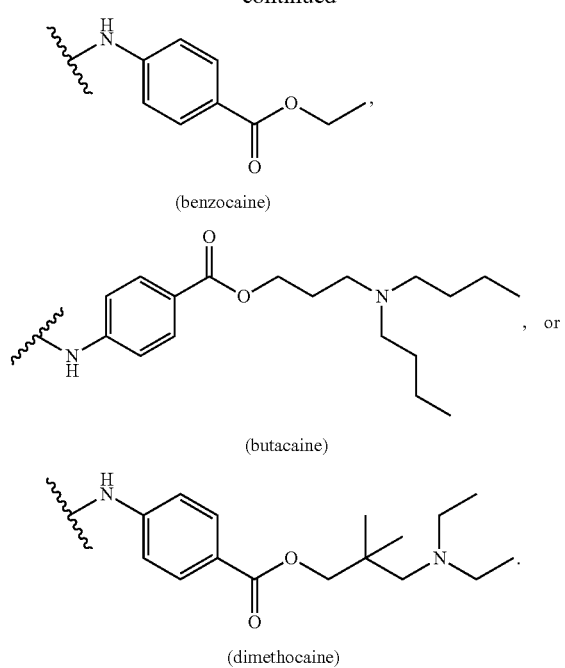

(benzocaine)

(butacaine)

(dimethocaine)

In certain embodiments, both instances of X are each tetracaine. In certain embodiments, both instances of X are each procaine. In certain embodiments, both instances of X are each tetracaine. In certain embodiments, both instances of X are each chloroprocaine. In certain embodiments, both instances of X are each benzocaine. In certain embodiments, both instances of X are each butacaine. In certain embodiments, both instances of X are each dimethocaine. In certain embodiments, all instances of X are each procaine. In certain embodiments, all instances of X are each tetracaine. In certain embodiments, all instances of X are each chloroprocaine. In certain embodiments, all instances of X are each benzocaine. In certain embodiments, all instances of X are each butacaine. In certain embodiments, all instances of X are each or dimethocaine.

In certain embodiments, at least one instance of X is an amino amide compound. In certain embodiments, both instances of X are each an amino amide compound. In certain embodiments, both instances of X are each the same amino amide compound. In certain embodiments, all instances of X are each an amino amide compound. In certain embodiments, all instances of X are each the same amino amide compound. In certain embodiments, at least one instance of the local anesthetic compound X is an amino amide compound of formula:

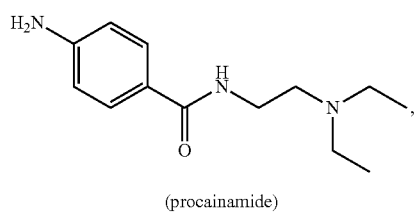

(procainamide)

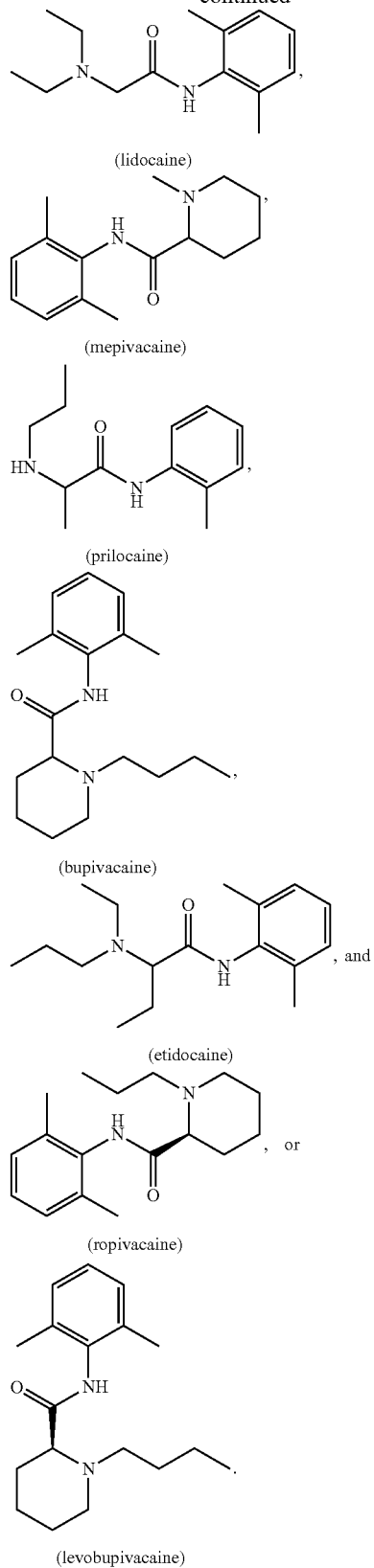

(lidocaine)

(mepivacaine)

(prilocaine)

(bupivacaine)

(etidocaine)

(ropivacaine)

(levobupivacaine)

In certain embodiments, at least one instance of the local anesthetic compound X is an amino amide compound of formula:

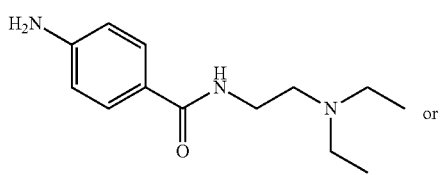

(procainamide)

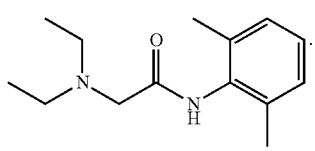

(lidocaine)

In certain embodiments, at least one instance of the local anesthetic compound X is an amino amide compound of formula:

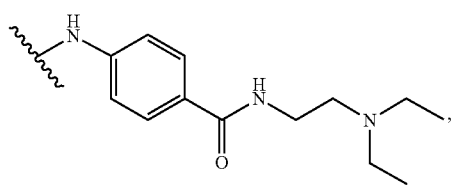

(procainamide)

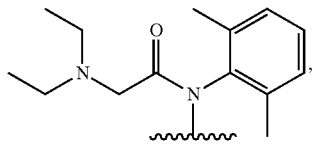

(lidocaine)

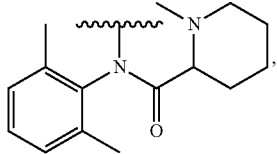

(mepivacaine)

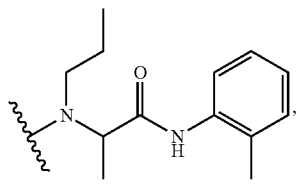

(prilocaine)

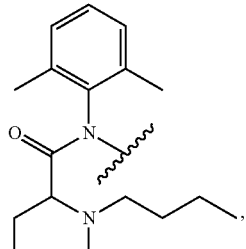

(buvpivacaine)

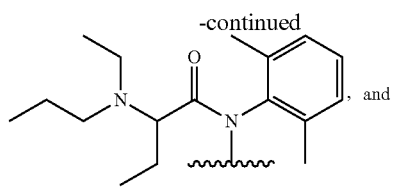

(etidocaine)

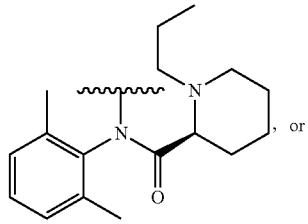

(ropivacaine)

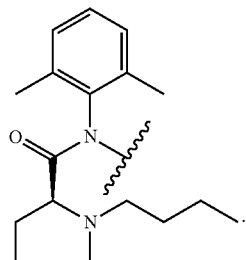

(levobupivacaine)

In certain embodiments, at least one instance of the local anesthetic compound X is an amino amide compound of formula:

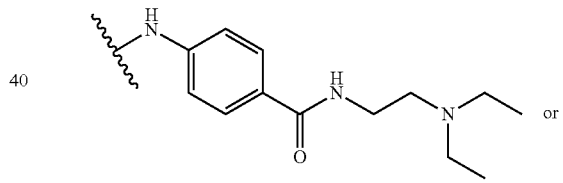

(procainamide)

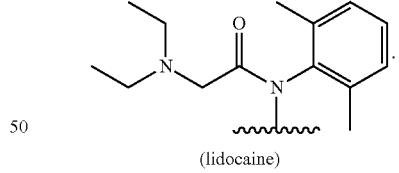

(lidocaine)

In certain embodiments, at least one instance of the local anesthetic compound X is an amino amide compound of formula:

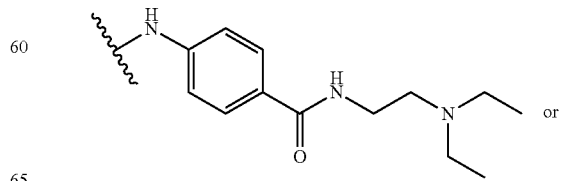

(procainamide)

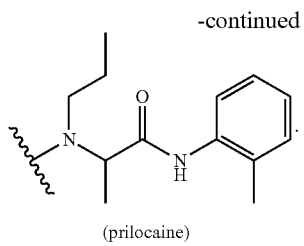

(prilocaine)

In certain embodiments, both instances of X are each procainamide. In certain embodiments, both instances of X are each lidocaine. In certain embodiments, both instances of X are each prilocaine. In certain embodiments, all instances of X are each procainamide. In certain embodiments, all instances of X are each lidocaine. In certain embodiments, all instances of X are each prilocaine.

Compounds of Formula (I) include polymer P. In certain embodiments, P is a hydrophilic or amphiphilic polymer. In certain embodiments, P is a hydrophilic polymer. In certain embodiments, P is an amphiphilic polymer. In certain embodiments, the amphiphilic polymer is a poloxamer (Pluronics®). In certain embodiments, P is a copolymer. In certain embodiments, the polymer is biodegradable. In certain embodiments, the polymer is a copolymer. In certain embodiments, the copolymer is biodegradable or comprises biodegradable monomers. In certain embodiments, the copolymer is a block copolymer. In certain embodiments the copolymer comprises at least one block of hydrophobic monomers. In certain embodiments, the copolymer comprises at least one block of hydrophobic monomers, and at least one block of non-hydrophobic monomers. In certain embodiments, the copolymer comprises at least one block of hydrophobic monomers, and at least one block of hydrophilic monomers. In certain embodiments, P is a hydrophobic polymer. In certain embodiments, P is a cross-linked polymer. In certain embodiments, P is a polysaccharide or a polypeptide. In certain embodiments, P is hyaluronic acid. In certain embodiments, P is polyglutamic acid. In certain embodiments, P is a brush polymer, for example, a bottle-brush polymer. In certain embodiments, P is not a hydrophobic polymer. In certain embodiments, P is not hyaluronic acid or polyglutamic acid.

In certain embodiments, the copolymer comprises polyethylene oxide, polypropylene oxide, and/or a poloxamer, or copolymers of combinations thereof. In certain embodiments, the copolymer comprises a poloxamer. In certain embodiments, the poloxamer is poloxamer P407, poloxamer P331, poloxamer P188, poloxamer P182, poloxamer P124, poloxamer P338, or poloxamer P237 (F87), or combinations thereof. In certain embodiments, P is poloxamer P407, poloxamer P331, poloxamer P188, poloxamer P182, poloxamer P124, poloxamer P338, or poloxamer P237 (F87). In certain embodiments, P is poloxamer P407 (P407). In certain embodiments, P is poloxamer P331. In certain embodiments, P is poloxamer P188. In certain embodiments, P is poloxamer P182. In certain embodiments, P is poloxamer P124. In certain embodiments, P is poloxamer P338. In certain embodiments, P is poloxamer P237 (F87).

Compounds of Formula (I) include at least two instances of photocleavable linker L connecting polymer P and the anesthetic compound X. In certain embodiments, both instances of L are the same. In certain embodiments, all instances of L are the same. In certain embodiments, L comprises L1, which comprises an aryl- or heteroaryl-containing moiety. In certain embodiments, at least one instance of L comprises coumarin, o-nitrobenzyl, benzoin, 7-nitroindoline, or p-hydroxyphenacyl, or a derivative thereof. In certain embodiments, at least one instance of L comprises coumarin, o-nitrobenzyl, benzoin, 7-nitroindoline, or p-hydroxyphenacyl. In certain embodiments, at least one instance of L comprises coumarin. In certain embodiments, at least one instance of L1 comprises coumarin, o-nitrobenzyl, benzoin, 7-nitroindoline, or p-hydroxyphenacyl, or a derivative thereof. In certain embodiments, at least one instance of L1 comprises coumarin, o-nitrobenzyl, benzoin, 7-nitroindoline, or p-hydroxyphenacyl. In certain embodiments, at least one instance of L1 comprises coumarin. In certain embodiments, at least one instance of the moiety

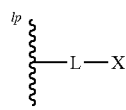

is of formula:

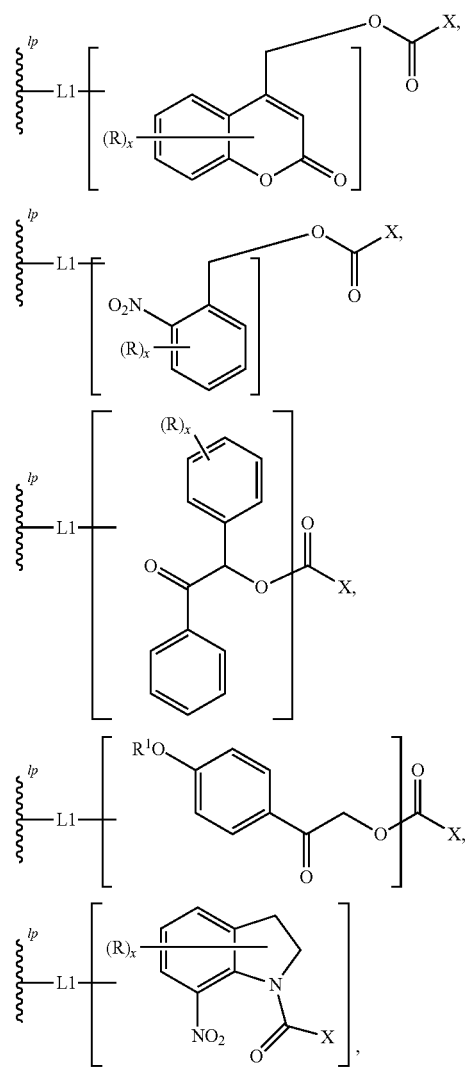

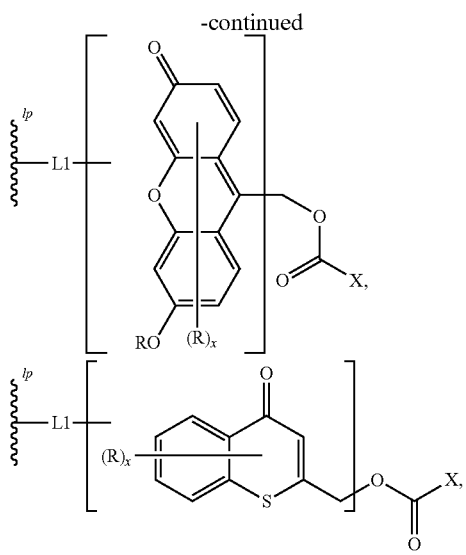

wherein L1 is an alkylene linker wherein one or more carbon atoms are optionally replaced with —O—, —N(R$^a$)—, —C(=O)—, optionally substituted phenyl, or

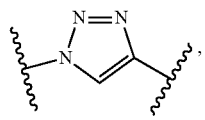 [SMILES: *c1cn(*)nn1]

and lp indicates the attachment to P; R$^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

R$^a$ is hydrogen, optionally substituted acyl, optionally substituted alkyl, optionally substituted alkenyl, optionally substituted alkynyl, or a nitrogen protecting group;

each instance of R is independently halogen, optionally substituted acyl, optionally substituted alkyl, optionally substituted heteroalkyl, optionally substituted alkenyl, optionally substituted alkynyl, optionally substituted carbocyclyl, optionally substituted heterocyclyl, optionally substituted aryl, optionally substituted heteroaryl, —OR$^{c1}$, —NO$_2$, —N(R$^{c2}$)$_2$, —SR$^{c1}$, or —CN;

R$^{c1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^{c2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of R$^{c2}$ are taken together with their intervening atoms to form a substituted or unsubstituted heterocyclic or substituted or unsubstituted heteroaryl ring; and x is 0, 1, 2, 3, 4, 5, 6, or 7, as valency permits.

In certain embodiments, at least one instance of L1 is an alkylene linker wherein one or more carbon atoms of the hydrocarbon chain are optionally replaced with —O—, —N(R$^a$)—, —C(=O)—, optionally substituted phenyl, or

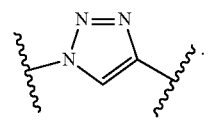 [SMILES: *c1cn(*)nn1]

In certain embodiments, at least one instance of L1 is a C$_{1-20}$ alkylene linker wherein one or more carbon atoms of the hydrocarbon chain are optionally replaced with —O—, —N(R$^a$)—, —C(=O)—, optionally substituted phenyl, or

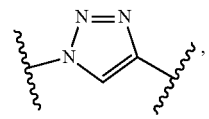 [SMILES: *c1cn(*)nn1]

and R$^a$ is hydrogen, optionally substituted acyl, optionally substituted alkyl, optionally substituted alkenyl, optionally substituted alkynyl, or a nitrogen protecting group. In certain embodiments, at least one instance of L1 is a C$_{1-10}$ alkylene linker wherein one or more carbon atoms of the hydrocarbon chain are optionally replaced with —O—, —N(R$^a$)—, —C(=O)—, optionally substituted phenyl, or

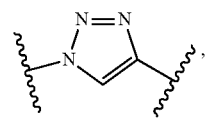

and R$^a$ is hydrogen, optionally substituted acyl, optionally substituted alkyl, optionally substituted alkenyl, optionally substituted alkynyl, or a nitrogen protecting group.

In certain embodiments, L1 comprises up to 20 atoms in the hydrocarbon chain, excluding hydrogen atoms and substituents. In certain embodiments, L1 comprises up to 14 atoms in the hydrocarbon chain, excluding hydrogen atoms and substituents. In certain embodiments, L1 comprises up to 15 in the hydrocarbon chain, excluding hydrogen atoms and substituents. In certain embodiments, L1 comprises up to 12 atoms in the hydrocarbon chain, excluding hydrogen atoms and substituents. In certain embodiments, L1 comprises up to 10 atoms in the hydrocarbon chain, excluding hydrogen atoms and substituents. In certain embodiments, L1 comprises up to 9 atoms in the hydrocarbon chain, excluding hydrogen atoms and substituents. In certain embodiments, L1 comprises up to 6 atoms in the hydrocarbon chain, excluding hydrogen atoms and substituents. In certain embodiments, L1 comprises up to 5 atoms in the hydrocarbon chain, excluding hydrogen atoms and substituents. In certain embodiments, L1 comprises up to 3 atoms in the hydrocarbon chain, excluding hydrogen atoms and substituents.

In certain embodiments, any of the atoms in L1 can be substituted. In certain embodiments, none of the atoms in the linker L1 are substituted. In certain embodiments, none of the carbon atoms in the linker are substituted.

In certain embodiments, one or more carbon units of the hydrocarbon chain L1 are independently replaced with at least one instance of —O—. In certain embodiments, one or more carbon units of the hydrocarbon chain L1 are independently replaced with at least one instance of —C=O—. In certain embodiments, one or more carbon units of the hydrocarbon chain L1 are independently replaced with at least one instance of —NR$^a$—, wherein R$^a$ is hydrogen, optionally substituted acyl, optionally substituted alkyl, optionally substituted alkenyl, optionally substituted alkynyl, or a nitrogen protecting group. In certain embodiments, one or more carbon units of the hydrocarbon chain L1 are independently replaced with at least one instance of —NR$^a$—, wherein R$^a$ is hydrogen, optionally substituted acyl, or optionally substituted alkyl. In certain embodiments, one or more carbon units of the hydrocarbon chain L1 are independently replaced with at least one instance of optionally substituted phenyl. In certain embodiments, one or more carbon units of the hydrocarbon chain L1 are independently replaced with at least one instance of unsubstituted phenyl. In certain embodiments, one or more carbon units of the hydrocarbon chain L1 are independently replaced with at least one instance of the moiety

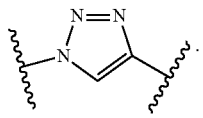 [SMILES: *c1cn(*)nn1]

In certain embodiments, at least one carbon unit of the hydrocarbon chain L1 are independently replaced with at least one instance of the moiety

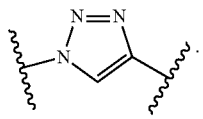 [SMILES: *c1cn(*)nn1]

In certain embodiments, one carbon unit of the hydrocarbon chain L1 are independently replaced with at least one instance of the moiety

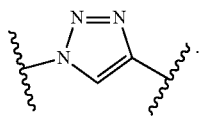 [SMILES: *c1cn(*)nn1]

In certain embodiments, R$^a$ is hydrogen. In certain embodiments, R$^a$ is optionally substituted alkyl (e.g., substituted or unsubstituted $C_{1-6}$ alkyl). In certain embodiments, R$^a$ is optionally substituted $C_{1-6}$ alkyl. In certain embodiments, R$^a$ is substituted or unsubstituted methyl. In certain embodiments, R$^a$ is substituted or unsubstituted ethyl. In certain embodiments, R$^a$ is unsubstituted ethyl. In certain embodiments, R$^a$ is substituted or unsubstituted propyl. In certain embodiments, R$^a$ is unsubstituted n-propyl. In certain embodiments, R$^a$ is unsubstituted methyl or isopropyl. In certain embodiments, R$^a$ is optionally substituted alkenyl (e.g., substituted or unsubstituted $C_{2-6}$ alkenyl). In certain embodiments, R$^a$ is optionally substituted alkynyl (e.g.,
substituted or unsubstituted $C_{2-6}$ alkynyl). In certain embodiments, R$^a$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, L1 is of the formula:

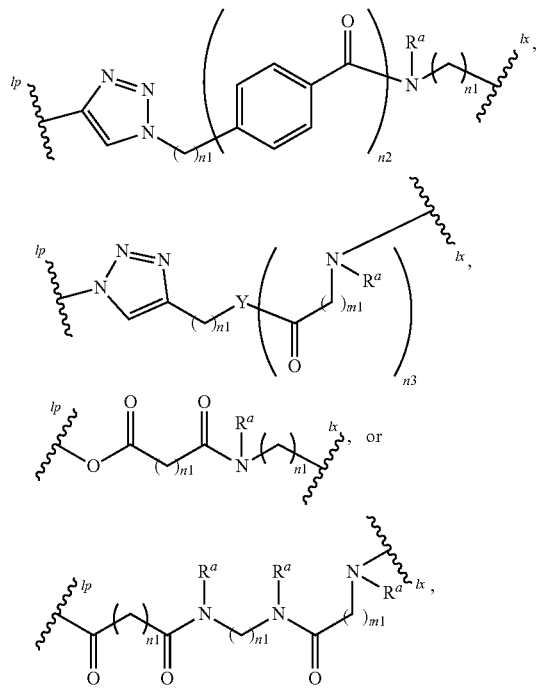

wherein:
Y is —O— or —NR$^a$—;
R$^a$ is hydrogen, optionally substituted acyl, or optionally substituted alkyl;
m1 is 0 or 1;
each instance of n1 is independently 0, 1, or 2;
n2 is 0 or 1;
n3 is 0 or 1; and
$^{lp}$ indicates the point of attachment to P and $^{lx}$ indicates the point of attachment to X.

In certain embodiments, at least one instance of the moiety

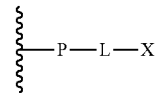

is of the formula:

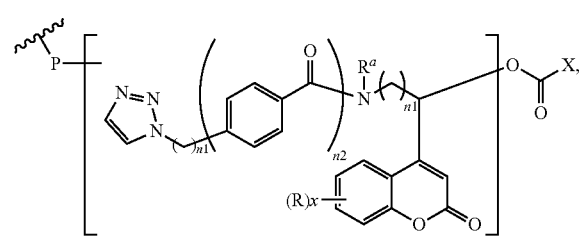

wherein: each instance of n1 is independently 0 or 1; and n2 is 0 or 1.

In certain embodiments, at least one instance of the moiety

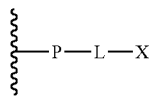

is of the formula:

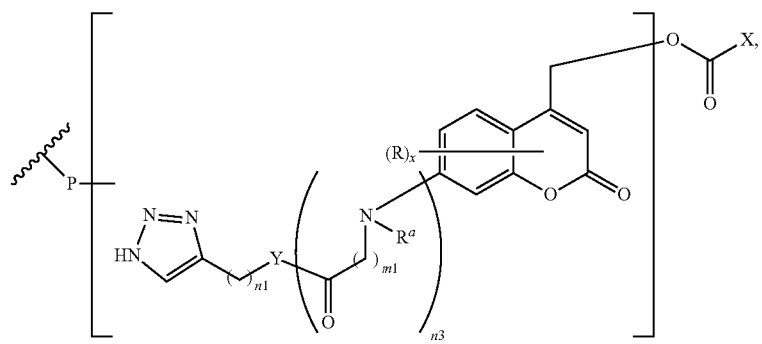

wherein: Y is —O— or —NR$^a$—; R$^a$ is hydrogen, optionally substituted acyl, or optionally substituted alkyl; m1 is 0 or 1; n1 is 0 or 1; and n3 is 0 or 1.

In certain embodiments, at least one instance of the moiety

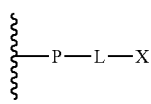

is of the formula:

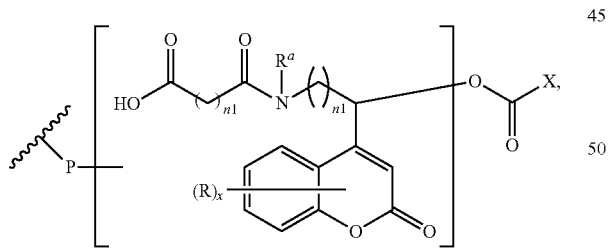

wherein: R$^a$ is hydrogen, optionally substituted acyl, or optionally substituted alkyl; and n1 is 0, 1, or 2.

In certain embodiments, at least one instance of the moiety

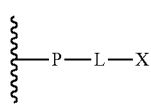

is of the formula:

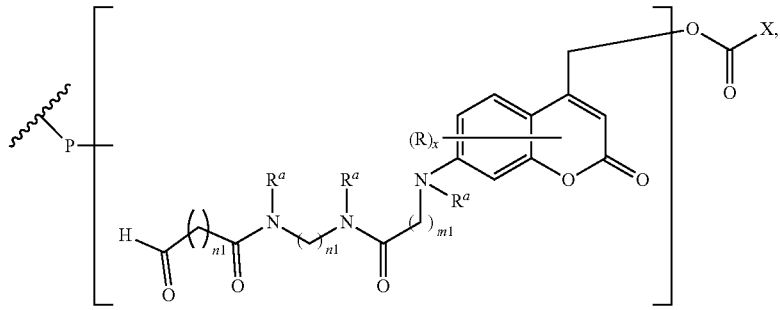

wherein: $R^a$ is hydrogen, optionally substituted acyl, or optionally substituted alkyl; m1 is 0 or 1; and n1 is 0, 1, or 2.

In certain embodiments, at least one instance of the moiety

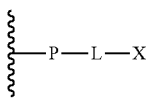

is of the formula:

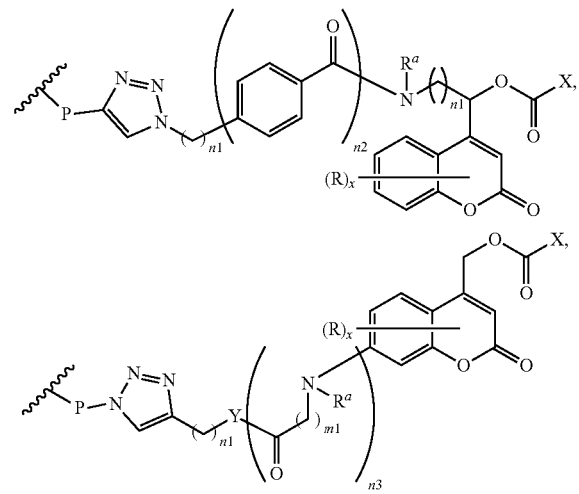

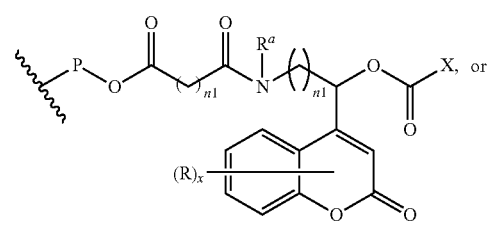

-continued

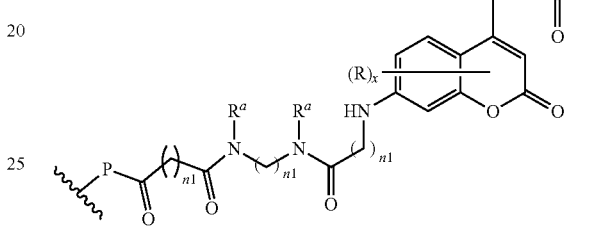

In certain embodiments, at least one instance of Y is —O—. In certain embodiments, at least one instance of Y is —$NR^a$—, and $R^a$ is hydrogen, optionally substituted acyl, or optionally substituted alkyl. In certain embodiments, at least one instance of Y is —NH—. In certain embodiments, all instances of Y are —NH—. In certain embodiments, at least one instance of Y is —$N(CH_2)_{1-6}$—. In certain embodiments, at least one instance of Y is —N(optionally substituted $C_{1-6}$ alkyl)-. In certain embodiments, at least one instance of Y is —N(Me)-. In certain embodiments, at least one instance of Y is —N(Et)-. In certain embodiments, at least one instance of Y is —$NR^a$—, and $R^a$ is hydrogen or optionally substituted $C_{1-6}$ alkyl. In certain embodiments, at least one instance of Y is —NH— and another instance of Y is —N(optionally substituted $C_{1-6}$ alkyl)-. In certain embodiments, at least one instance of Y is —NH— and another instance of Y is —N(Et)-.

In certain embodiments, the moiety

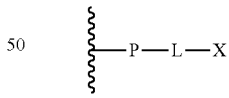

includes one or more of m1, n1, n2, and n3. In certain embodiments, m1 is 0. In certain embodiments, m1 is 1. In certain embodiments, at least one instance of n1 is 0. In certain embodiments, at least one instance of n1 is 1. In certain embodiments, at least one instance of n1 is 2. In certain embodiments, both instances of n1 are 2. In certain embodiments, n2 is 0. In certain embodiments, n2 is 1. In certain embodiments, n3 is 0. In certain embodiments, n3 is 1. In certain embodiments, n1 is 1, m1 is 1, and n3 is 1. In certain embodiments, n1 is 2, m1 is 1, and n3 is 1. In certain embodiments, n1 is 1 and n3 is 0. In certain embodiments, n1 is 0 and n3 is 1. In certain embodiments, both instances of n1 are 2 and m1 is 1. In certain embodiments, both instances of n1 are 2 and m1 is 0. In certain embodiments, at least one instance of n1 is 1 and m1 is 1. In certain embodiments, one instance of n1 is 1, a second instance of n1 is 2, and m1 is 1.

In certain embodiments, the photocleavable linker L includes substituent $R^1$. In certain embodiments, $R^1$ is hydrogen. In certain embodiments, $R^1$ is optionally substituted acyl (e.g., —C(═O)Me). In certain embodiments, $R^1$ is optionally substituted alkyl (e.g., substituted or unsubstituted $C_{1-6}$ alkyl). In certain embodiments, $R^1$ is substituted or unsubstituted methyl. In certain embodiments, $R^1$ is substituted or unsubstituted ethyl. In certain embodiments, $R^1$ is unsubstituted ethyl. In certain embodiments, $R^1$ is substituted or unsubstituted propyl. In certain embodiments, $R^1$ is unsubstituted n-propyl. In certain embodiments, $R^1$ is unsubstituted methyl or isopropyl. In certain embodiments, $R^1$ is optionally substituted alkenyl (e.g., substituted or unsubstituted $C_{2-6}$ alkenyl). In certain embodiments, $R^1$ is optionally substituted alkynyl (e.g., substituted or unsubstituted $C_{2-6}$ alkynyl). In certain embodiments, $R^1$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^1$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^1$ is optionally substituted aryl (e.g., substituted or unsubstituted, 6- to 10-membered aryl). In certain embodiments, $R^1$ is benzyl. In certain embodiments, $R^1$ is substituted or unsubstituted phenyl. In certain embodiments, $R^1$ is unsubstituted phenyl. In certain embodiments, $R^1$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^1$ is an oxygen protecting group (e.g., methyl, methoxylmethyl (MOM), methylthiomethyl (MTM), t-butylthiomethyl, (phenyldimethylsilyl)methoxymethyl (SMOM), benzyloxymethyl (BOM)), trimethylsilyl (TMS), triethylsilyl (TES), triisopropylsilyl (TIPS)).

In certain embodiments, the photocleavable linker L includes one or more instances of substituent R, as valency permits. In certain embodiments, x is 0. In certain embodiments, x is 1. In certain embodiments, x is 2. In certain embodiments, x is 3. In certain embodiments, x is 4. In certain embodiments, x is 5. In certain embodiments, x is 6. In certain embodiments, x is 7. In certain embodiments, at least one instance of R is halogen (e.g., F, Cl, Br, or I).

In certain embodiments, at least one instance of R is optionally substituted acyl (e.g., —C(═O)Me). In certain embodiments, at least one instance of R is optionally substituted alkyl (e.g., substituted or unsubstituted $C_{1-6}$ alkyl). In certain embodiments, at least one instance of R is substituted or unsubstituted methyl. In certain embodiments, at least one instance of R is substituted or unsubstituted ethyl. In certain embodiments, at least one instance of R is substituted or unsubstituted propyl. In certain embodiments, at least one instance of R is optionally substituted alkenyl (e.g., substituted or unsubstituted $C_{2-6}$ alkenyl). In certain embodiments, at least one instance of R is optionally substituted alkynyl (e.g., substituted or unsubstituted $C_{2-6}$ alkynyl). In certain embodiments, at least one instance of R is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of R is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of R is optionally substituted aryl (e.g., substituted or unsubstituted, 6- to 10-membered aryl). In certain embodiments, at least one instance of R is benzyl. In certain embodiments, at least one instance of R is substituted or unsubstituted phenyl. In certain embodiments, at least one instance of R is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of R is —$OR^{c1}$ (e.g., —OH or —OMe). In certain embodiments, at least one instance of R is —$N(R^{c2})_2$ (e.g., —$NMe_2$, —$NEt_2$). In certain embodiments, at least one instance of R is —$N(R^{c2})_2$ and at least one instance of $R^{c2}$ is optionally substituted alkyl. In certain embodiments, at least one instance of R is —$NEt_2$. In certain embodiments, x is 1 and R is —$NEt_2$. In certain embodiments, at least one instance of R is —$SR^{c1}$ (e.g., —SMe). In certain embodiments, at least one instance of R is —CN. In certain embodiments, at least one instance of R is —SCN.

In certain embodiments, at least one instance of R is —$OR^{c1}$, —$N(R^{c2})_2$, or —$SR^{c1}$ and $R^{c1}$ is as defined herein. In certain embodiments, $R^{c1}$ is hydrogen. In certain embodiments, $R^{c1}$ is substituted or unsubstituted acyl (e.g., —C(═O)Me). In certain embodiments, $R^{c1}$ is substituted or unsubstituted alkyl (e.g., substituted or unsubstituted $C_{1-6}$ alkyl). In certain embodiments, $R^{c1}$ is substituted or unsubstituted methyl. In certain embodiments, $R^{c1}$ is substituted or unsubstituted ethyl. In certain embodiments, $R^{c1}$ is substituted or unsubstituted propyl. In certain embodiments, $R^{c1}$ is substituted or unsubstituted alkenyl (e.g., substituted or unsubstituted $C_{2-6}$ alkenyl). In certain embodiments, $R^{c1}$ is substituted or unsubstituted alkynyl (e.g., substituted or unsubstituted $C_{2-6}$ alkynyl). In certain embodiments, $R^{c1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{c1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{c1}$ is substituted or unsubstituted aryl (e.g., substituted or unsubstituted, 6- to 10-membered aryl). In certain embodiments, $R^{c1}$ is benzyl. In certain embodiments, $R^{c1}$ is substituted or unsubstituted phenyl. In certain embodiments, $R^{c1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{c1}$ is an oxygen protecting group (e.g., methyl, methoxylmethyl (MOM), methylthiomethyl (MTM), t-butylthiomethyl, (phenyldimethylsilyl)methoxymethyl (SMOM), benzyloxymethyl (BOM)), trimethylsilyl (TMS), triethylsilyl (TES), triisopropylsilyl (TIPS)) when attached to an oxygen atom. In certain embodiments, $R^{c1}$ is a sulfur protecting group when attached to a sulfur atom.

In certain embodiments, at least one instance of $R^{c2}$ is hydrogen. In certain embodiments, at least one instance of $R^{c2}$ is substituted or unsubstituted acyl (e.g., —C(=O)Me). In certain embodiments, at least one $R^{c2}$ is substituted or unsubstituted alkyl (e.g., substituted or unsubstituted $C_{1-6}$ alkyl). In certain embodiments, at least one instance of $R^{c2}$ is substituted or unsubstituted methyl. In certain embodiments, at least one instance of $R^{c2}$ is substituted or unsubstituted ethyl. In certain embodiments, at least one instance of $R^{c2}$ is substituted or unsubstituted propyl. In certain embodiments, at least one instance of $R^{c2}$ is substituted or unsubstituted alkenyl (e.g., substituted or unsubstituted $C_{2-6}$ alkenyl). In certain embodiments, at least one instance of $R^{c2}$ is substituted or unsubstituted alkynyl (e.g., substituted or unsubstituted $C_{2-6}$ alkynyl). In certain embodiments, at least one instance of $R^{c2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{c2}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{c2}$ is substituted or unsubstituted aryl (e.g., substituted or unsubstituted, 6- to 10-membered aryl). In certain embodiments, at least one instance of $R^{c2}$ is benzyl. In certain embodiments, at least one instance of $R^{c2}$ is substituted or unsubstituted phenyl. In certain embodiments, at least one instance of $R^{c2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{c2}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{c2}$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, at least one instance of the moiety

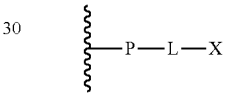

is of the formula:

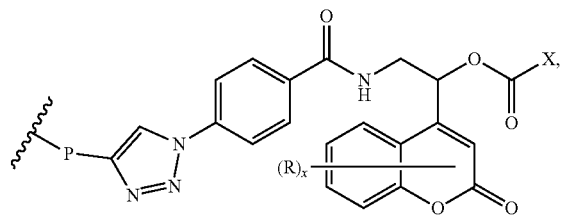

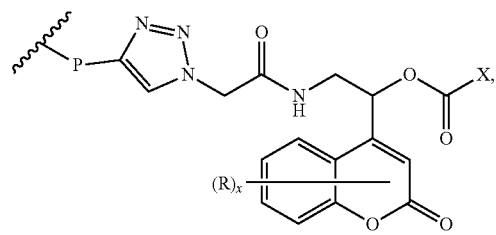

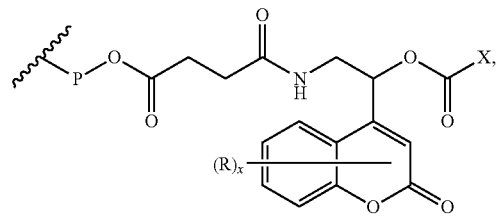

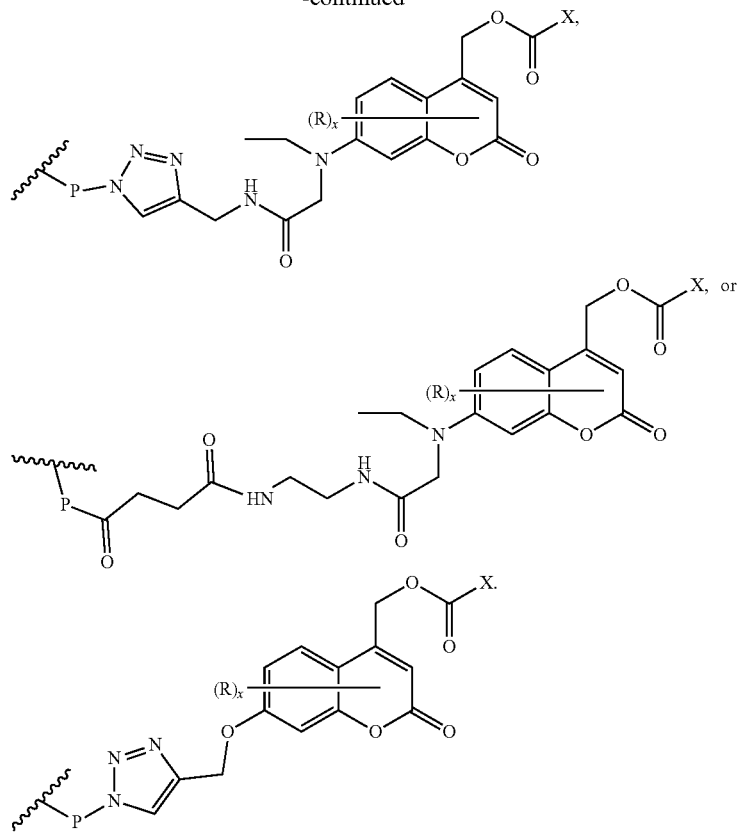
In certain embodiments, at least one instance of the moiety
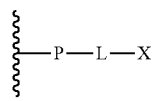
of the formula:
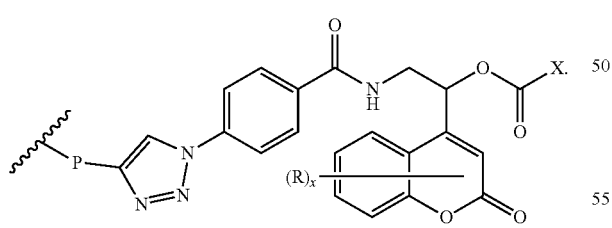
In certain embodiments, at least one instance of the moiety
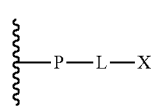
is of the formula:
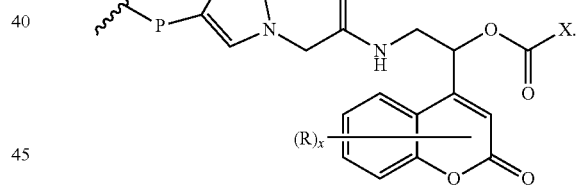
In certain embodiments, at least one instance of the moiety
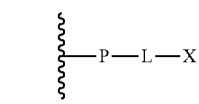
is of the formula:
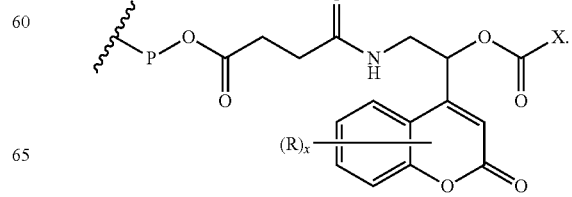

In certain embodiments, at least one instance of the moiety

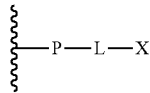

is of the formula:

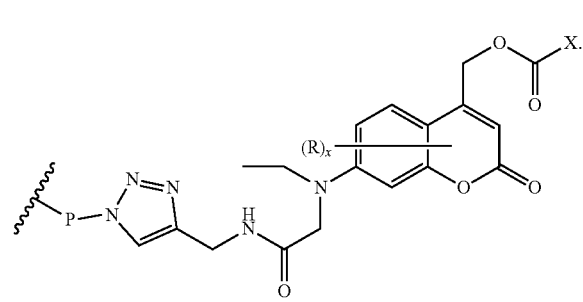

In certain embodiments, at least one instance of the moiety

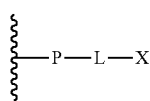

is of the formula:

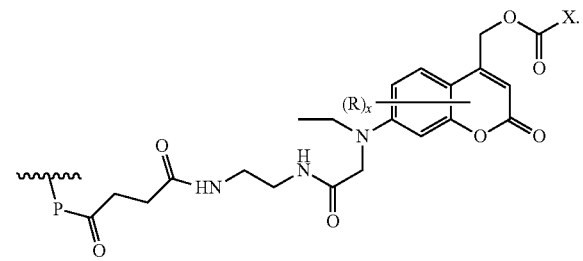

In certain embodiments, at least one instance of the moiety

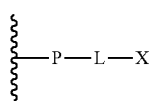

is of the formula:

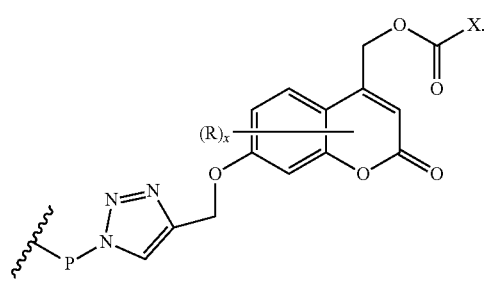

In certain embodiments, at least one instance of the moiety

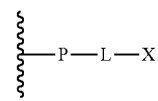

is of the formula:

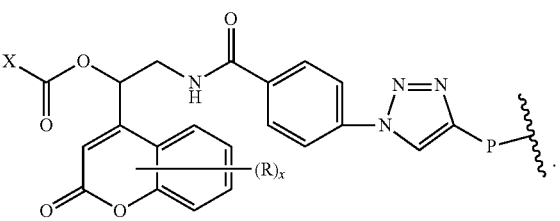

In certain embodiments, at least one instance of the moiety

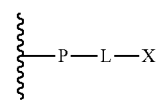

is of the formula:

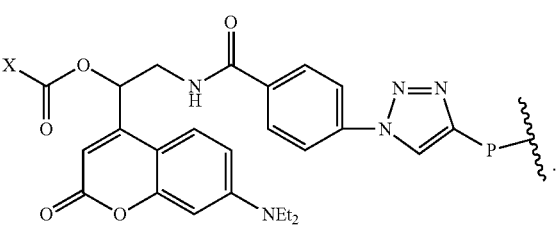

In certain embodiments, at least one instance of the moiety

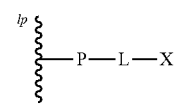

is of the formula:

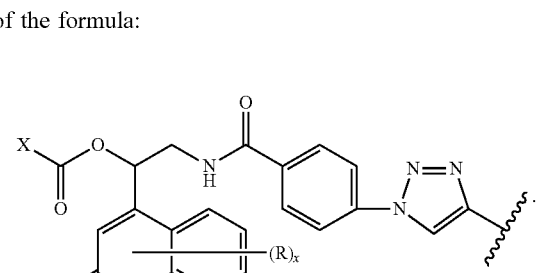

In certain embodiments, at least one instance of the moiety

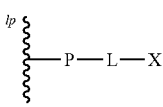

is of the formula:

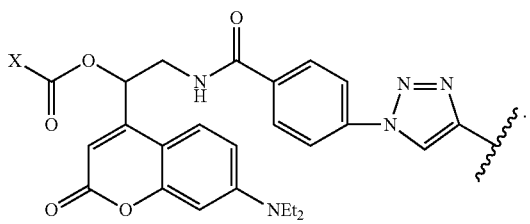

In certain embodiments, both instances of L are the same. In certain embodiments, all instances of L are the same. In certain embodiments, both instances of the moiety

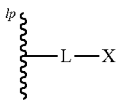

are the same. In certain embodiments, all instances of the moiety

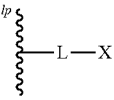

are the same. In certain embodiments, both instances of the moiety

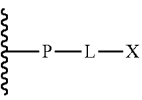

are the same. In certain embodiments, all instances of the moiety

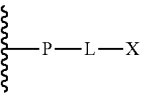

are the same.

In certain embodiments, the compound of Formula (I) is of formula (I-A):

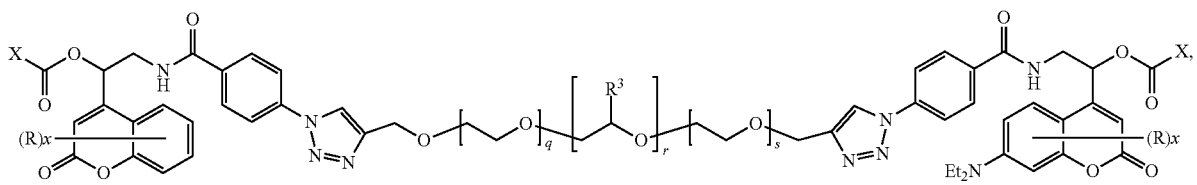

(I-A)

or a pharmaceutically acceptable salt, co-crystal, tautomer, stereoisomer, solvate, hydrate, polymorph, or an isotopically enriched derivative thereof, wherein:

each instance of $R^3$ is independently optionally substituted alkyl, optionally substituted alkenyl, optionally substituted alkynyl, optionally substituted aryl, optionally substituted heteroaryl, optionally substituted acyl, —$OR^b$, or —$N(R^b)_2$;

each instance of $R^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^b$ taken together with the nitrogen to which they are attached form an optionally substituted heterocyclic or optionally substituted heteroaryl ring;

each of q, r, and s is independently an integer between 0 and 200; and the sum of q, r, and s is at least 1.

In certain embodiments, the compound of Formula (I) is of formula (I-a):

(I-a)

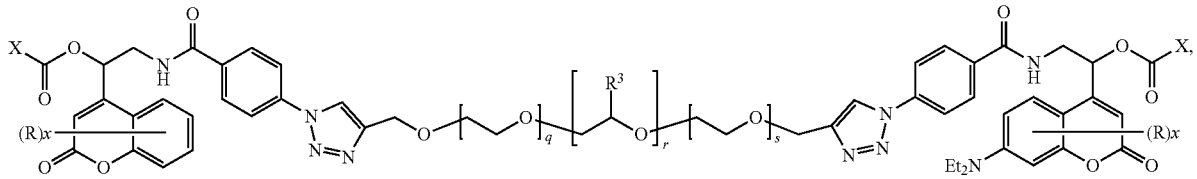

or a pharmaceutically acceptable salt, co-crystal, tautomer, stereoisomer, solvate, hydrate, polymorph, or an isotopically enriched derivative thereof, wherein:
- each instance of $R^3$ is independently optionally substituted alkyl, optionally substituted alkenyl, optionally substituted alkynyl, optionally substituted aryl, optionally substituted heteroaryl, optionally substituted acyl, —$OR^b$, or —$N(R^b)_2$;
- each instance of $R^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^b$ taken together with the nitrogen to which they are attached form an optionally substituted heterocyclic or optionally substituted heteroaryl ring;
- each of q, r, and s is independently an integer between 0 and 200; and the sum of q, r, and s is at least 1.

In certain embodiments, the compound of Formula (I) is of formula (I-A):

(I-A)

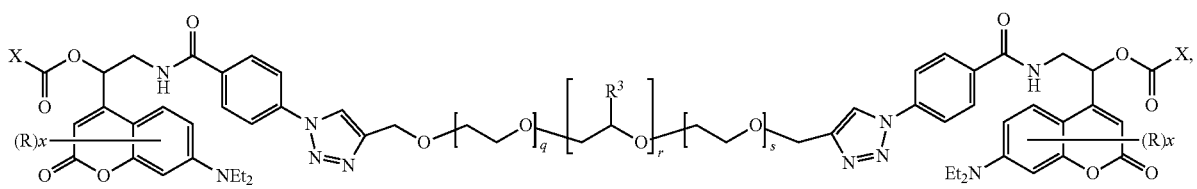

or a pharmaceutically acceptable salt thereof.

In certain embodiments, the compound of Formula (I) is of formula (I-a):

(I-a)

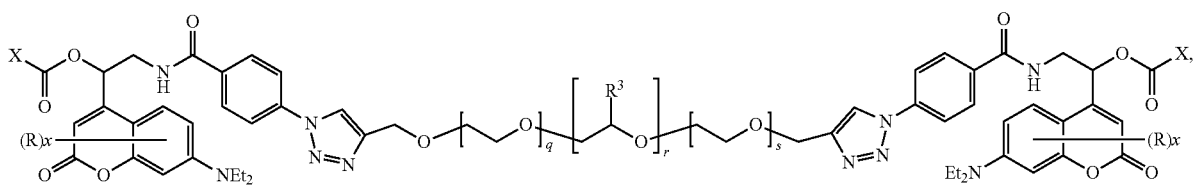

or a pharmaceutically acceptable salt thereof.

In certain embodiments, at least one instance of $R^3$ is optionally substituted acyl (e.g., —C(=O)Me). In certain embodiments, at least one instance of $R^3$ is optionally substituted alkyl (e.g., substituted or unsubstituted $C_{1-6}$ alkyl). In certain embodiments, at least one instance of $R^3$ is substituted or unsubstituted $C_{1-6}$ alkyl. In certain embodiments, at least one instance of $R^3$ is unsubstituted $C_{1-6}$ alkyl. In certain embodiments, at least one instance of $R^3$ is substituted or unsubstituted methyl. In certain embodiments, at least one instance of $R^3$ is unsubstituted methyl. In certain embodiments, at least one instance of $R^3$ is substituted or unsubstituted ethyl. In certain embodiments, at least one instance of $R^3$ is substituted or unsubstituted propyl. In certain embodiments, at least one instance of $R^3$ is optionally substituted alkenyl (e.g., substituted or unsubstituted $C_{2-6}$ alkenyl). In certain embodiments, at least one instance of $R^3$ is optionally substituted alkynyl (e.g., substituted or unsubstituted $C_{2-6}$ alkynyl). In certain embodiments, at least one instance of $R^3$ is optionally substituted aryl (e.g., substituted or unsubstituted, 6- to 10-membered aryl). In certain embodiments, at least one instance of $R^3$ is benzyl. In certain embodiments, at least one instance of $R^3$ is substituted or unsubstituted phenyl. In certain embodiments, at least one instance of $R^3$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^3$ is —$OR^b$ (e.g., —OH or —OMe). In certain embodiments, at least one instance of $R^3$ is —$N(R^b)_2$ (e.g., —$NMe_2$).

In certain embodiments, q is 0. In some embodiments, q is an integer between 10 and 50, inclusive. In some embodiments, q is an integer between 10 and 25, inclusive. In some embodiments, q is an integer between 1 and 10, inclusive. In certain embodiments, q is an integer between 1 and 100, inclusive. In some embodiments, q is an integer between 10 and 100, inclusive. In some embodiments, q is an integer between 50 and 75, between 75 and 100, between 100 and 125, between 125 and 150, between 150 and 175, or between 175 and 200, inclusive. In certain embodiments, q is 100. In certain embodiments, q is 101.

In certain embodiments, r is 0. In certain embodiments, r is an integer between 1 and 100, inclusive. In some embodiments, r is an integer between 10 and 100, inclusive. In some embodiments, r is an integer between 10 and 50, inclusive. In some embodiments, r is an integer between 10 and 25, inclusive. In some embodiments, r is an integer between 1 and 10, inclusive. In some embodiments, r is an integer between 25 and 75, r is an integer between 25 and 50, r is an integer between 50 and 60, r is an integer between 50 and 70, r is an integer between 50 and 75, between 75 and 100, between 100 and 125, between 125 and 150, between 150 and 175, or between 175 and 200, inclusive. In certain embodiments, r is 50. In certain embodiments, r is 55. In certain embodiments, r is 56.

In certain embodiments, s is 0. In certain embodiments, s is an integer between 1 and 100. In some embodiments, s is an integer between 10 and 100, inclusive. In some embodiments, s is an integer between 10 and 50, inclusive. In some embodiments, s is an integer between 10 and 25, inclusive. In some embodiments, s is an integer between 1 and 10, inclusive. In certain embodiments, q is an integer between 1 and 100, inclusive. In some embodiments, q is an integer between 10 and 100, inclusive. In some embodiments, q is an integer between 50 and 75, between 75 and 100, between 100 and 125, between 125 and 150, between 150 and 175, or between 175 and 200, inclusive. In certain embodiments, q is 100. In certain embodiments, q is 101. In certain embodiments, both q and s are 0. In certain embodiments, exactly one of q and s is 0. In certain embodiments, q and s are the same. In certain embodiments, q and s are different. The sum of q, r, and s is at least 1.

In certain embodiments, the compound of Formula (I) is of formula:

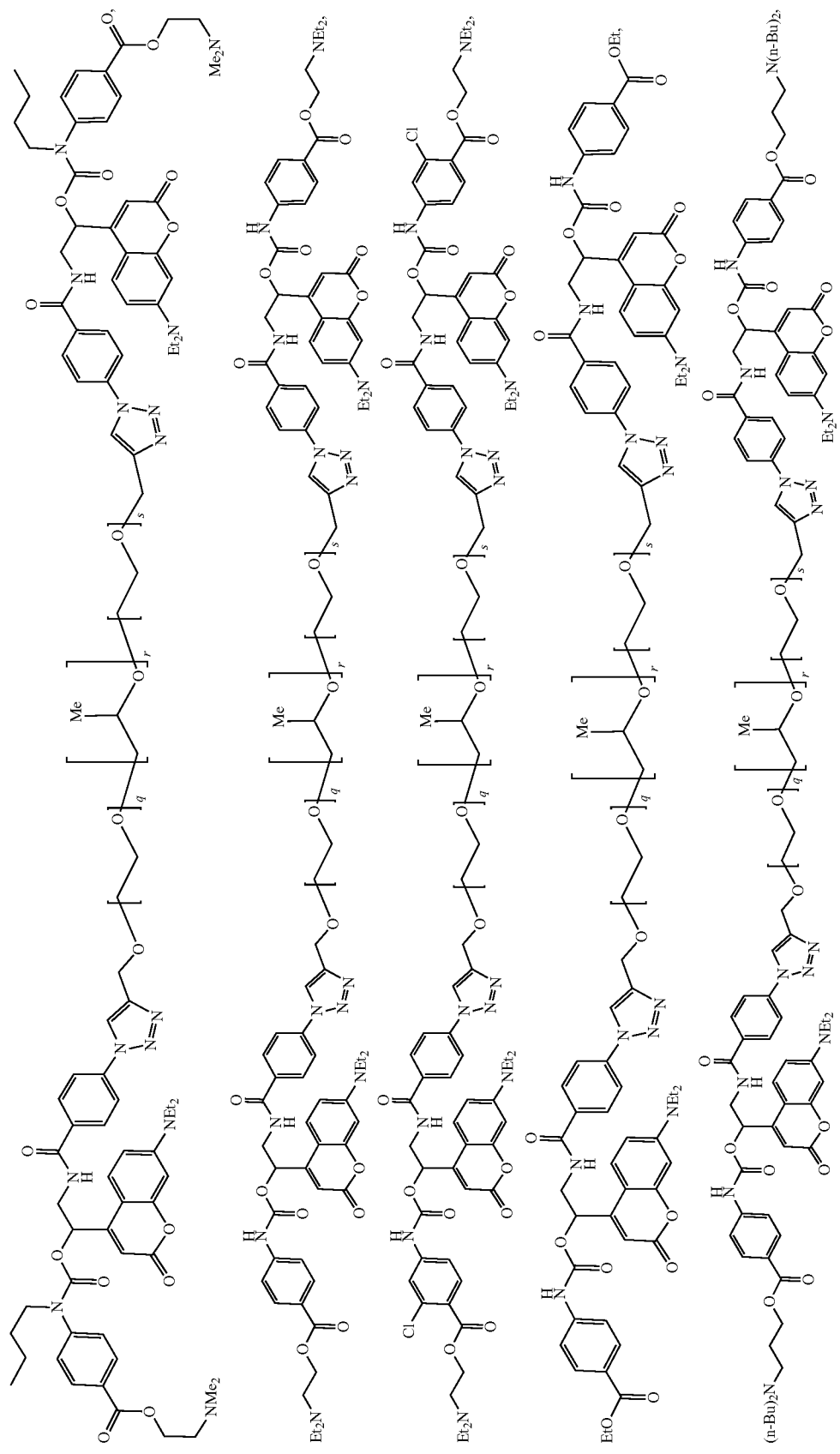

-continued
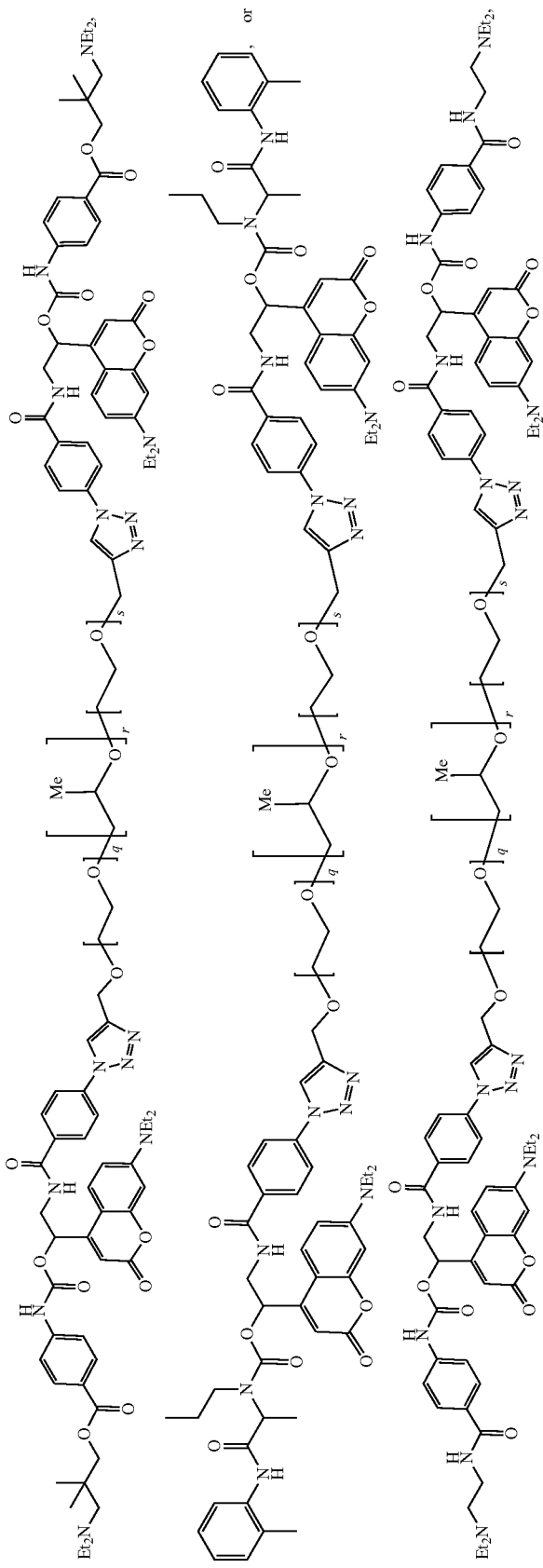

wherein q, r, and s are as defined herein.

In certain embodiments, the compound of Formula (I) is of formula:

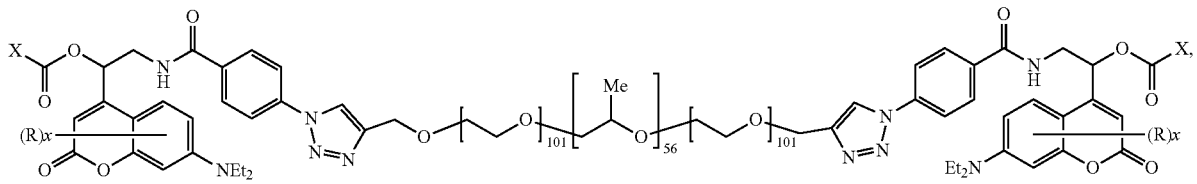

or a pharmaceutically acceptable salt, co-crystal, tautomer, stereoisomer, solvate, hydrate, polymorph, or an isotopically enriched derivative thereof.

In certain embodiments, the compound of Formula (I) is of formula:

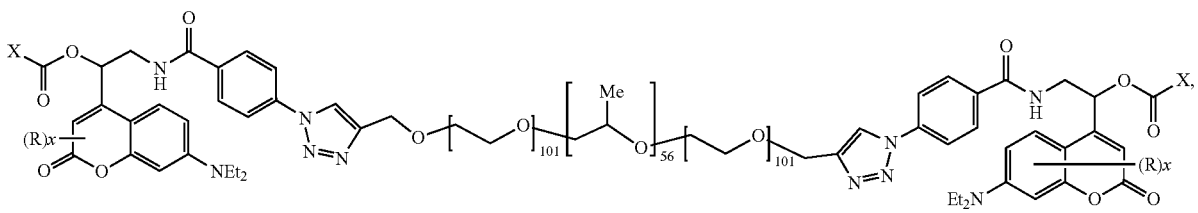

or a pharmaceutically acceptable salt thereof.

In certain embodiments, the compound of Formula (I) is of formula:

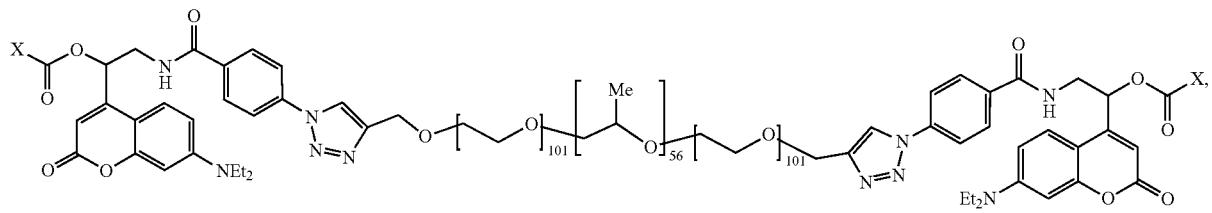

or a pharmaceutically acceptable salt, co-crystal, tautomer, stereoisomer, solvate, hydrate, polymorph, or an isotopically enriched derivative thereof.

In certain embodiments, the compound of Formula (I) is of formula:

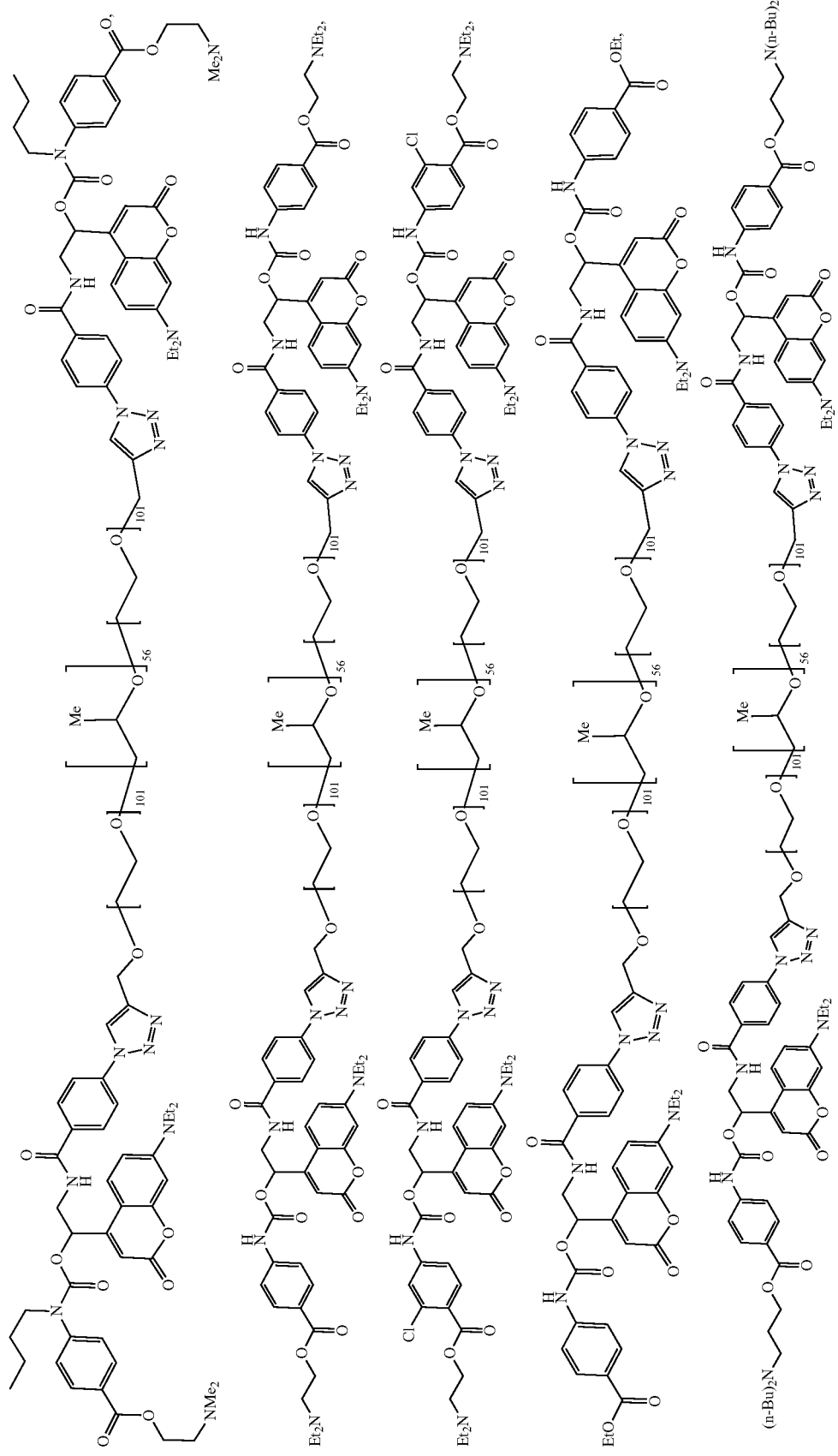

-continued
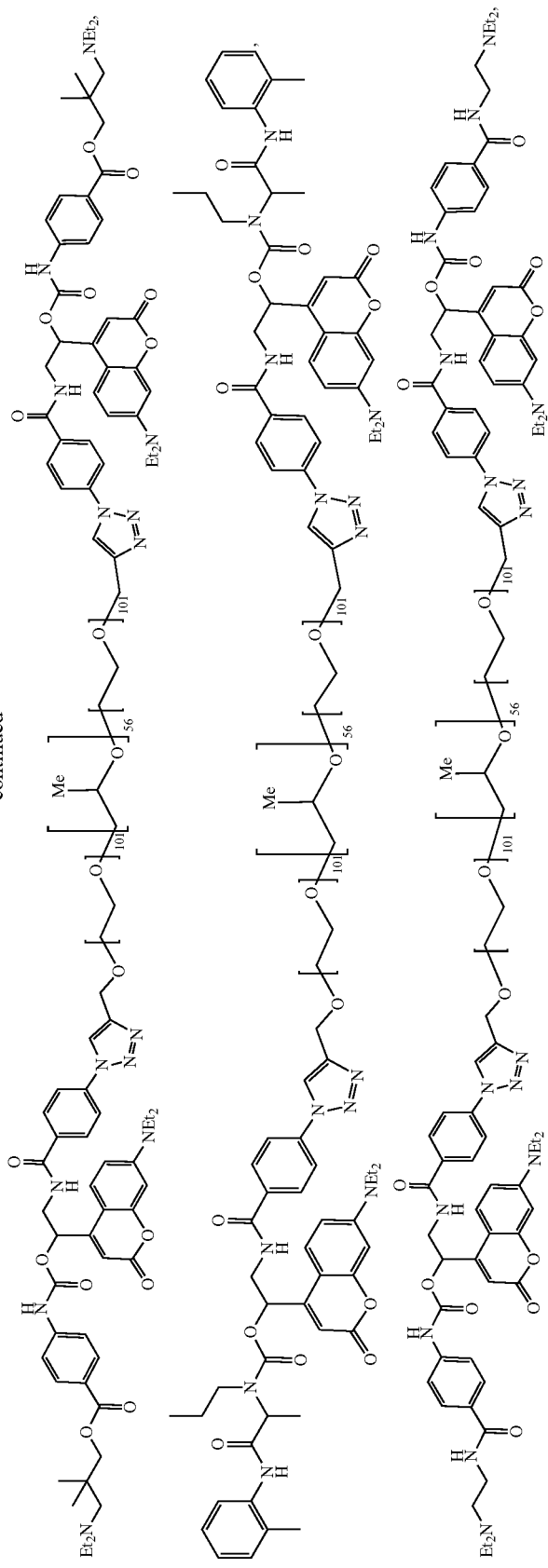

or a pharmaceutically acceptable salt, co-crystal, tautomer, stereoisomer, solvate, hydrate, polymorph, or an isotopically enriched derivative thereof.

In certain embodiments, the compound of Formula (I) is of formula:

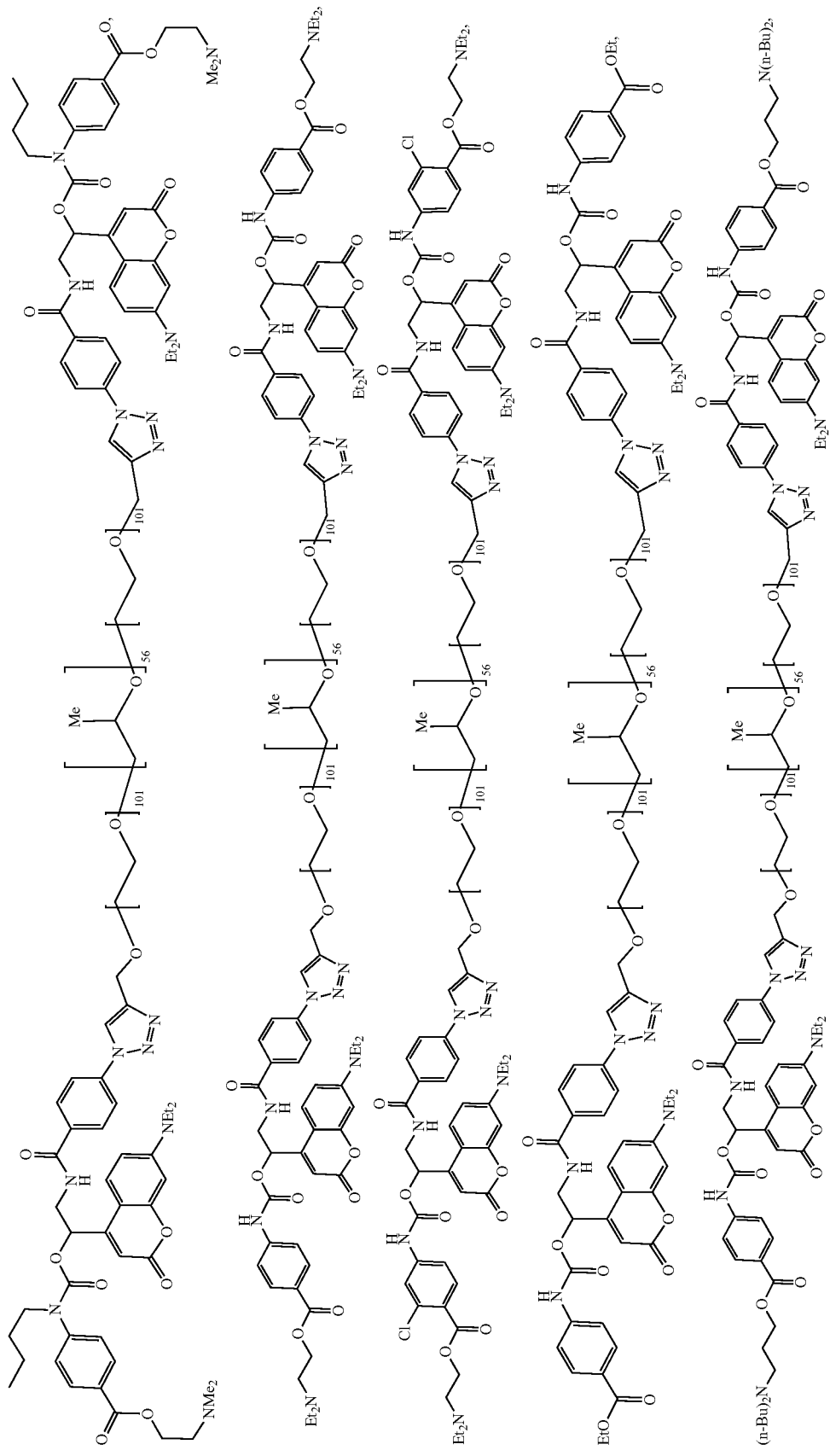

-continued
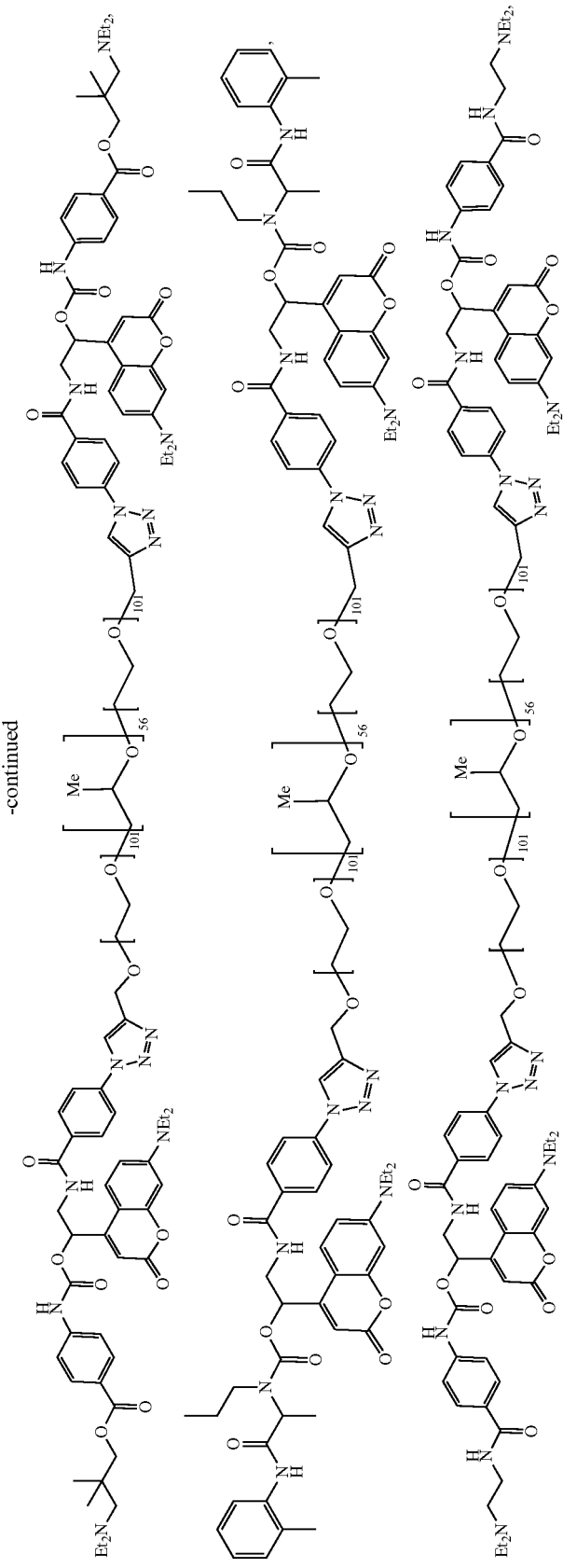

or a pharmaceutically acceptable salt thereof.

In certain embodiments, the compound of Formula (I) is a compound provided in any one of the Examples below. In certain embodiments, the compound of Formula (I) is a compound provided in Examples 1 and 2 below. In certain embodiments, the compound of Formula (I) is a compound provided in Example 1 below.

In certain embodiments, each instance of L is independently a photocleavable linker; and the bonds between each instance of L and each instance of X are cleaved upon illumination with light at an absorption wavelength between approximately 200 nm to 500 nm. In certain embodiments, the light absorption wavelength is about 300 nm to about 550 nm. In certain embodiments, both instances of L are each a photocleavable linker. In certain embodiments, the light absorption wavelength is about 350 nm to about 530 nm. In certain embodiments, the light absorption wavelength is about 450 nm to 475 nm. In certain embodiments, the light absorption wavelength is about 400 nm. In certain embodiments, the light absorption wavelength is about 200 nm to about 550 nm, about 200 nm to about 250 nm, about 250 nm to about 300 nm, about 300 nm to about 350 nm, about 200 nm to about 300 nm, about 300 nm to about 400 nm, about 300 nm to about 500 nm, about 350 nm to about 400 nm, about 400 nm to about 500 nm, about 400 nm to about 450 nm, about 450 nm to about 500 nm, about 550 nm to about 600 nm, or about 500 nm to about 600 nm. In certain embodiments, the light absorption wavelength is about 200 nm, about 300 nm, about 400 nm, about 500 nm, or about 600 nm. In certain embodiments, the light is a LED. In certain embodiments, the light is a blue LED. In certain embodiments, the light is a yellow LED. In certain embodiments, the light is a yellow-green LED. In certain embodiments, the light is a green LED. In certain embodiments, the light is an orange LED.

In certain embodiments, both instances of the active local anesthetic compound X are released upon the illumination with light. In certain embodiments, all instances of the active local anesthetic compound X are released upon the illumination with light. In certain embodiments, the bonds between each instance of L and each instance of X are cleaved upon illumination with light from a light emitting diode (LED). In certain embodiments, the bonds between each instance of L and each instance of X are cleaved upon illumination with light from a blue LED. In certain embodiments, the bonds between each instance of L and both instances of X are cleaved upon illumination with light from the same color of LED. In certain embodiments, the bonds between each instance of L and both instances of X are cleaved upon illumination with light from a blue LED. In certain embodiments, the bonds between each instance of L and each instance of X are cleaved upon illumination with light from a different color of LED.

The compounds and compositions described herein may be useful in treating and/or preventing diseases and/or conditions in a subject in need thereof, for example, in treating pain, such as pain associated with an infectious disease, pain associated with an ear disease, pain associated with a medical procedure (e.g., dental procedure, surgery), pain associated with trauma (e.g., injury), and/or sustained pain.

Pharmaceutical Compositions, Kits, and Administration

The present disclosure also provides pharmaceutical compositions comprising a compound described herein and optionally a pharmaceutically acceptable excipient. In certain embodiments, a compound described herein is a compound of Formula (I), or a pharmaceutically acceptable salt thereof, and a pharmaceutically acceptable excipient.

In certain embodiments, the composition is in the form of a particle. In certain embodiments, the composition is in the form of a nanoparticle or a microparticle. In certain embodiments, the composition is encapsulated in the form of a particle. In certain embodiments, the particle encapsulates the composition, as described herein. In certain embodiments, provided are compositions in the form of a plurality of particles. In certain embodiments, the particle is a nanoparticle or a microparticle. In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for treating and/or preventing a disease and/or condition, for example, in treating pain, such as pain associated with an infectious disease, pain associated with an ear disease, pain associated with a medical procedure (e.g., dental procedure, surgery), pain associated with trauma (e.g., injury), and/or sustained pain. In certain embodiments, the condition is pain. In certain embodiments, the condition is pain associated with an infectious disease (e.g. infection by a virus, bacteria, microbe). In certain embodiments, the condition is pain associated with an ear disease (e.g., otitis media). In certain embodiments, the disease is an infectious disease (e.g. infection by a virus, bacteria, microbe). In certain embodiments, the condition is pain associated with a medical procedure, for example, surgery (e.g., dental surgery). In certain embodiments, the medical procedure is a dental medical procedure. In certain embodiments, the medical procedure is surgery. In certain embodiments, the surgery is dental surgery. In certain embodiments, the surgery is facial surgery. In certain embodiments, the surgery is cosmetic surgery. In certain embodiments, the condition is pain associated with trauma (e.g., injury). In certain embodiments, the condition is pain associated with an injury. In certain embodiments, the painful condition is inflammatory pain. In certain embodiments, the painful condition (e.g., inflammatory pain) is associated with an infectious disease and/or ear disease. In certain embodiments, the pain is chronic pain related to one or more of the following conditions, including, but not limited to, lower back pain, arthritis (e.g., osteoarthritis), headaches, multiple sclerosis, fibromyalgia, shingles, cancer, surgery, or other medical procedures, amputation; surgery, invasive medical procedures, toxins, burns, infection, and nerve damage (e.g., neuropathy). In certain embodiments, the pain is pain associated with psychological factors, which is psychogenic pain related to one or more of the following conditions including headaches, muscle pains, back pains, or stomach pains. In certain embodiments, the pain is neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, and/or visceral pain. In certain embodiments, the disease is an inflammatory disease. In certain embodiments, the disease is an infectious disease. In certain embodiments, the disease is an infectious disease. In certain embodiments, the disease is a bacterial infectious disease. In certain embodiments, the disease is a viral infectious disease. In certain embodiments, the disease is an ear disease (e.g, otitis media).

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 pg and 1 pg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, as well as improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease and/or condition (e.g., inflammatory disease, infectious disease, pain). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, pain-relieving agents, and a combination thereof. In certain embodiments, the additional pharmaceutical agent is an anti-inflammatory agent. In certain embodiments, the additional pharmaceutical agent is a pain-relieving agent.

Kits

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease and/or condition (e.g., inflammatory disease, infectious disease, pain) in a subject in need thereof. In certain embodiments, the kits are useful for preventing a disease and/or condition (e.g., inflammatory disease, infectious disease, pain) in a subject in need thereof. In certain embodiments, the kits comprise a container, a composition of a compound described herein, and instructions for administering the composition or pharmaceutical composition thereof to a subject in need thereof. In certain embodiments, the kits comprise a container, a composition of a compound described herein, and instructions for administering the composition or pharmaceutical composition thereof to a subject in need thereof, and light of an absorption wavelength sufficient to cleave the bonds between each instance of L and each instance of X upon illumination with the light (e.g., light between approximately 200 nm to 500 nm). In certain embodiments, the light is a LED. In certain embodiments, the light is a blue LED. In certain embodiments, the light is a yellow LED. In certain embodiments, the light is a yellow-green LED. In certain embodiments, the light is a green LED. In certain embodiments, the light is an orange LED. In certain embodiments, the light absorption wavelength is about 300 nm to about 550 nm. In certain embodiments, the light absorption wavelength is about 350 nm to about 530 nm. In certain embodiments, the light absorption wavelength is about 450 nm to 475 nm. In certain embodiments, the light absorption wavelength is about 400 nm. In certain embodiments, the light absorption wavelength is about 200 nm to about 550 nm, about 200 nm to about 250 nm, about 250 nm to about 300 nm, about 300 nm to about 350 nm, about 200 nm to about 300 nm, about 300 nm to about 400 nm, about 300 nm to about 500 nm, about 350 nm to about 400 nm, about 400 nm to about 500 nm, about 400 nm to about 450 nm, about 450 nm to about 500 nm, about 550 nm to about 600 nm, or about 500 nm to about 600 nm.

In certain embodiments, the light absorption wavelength is about 200 nm, about 300 nm, about 400 nm, about 500 nm, or about 600 nm.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease and/or condition (e.g., inflammatory disease, infectious disease, pain) in a subject in need thereof. In certain embodiments, the kits and instructions provide for preventing a disease and/or condition (e.g., inflammatory disease, infectious disease, pain) in a subject in need thereof. A kit described herein may include one or more additional pharmaceutical agents described herein as a separate composition. In certain embodiments, a kit described herein further includes a dropper, syringe, or catheter. In certain embodiments, a kit described herein further includes a syringe.

Methods of Treatment and Uses

The present disclosure provides methods of treating a disease and/or condition in a subject in need thereof, the method comprising administering to the subject a therapeutically effective amount of a composition of a compound (e.g., a compound of Formula (I)) described herein, and optionally further comprising illumination of the composition or the pharmaceutical composition with light of an absorption wavelength sufficient to cleave the bonds between each instance of L and each instance of X upon illumination with the light (e.g., light between approximately 200 nm to 500 nm). In certain embodiments, the composition is illuminated with light that is a LED. In certain embodiments, the light is a blue LED. In certain embodiments, the light is a yellow LED. In certain embodiments, the light is a yellow-green LED. In certain embodiments, the light is a green LED. In certain embodiments, the light is an orange LED. In certain embodiments, the light absorption wavelength is about 300 nm to about 550 nm. In certain embodiments, the light absorption wavelength is about 350 nm to about 530 nm. In certain embodiments, the light absorption wavelength is about 450 nm to 475 nm. In certain embodiments, the light absorption wavelength is about 400 nm. In certain embodiments, the light absorption wavelength is about 200 nm to about 550 nm, about 200 nm to about 250 nm, about 250 nm to about 300 nm, about 300 nm to about 350 nm, about 200 nm to about 300 nm, about 300 nm to about 400 nm, about 300 nm to about 500 nm, about 350 nm to about 400 nm, about 400 nm to about 500 nm, about 400 nm to about 450 nm, about 450 nm to about 500 nm, about 550 nm to about 600 nm, or about 500 nm to about 600 nm. In certain embodiments, the light absorption wavelength is about 200 nm, about 300 nm, about 400 nm, about 500 nm, or about 600 nm.

The present disclosure also provides a compound of Formula (I), or a pharmaceutically acceptable salt, co-crystal, tautomer, stereoisomer, solvate, hydrate, polymorph, an isotopically enriched derivative, or composition thereof, for use in the treatment of diseases and/or conditions, such as inflammatory disease, infectious disease, pain, in a subject in need thereof. The present disclosure also provides a composition comprising a compound of Formula (I), or a pharmaceutically acceptable salt, co-crystal, tautomer, stereoisomer, solvate, hydrate, polymorph, or an isotopically enriched derivative thereof, for use in the treatment of diseases, such as inflammatory disease, infectious disease, pain, in a subject in need thereof.

The present disclosure also provides uses of a compound of Formula (I), pharmaceutically acceptable salt, co-crystal, tautomer, stereoisomer, solvate, hydrate, polymorph, an isotopically enriched derivative, or composition thereof, in the manufacture of a medicament for the treatment and/or prevention of diseases and/or conditions, such as inflammatory disease, infectious disease, pain, in a subject in need thereof. In certain embodiments, provided are uses of compositions comprising a compound of Formula (I), pharmaceutically acceptable salt, co-crystal, tautomer, stereoisomer, solvate, hydrate, polymorph, or an isotopically enriched derivative thereof, for the treatment and/or prevention of diseases and/or conditions, such as inflammatory disease, infectious disease, pain, in a subject in need thereof. In certain embodiments, provided are uses of compositions comprising a compound of Formula (I), pharmaceutically acceptable salt, co-crystal, tautomer, stereoisomer, solvate, hydrate, polymorph, or an isotopically enriched derivative thereof, for the treatment and/or prevention of diseases and/or conditions, such as inflammatory disease, infectious disease, pain, in a subject in need thereof, comprising illumination of the composition or the pharmaceutical composition with light sufficient to cleave the bonds between each instance of L and each instance of X upon illumination with the light (e.g., light between approximately 200 nm to 500 nm). In certain embodiments, the composition is illuminated with light that is a LED. In certain embodiments, the light is a blue LED. In certain embodiments, the light is a yellow LED. In certain embodiments, the light is a yellow-green LED. In certain embodiments, the light is a green LED. In certain embodiments, the light is an orange LED. In certain embodiments, the light absorption wavelength is about 300 nm to about 550 nm. In certain embodiments, the light absorption wavelength is about 350 nm to about 530 nm. In certain embodiments, the light absorption wavelength is about 450 nm to 475 nm. In certain embodiments, the light absorption wavelength is about 400 nm. In certain embodiments, the light absorption wavelength is about 200 nm to about 550 nm, about 200 nm to about 250 nm, about 250 nm to about 300 nm, about 300 nm to about 350 nm, about 200 nm to about 300 nm, about 300 nm to about 400 nm, about 300 nm to about 500 nm, about 350 nm to about 400 nm, about 400 nm to about 500 nm, about 400 nm to about 450 nm, about 450 nm to about 500 nm, about 550 nm to about 600 nm, or about 500 nm to about 600 nm. In certain embodiments, the light absorption wavelength is about 200 nm, about 300 nm, about 400 nm, about 500 nm, or about 600 nm.

In certain embodiments, the compounds described herein are used in applications where the nerves of interest are relatively close to the body surface, e.g. dental applications. In certain embodiments, the disease and/or condition (e.g., inflammatory disease, infectious disease, pain) to be treated or prevented using the compounds and compositions described herein is pain associated with an infectious disease, pain associated with an ear disease, pain associated with a medical procedure (e.g., dental procedure, surgery), pain associated with trauma (e.g., injury), and/or sustained pain. In certain embodiments, the condition is pain. In certain embodiments, the condition is pain associated with an infectious disease (e.g. infection by a virus, bacteria, microbe). In certain embodiments, the condition is pain associated with an ear disease (e.g., otitis media). In certain embodiments, the disease is an infectious disease (e.g. infection by a virus, bacteria, microbe). In certain embodiments, the condition is pain associated with a medical procedure, for example, surgery (e.g., dental surgery). In certain embodiments, the medical procedure is a dental medical procedure. In certain embodiments, the medical procedure is surgery. In certain embodiments, the surgery is dental surgery. In certain embodiments, the surgery is facial surgery. In certain embodiments, the surgery is cosmetic surgery. In certain embodiments, the condition is pain associated with trauma (e.g., injury). In certain embodiments, the condition is pain associated with an injury. In certain embodiments, the painful condition is inflammatory pain. In certain embodiments, the painful condition (e.g., inflammatory pain) is associated with an infectious disease and/or ear disease. In certain embodiments, the pain is chronic pain related to one or more of the following conditions, including, but not limited to, lower back pain, arthritis (e.g., osteoarthritis), headaches, multiple sclerosis, fibromyalgia, shingles, cancer, surgery, or other medical procedures, amputation; surgery, invasive medical procedures, toxins, burns, infection, and nerve damage (e.g., neuropathy). In certain embodiments, the pain is pain associated with psychological factors, which is psychogenic pain related to one or more of the following conditions including headaches, muscle pains, back pains, or stomach pains. In certain embodiments, the pain is neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, and/or visceral pain. In certain embodiments, the disease is an inflammatory disease. In certain embodiments, the disease is an infectious disease. In certain embodiments, the disease is an infectious disease. In certain embodiments, the disease is a bacterial infectious disease. In certain embodiments, the disease is a viral infectious disease. In certain embodiments, the disease is an ear disease (e.g, otitis media). In certain embodiments, the method comprises sustained treatment of pain.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1. Synthesis of Exemplary Prodrug Compounds

Compounds of Formulas (I) may be prepared in view of the following synthetic schemes, and by using synthetic schemes and procedures recognized by one of ordinary skill in the art.

Unless otherwise noted, reagents and solvents were obtained from commercial suppliers and were used without further purification. $^1$H NMR spectra were recorded on 500 MHz (Varian AS600), and chemical shifts are reported in parts per million (ppm, δ) downfield from tetramethylsilane (TMS). Coupling constants (J) are reported in Hz. Spin multiplicities are described as s (singlet), br (broad singlet), d (doublet), t (triplet), q (quartet), and m (multiplet). Mass spectra were obtained on a Waters Micromass ZQ instrument. Preparative HPLC was performed on a Waters Sunfire C18 column (19 mm×50 mm, 5 µM) using a gradient of 15-95% methanol in water containing 0.05% trifluoroacetic acid (TFA) over 22 min (28 min run time) at a flow rate of 20 mL/min. Purities of assayed compounds were in all cases greater than 95%, as determined by reverse-phase HPLC analysis.

Compounds of Formula (I) may be prepared using the synthetic scheme2 shown below (Schemes 1 and 2) and procedures known by one of ordinary skill in the art.

Scheme 1. Synthetic route to P407-CM-T.

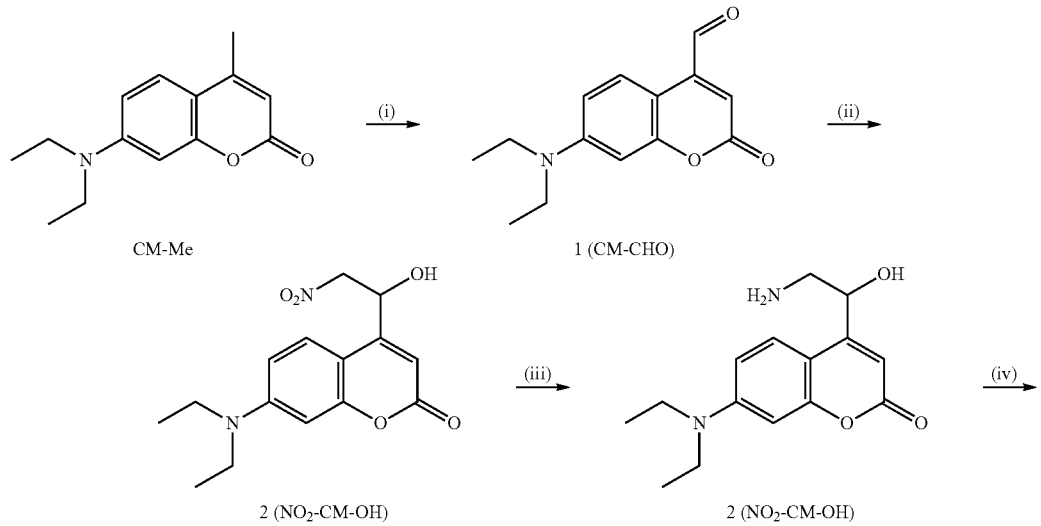

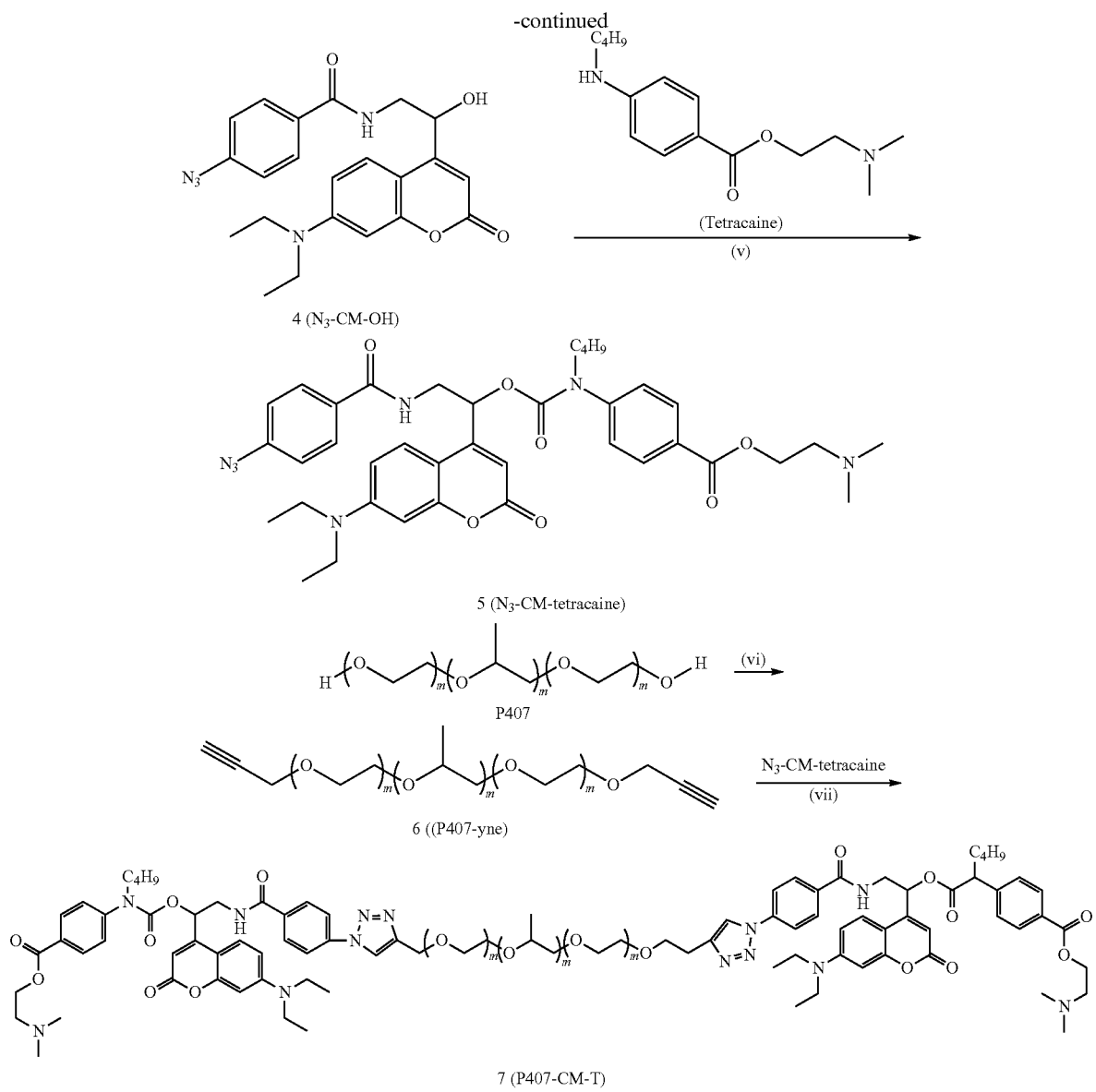

(i) SeO₂, 1,4-dioxane, reflux; (ii) CH₃NO₂, N, N, N'N'-tetramethylethylenediamine, THF; (iii) Zn, acetic acid; (iv) 4-azidobenzoic acid, DIC, DMAP, DCM; (v) tetracaine, triphosgene, DIPEA, DBU, DCM; (vi) sodium hydride, THF; (vii) Copper (II) sulfate pentahydrate, (+)- sodium L-ascorbate, methanol/H₂O.

Synthesis of Compound 1 (CM-CHO). 7-Diethylamino-4-methylcoumarin (2.31 g, 10 mmol) was dissolved in 1,4-dioxane (50 mL). Selenium dioxide (2.00 g, 18 mmol) was added. The mixture was refluxed overnight before filtered through celite. The filtrate was concentrated and purified by silica gel chromatography (dichloromethane: hexane 3:1) to give the product as a red crystal (860 mg, 35%). $^1$H NMR (CDCl₃, 400 MHz, ppm, δ) 9.95 (s, 1H), 8.21-8.19 (d, 1H), 6.60-6.57 (d, 1H), 6.46 (s, 1H), 6.37 (s, 1H), 3.40-3.34 (m, 4H), 1.18-1.14 (m, 6H). $^{13}$C NMR (CDCl₃, 100 MHz, ppm, δ) 192.39, 161.60, 157.15, 150.57, 143.68, 126.93, 117.27, 109.83, 104.06, 97.98, 45.04, 12.34. ESI-MS: m/z calculated for $C_{14}H_{16}NO_3$ [M+H]⁺: 246.1; observed: 246.1

Synthesis of Compound 2 (NO₂—CM-OH). Compound 1 (245 mg, 1.0 mmol) was dissolved in tetrahydrofuran (THF, 2 mL). In an ice-water bath, a solution of nitromethane (610 mg, 10 mmol) in THF (2 mL) was added dropwise. Then, a solution of N,N,N'N'-tetramethylethylenediamine (35 mg, 0.3 mmol) in THF (2 mL) was added dropwise. The reaction mixture was allowed to warm up to ambient temperature and stirred for another 4 h. The solvent was removed by a rotatory evaporator. The residue was re-dissolved in a small amount of dichloromethane and purified by silica gel chromatography (dichloromethane:ethyl acetate 10:1) to give the product as an orange solid (220 mg, 76%). $^1$H NMR (CDCl₃, 400 MHz, ppm, δ) 7.42-7.40 (d, 1H), 6.64-6.62 (dd, 1H), 6.54 (s, 1H), 6.38 (s, 1H), 5.82-5.80 (m, 1H), 4.66-4.59 (m, 2H), 3.47-3.41 (m, 4H), 3.18-3.17 (d, 1H), 1.24-1.21 (t, 6H). $^{13}$C NMR (CDCl₃, 100 MHz, ppm, δ) 161.97, 156.50, 151.84, 150.84, 123.95, 109.12, 106.64, 104.96, 98.13, 79.70, 67.06, 44.82, 12.41. ESI-MS: m/z calculated for $C_{15}H_{19}N_2O_5$ [M+H]⁺: 307.1; observed: 307.1

Synthesis of Compound 3 (NH₂—CM-OH). Compound 2 (920 mg, 3.2 mmol) was suspended in acetic acid (15 mL). The suspension was placed in an ice-water bath. Then zinc powder (1.35 g, 20.8 mmol) was added. After 30 min, the reaction mixture was allowed to warm up to ambient temperature and stirred for another 2 h. The solid was removed by filtration. The filtrate was neutralized by saturated $Na_2CO_3$ aqueous solution. The mixture was extracted with dichloromethane (200 mL) and then washed with saturated $Na_2CO_3$ aqueous solution (100 mL) and saturated NaCl aqueous solution (100 mL×2). The organic phase was dried by anhydrous $Na_2SO_4$ and concentrated by vacuum. The residue was purified by silica gel chromatography (dichloromethane:methanol 5:1) to give the product as a yellow solid (550 mg, 65%). $^1$H NMR (CDCl$_3$, 400 MHz, ppm, δ) 7.38-7.36 (d, 1H), 6.53-6.52 (dd, 1H), 6.43 (s, 1H), 6.30 (s, 1H), 5.03-5.01 (m, 1H), 3.44-3.34 (m, 6H), 3.16-3.13 (m, 1H), 2.87-2.85 (m, 1H), 1.17-1.15 (t, 6H). $^{13}$C NMR (CDCl$_3$, 100 MHz, ppm, δ) 162.65, 156.46, 156.30, 150.36, 124.75, 108.66, 106.12, 105.54, 97.75, 68.86, 46.77, 44.47, 44.65, 12.43. ESI-MS: m/z calculated for $C_{15}H_{21}N_2O_3$ [M+H]$^+$: 277.2; observed: 277.1.

Synthesis of Compound 4 (N$_3$—CM-OH). To a suspension of 4-azidobenzoic acid (65 mg, 0.40 mmol) in dichloromethane (2 mL) in an ice-water bath, triethylamine (80 mg, 0.8 mmol) was added, followed by HATU (170 mg, 0.44 mmol). After 5 min, Compound 3 (100 mg, 0.36 mmol) in dichloromethane (5 mL) was added. The mixture was then stirred for 2 h at ambient temperature. Dichloromethane (80 mL) was used to dilute the reaction mixture, which was then washed by saturated NaCl aqueous solution (100 mL×3). The organic phase was dried by anhydrous $Na_2SO_4$ and concentrated using a rotatory evaporator. The residue was purified by silica gel chromatography (dichloromethane:methanol 20:1) to give the product as a yellow solid (130 mg, 86%). $^1$H NMR (CDCl$_3$, 500 MHz, ppm, δ) 7.83-7.82 (d, 2H), 7.75-7.73 (d, 1H), 7.07-7.05 (d, 2H), 7.05-7.03 (m, 1H), 6.67-6.65 (m, 1H), 6.47-6.46 (d, 1H), 6.37 (s, 1H), 5.32-5.30 (m, 1H), 4.20-4.15 (m, 1H), 3.88-3.86 (d, 1H), 3.44-3.39 (m, 4H), 3.31-3.26 (m, 1H), 1.23-1.20 (t, 6H). $^{13}$C NMR (CDCl$_3$, 125 MHz, ppm, δ) 167.94, 162.83, 156.31, 156.10, 150.88, 143.82, 129.94, 128.90, 125.05, 119.09, 109.06, 106.02, 105.33, 97.69, 69.15, 46.74, 44.75, 12.46. ESI-MS: m/z calculated for $C_{22}H_{24}N_5O_4$ [M+H]$^+$: 422.2; observed: 422.2.

Synthesis of Compound 5 (N3-CM-tetracaine). To a solution of triphosgene (73 mg, 0.25 mmol) in anhydrous dichloromethane (2 mL) in an ice-water bath, a solution of tetracaine (190 mg, 0.72 mmol) and N,N-diisopropylethylamine (100 mg, 0.77 mmol) in dichloromethane (5 mL) was added dropwise. The reaction mixture was stirred for 1 h at ambient temperature. The resulted solution was withdrawn in a syringe and then added into a solution of Compound 4 (120 mg, 0.28 mmol) and 1,8-diazabicyclo[5.4.0]undec-7-ene (250 mg, 1.67 mmol) in dichloromethane (5 mL). The reaction mixture then was stirred for 7 days. Dichloromethane (100 mL) was used to dilute the reaction mixture. The solution was washed by saturated NaCl aqueous solution (100 mL×3). The organic phase was dried by anhydrous $Na_2SO_4$ and concentrated by vacuum. The residue was re-dissolved in a small amount of dichloromethane and purified by silica gel chromatography (dichloromethane:methanol 10:1) to give the product as a light-yellow solid (38 mg, 19%). $^1$H NMR (CDCl$_3$, 500 MHz, ppm, δ) 8.07-8.05 (d, 2H), 7.77-7.75 (d, 2H), 7.73-7.72 (d, 1H), 7.30-7.28 (d, 2H), 7.08-7.06 (d, 2H), 6.63-6.61 (dd, 1H), 6.45 (s, 1H), 6.25-6.23 (m, 1H), 6.80-5.70 (m, 1H), 4.54-4.52 (t, 2H), 3.94-3.64 (m, 4H), 3.41-3.37 (m, 4H), 3.08-3.05 (m, 2H), 2.60 (s, 6H), 1.48-1.26 (m, 4H), 1.20-1.17 (t, 3H), 0.84-0.82 (t, 3H). $^{13}$C NMR (CDCl$_3$, 125 MHz, ppm, δ) 166.97, 165.53, 162.46, 156.37, 153.90, 152.99, 150.90, 145.78, 143.60, 130.91, 130.15, 128.92, 127.14, 125.38, 119.05, 109.37, 105.69, 104.62, 97.55, 71.53, 65.84, 60.48, 57.29, 50.19, 44.75, 30.22, 19.78, 15.27, 13.65, 13.41. ESI-MS: m/z calculated for $C_{38}H_{46}N_7O_7$ [M+H]$^+$: 712.3; observed: 712.3.

Synthesis of Compound 6 (P407-yne). P407 (1.2 g) was dissolved in anhydrous THF (10 mL), then NaH (24 mg, 1 mmol) was added at 0° C. The mixture was stirred for 2 h. Propargyl bromide (100 uL 80 wt % in toluene) was added dropwise. The reaction was stirred overnight. A few drops of water were added dropwise to quench the reaction. Then, the mixture was pass through a short silica gel column (dichloromethane:methanol 2:1). The solution was concentrated and precipitated into cold diethyl ether. The product was collected by filtration as an off-white solid in 90% yield. $^1$H NMR (CDCl$_3$, 500 MHz, ppm, δ) 4.21 (m, 4H), 3.77-3.36 (m, 1050H), 2.45 (m, 2H), 1.16-1.12 (m, 180H). GPC: $M_n$=12.6 kg/mol, Đ=1.40.

Synthesis of Compound 7 (P407-CM-T). Copper (II) sulfate pentahydrate (10 mg, 0.06 mmol) was dissolved in water (0.5 mL), then (+)-sodium L-ascorbate (20 mg, 0.1 mmol) was added. After 5 min, the mixture was added to a methanol solution (10 mL) containing Compound 6 (P407-yne, 200 mg, 0.013 mmol) and Compound 5 (N$_3$—CM-tetracaine, 40 mg, 0.056 mmol). After 12 h, the mixture was diluted by dichloromethane (100 mL) and washed with saturated NaCl aqueous solution (100 mL×3). The organic phase was dried by anhydrous $Na_2SO_4$ and concentrated by vacuum. The residue was purified by silica gel chromatography (dichloromethane:methanol 8:1). The collected solution was concentrated by a rotatory evaporator and precipitated in cold ether. The product was collected by filtration as a light-yellow solid (180, 85%). $^1$H NMR (CDCl$_3$, 400 MHz, ppm, δ) 8.23-8.24 (m, 2H), 8.15-8.13 (m, 4H), 8.04-8.03 (m, 4H), 7.89-7.87 (m, 6H), 7.35-7.34 (m, 4H), 6.70-6.68 (m, 2H), 6.49-6.48 (m, 2H), 6.31-6.29 (m, 2H), 5.92-5.81 (m, 2H), 5.59-5.57 (m, 2H), 4.79-4.68 (m, 4H), 4.25-3.20 (m, 1060H), 1.58-0.82 (m, 190H). GPC:$M_n$=13.6 kg/mol, Đ=1.41.

Scheme 2. Synthetic route to CM-T.

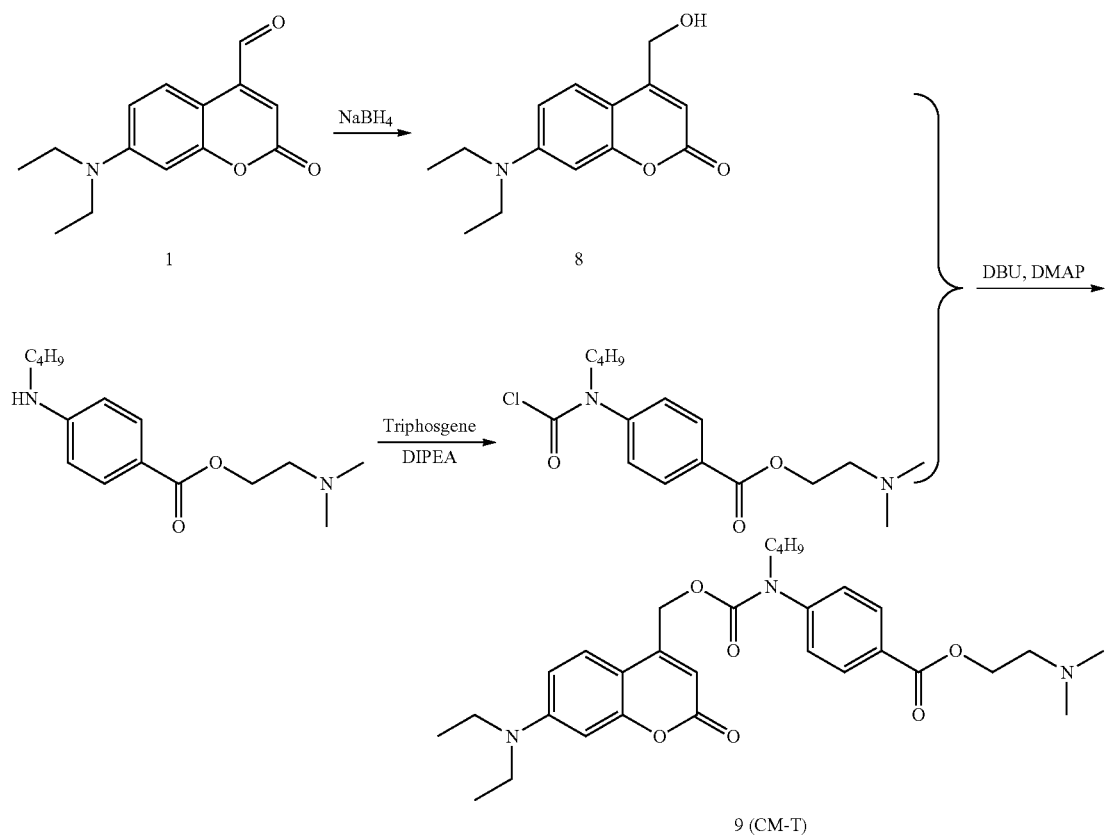

9 (CM-T)

Synthesis of Compound 8 (CM-OH). Compound 1 (350 mg, 1.43 mmol) was dissolved in methanol (5 mL). Sodium borohydride (170 mg, 4.50 mmol) was added slowly into the above solution in an ice-water bath. After 2 h, water (1 mL) was added to quench the reaction. Then, the mixture was diluted with dichloromethane (100 mL), followed by washed with saturated NaCl aqueous solution (100 mL×3). The organic phase was dried by anhydrous $Na_2SO_4$ and concentrated by vacuum. The residue was purified by silica gel chromatography (dichloromethane:ethyl acetate 5:1) to give the product as a yellow solid (250 mg, 71%). $^1H$ NMR (CDCl$_3$, 500 MHz, ppm, δ) 7.33-7.31 (d, 1H), 6.58-6.57 (dd, 1H), 6.51-6.50 (d, 1H), 6.27 (s, 1H), 4.84 (s, 2H), 3.43-3.39 (q, 4H), 1.23-1.20 (t, 6H). $^{13}C$ NMR (CDCl$_3$, 125 MHz, ppm, δ) 162.52, 156.17, 154.59, 150.49, 124.36, 108.53, 106.29, 105.48, 97.77, 60.99, 44.72, 12.45. ESI-MS: m/z calculated for $C_{14}H_{18}NO_3$ [M+H]$^+$: 248.1; observed: 248.1

Synthesis of Compound 9 (CM-T). To a solution of triphosgene (36 mg, 0.12 mmol) in anhydrous dichloromethane (2 mL) in an ice-water bath, a solution of tetracaine (90 mg, 0.34 mmol) and triethylamine (50 mg, 0.50 mmol) in dichloromethane (5 mL) was added dropwise. The reaction mixture was stirred for 1 h at ambient temperature. The resulted solution was withdrawn in a syringe and then added into a solution of Compound 8 (65 mg, 0.26 mmol) and triethylamine (120 mg, 1.2 mmol) in dichloromethane (5 mL). After 24 h, the reaction mixture was diluted by dichloromethane (100 mL) and washed by saturated NaCl aqueous solution (100 mL×3). The organic phase was dried by anhydrous $Na_2SO_4$ and concentrated by vacuum. The residue was purified by silica gel chromatography (dichloromethane:methanol 20:1) to give the product as a yellow solid (60 mg, 45%). $^1H$ NMR (CDCl$_3$, 500 MHz, ppm, δ) 8.07-8.05 (d, 2H), 7.32-7.30 (d, 2H), 7.24-7.22 (d, 1H), 8.54-8.51 (dd, 1H), 6.49-6.48 (d, 1H), 5.91 (m, 1H), 5.25 (s, 2H), 4.44-4.41 (t, 2H), 3.76-3.72 (t, 2H), 3.42-3.37 (q, 4H), 2.73-2.70 (t, 2H), 2.33 (s, 6H), 1.56-1.50 (m, 2H), 1.34-1.28 (m, 2H), 1.21-1.18 (t, 6H), 0.90-0.86 (t, 3H)$^{13}C$ NMR (CDCl$_3$, 125 MHz, ppm, δ) 165.80, 161.83, 159.19, 154.18, 150.61, 149.91, 131.63, 130.68, 128.70, 124.36, 108.56, 106.08, 105.91, 97.77, 63.05, 62.79, 57.76, 50.29, 45.78, 44.73, 30.36, 29.69, 19.84, 13.71, 12.42. ESI-MS: m/z calculated for $C_{30}H_{40}N_3O_6$ [M+H]$^+$: 538.3; observed: 538.3.

Figure 1B:
Figure 1C:
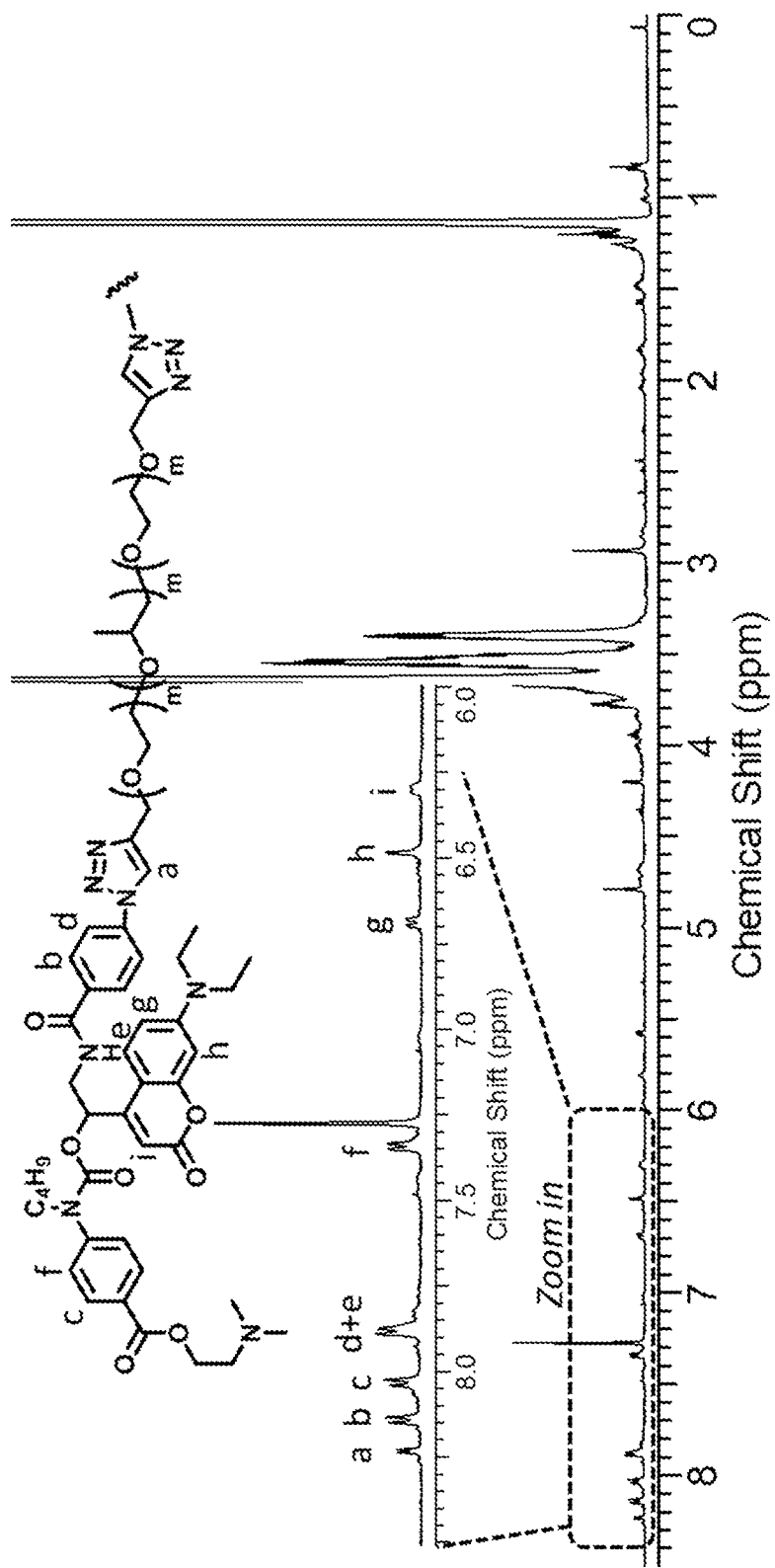
Figure 15:
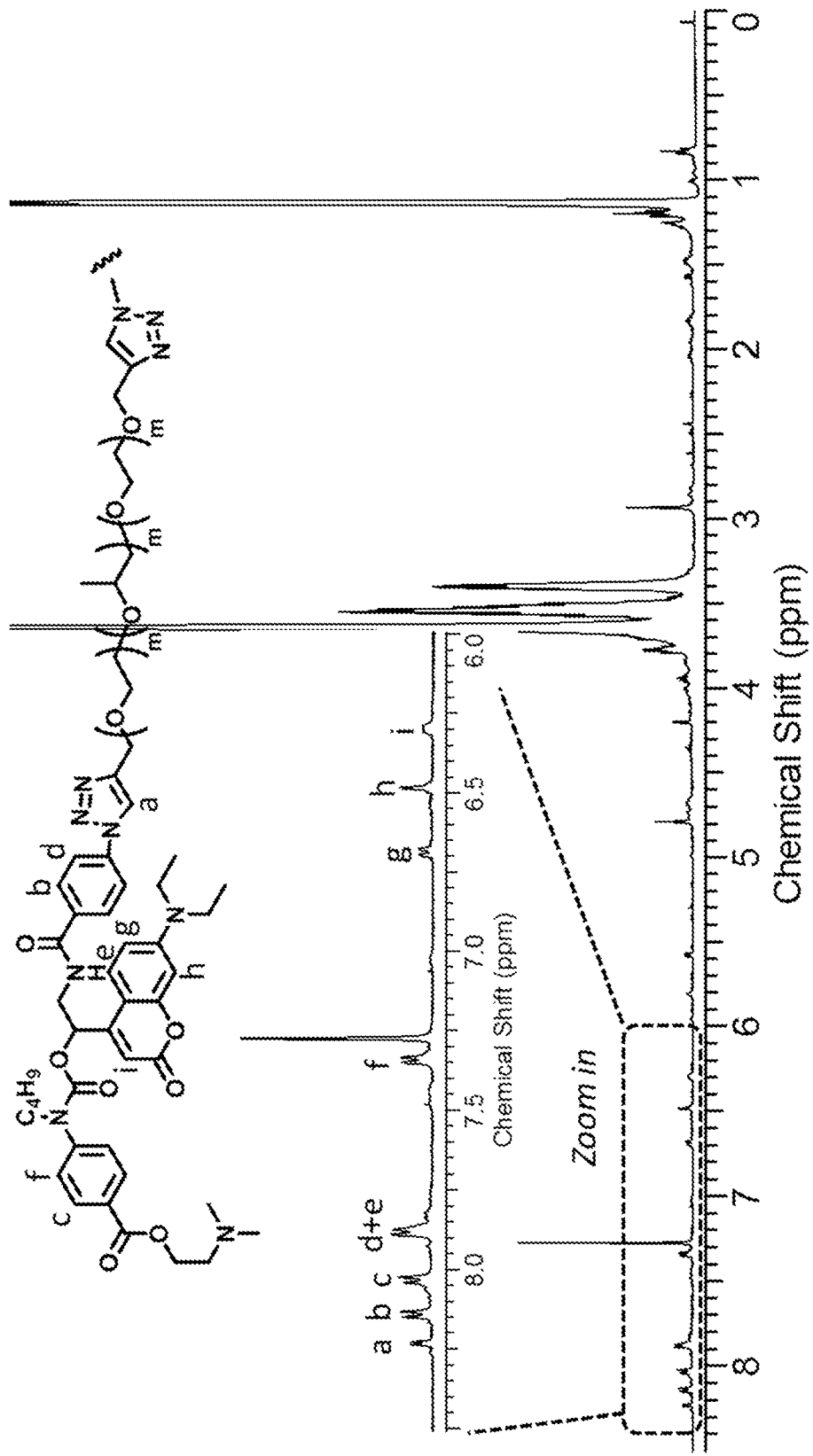
FIG. 15 shows the $^1$H NMR spectrum of compound 7 (P407-CM-T) (shown in FIG. 7).
Figure 16:
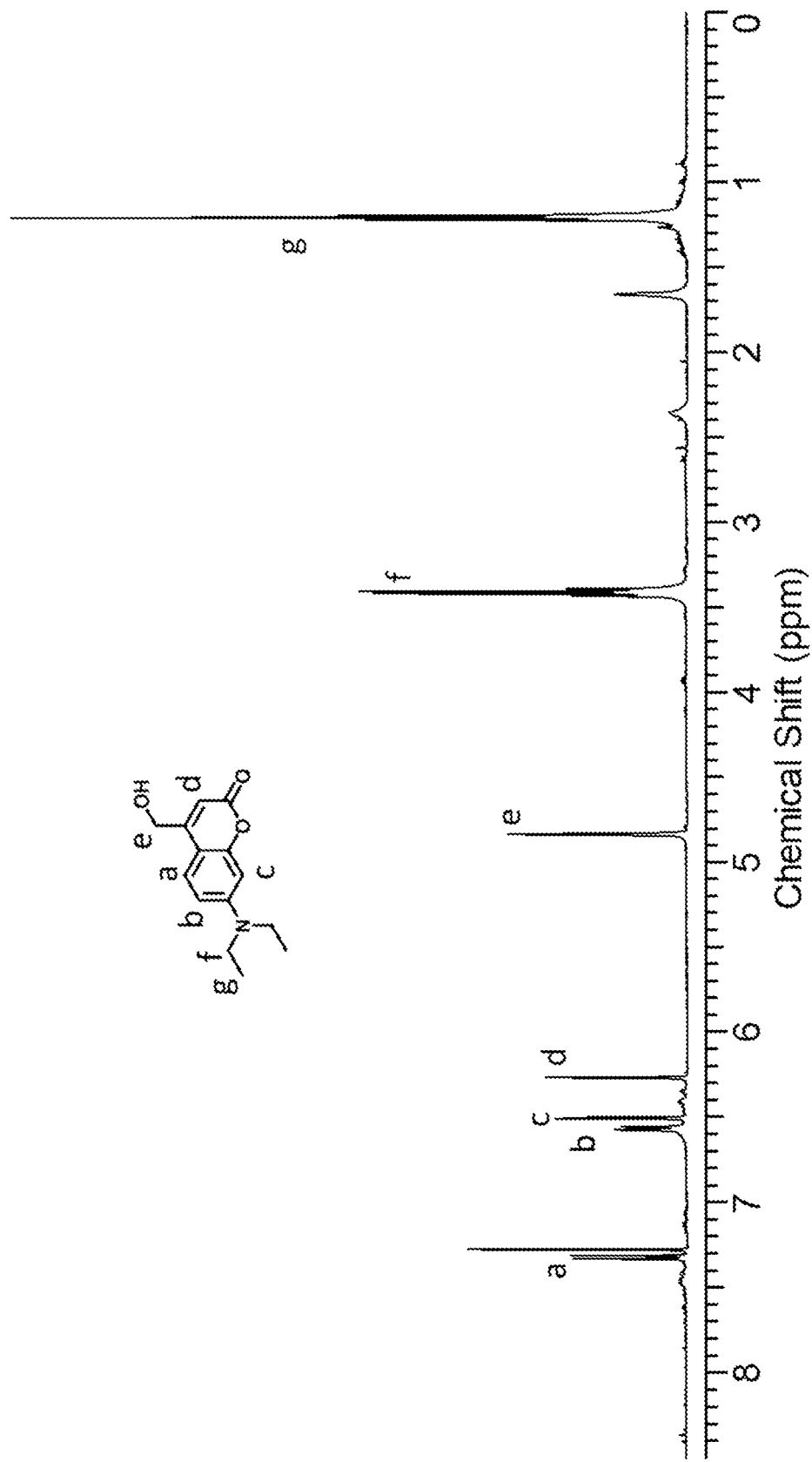
FIG. 16 shows the $^1$H NMR spectrum of compound 8 (shown in FIG. 8).
Figure 17:
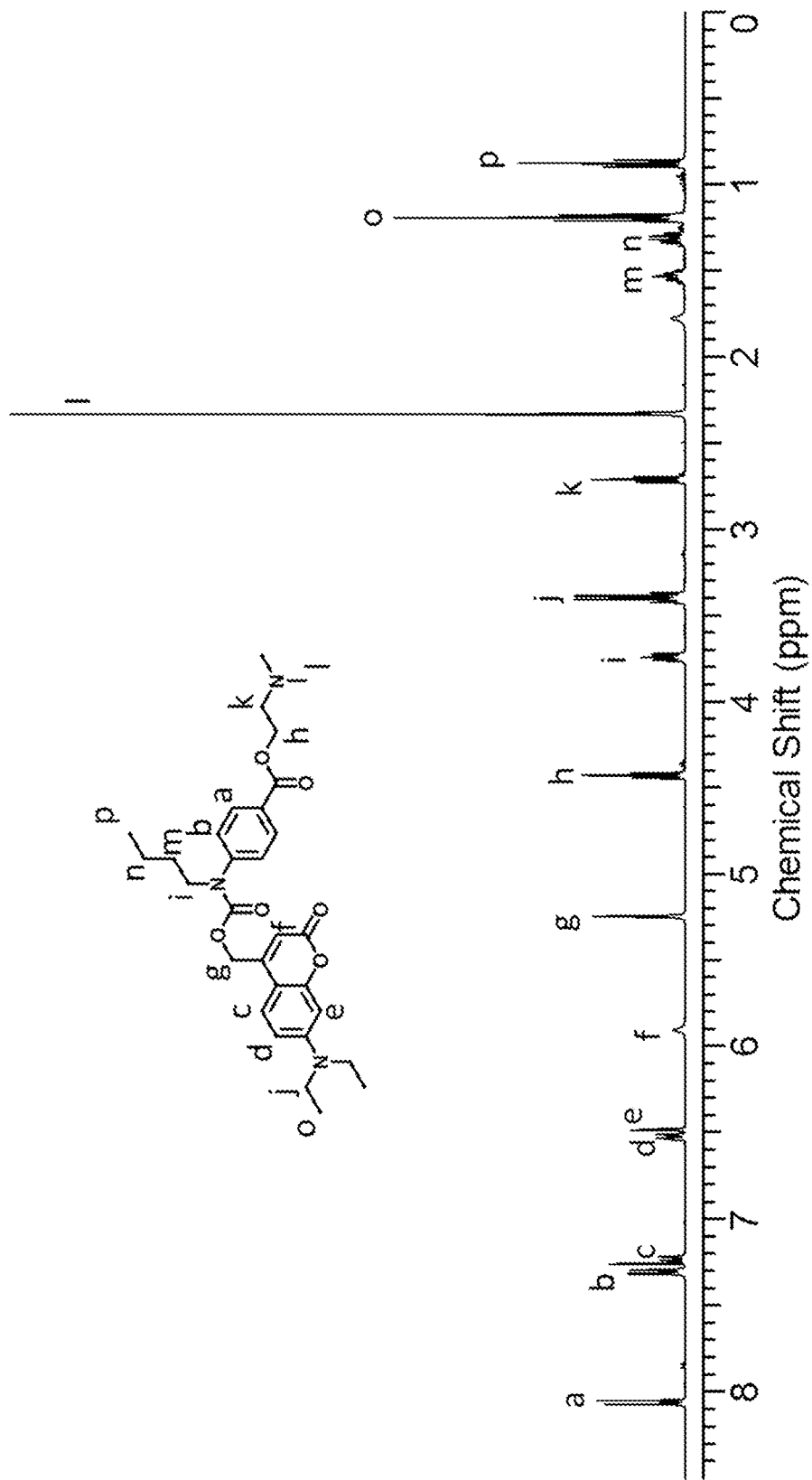
FIG. 17 shows the $^1$H NMR spectrum of compound 9 (CM-T) (shown in FIG. 8).

Example 2. Light-Triggered Release of Conventional Local Anesthetics from a Macromolecular Progdrug for On-Demand Local Anesthesia Results and Discussions The molecular design and synthesis of the polymer-drug conjugate (P407-couramin-tetracaine; P407-CM-T) are shown in FIG. 1A. The photo-cleavage reaction is shown in FIG. 1B. In brief, a coumarin derivative bi-functionalized at the 4-position of the coumarin ring was synthesized, then an azide group was introduced for click reaction with the P407. Then, tetracaine was connected to the coumarin through a carbamate linkage. The resulting coumarin-tetracaine conjugate was then conjugated onto an alkyl-functionalized P407 through azide-alkyne "click" cycloaddition.[22,23] After the reaction, the molecular weight of the polymer (determined with a polystyrene standard) as measured by gel permeation chromatography (GPC) increased from 12.6 k to 13.6 k. In the $^1$H NMR spectrum of P407-CM-T (FIG. 1C), peaks could be clearly assigned to each moiety of the molecule, indicating its successful synthesis: the peak at 8.03-8.04 ppm is representative of the tetracaine moiety; the peaks at 6.70-6.68 ppm, 6.49-6.48 ppm and 6.31-6.29 ppm are representative of the coumarin moiety;[24] and the large peaks at 3-4 ppm and 1-2 ppm are attributable to P407 by comparing to the spectrum of alkyne terminated P407 in FIG. 15.[25] These results demonstrated the successful synthesis of the designed material. More detailed chemical characterization of all compounds are available in FIGS. 10-17.

Figure 2A:
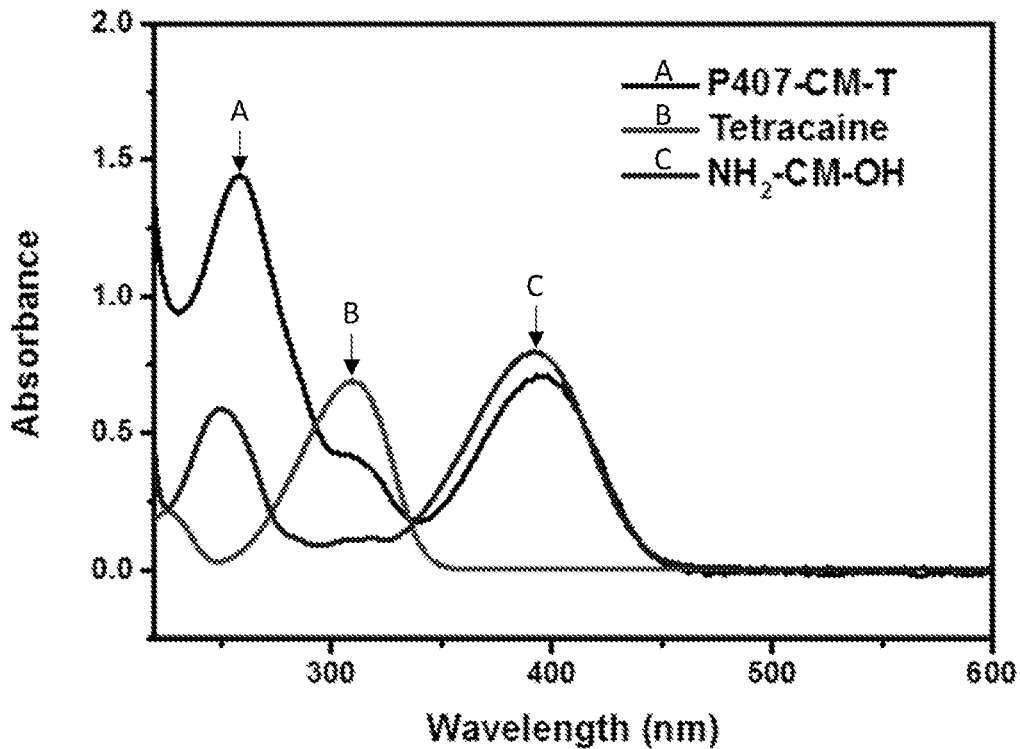
FIGS. 2A-2B show the physical properties of P-CM-T.

P407-CM-T aqueous solution showed strong absorption in the blue range with a maximum at 394 nm and a full width at half-maximum (fwhm) of 64 nm (FIG. 2A). By comparing to the absorption spectra of coumarin and tetracaine, the absorption peak of P407-CM-T at around 400 nm can be attributable to the coumarin moiety, and the peak at around 300 nm to the tetracaine moiety. DEACM derivatives are known to be cleavable by 400 nm LED.[24, 26] Therefore, a 400 nm LED with tunable intensity was used in the triggering experiments.

Figure 2B:
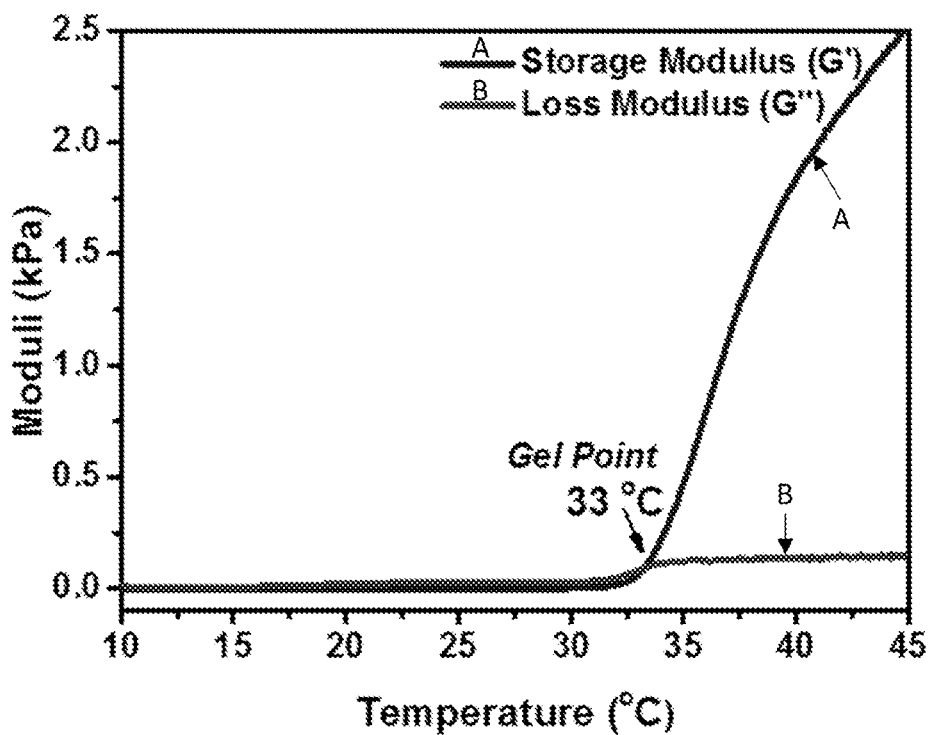

The reverse thermal gelation property of P407-CM-T (20 wt % in aqueous) was verified by oscillatory shear rheology (10 rads$^{-1}$, 1% strain, 1° C. min$^{-1}$). The loss modulus (G") was higher than the storage modulus (G') at <30° C., indicating a liquid-like property, which ensured the material would be injectable. G' became greater than G" at about 33° C., indicating gelation (FIG. 2B). This property could be beneficial for the material to be retained at the site of injection,[27] where drug release could subsequently be triggered.

Figure 3A:
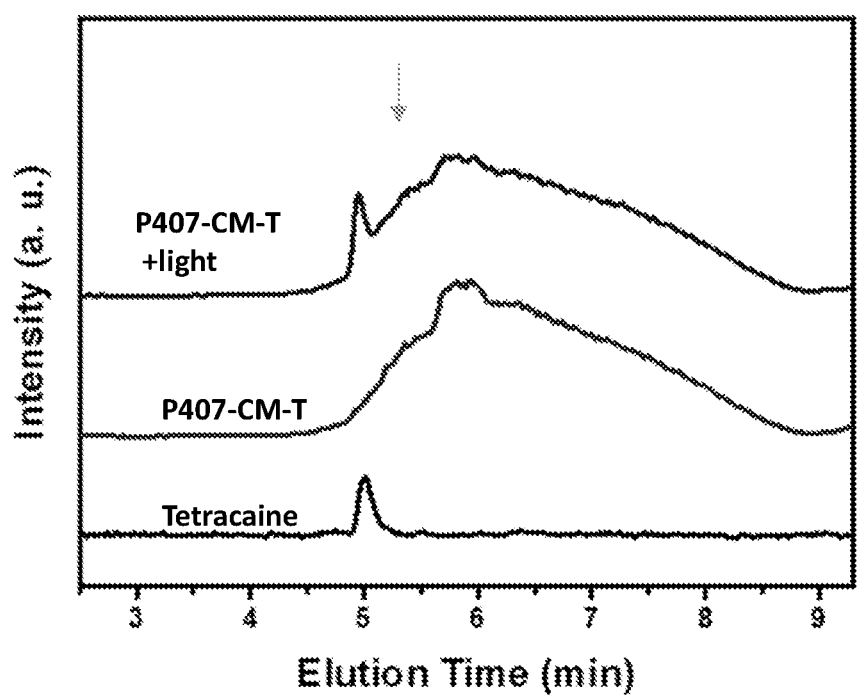
FIGS. 3A-3C show the in vitro photocleavage of P407-CM-T.
Figure 3B:
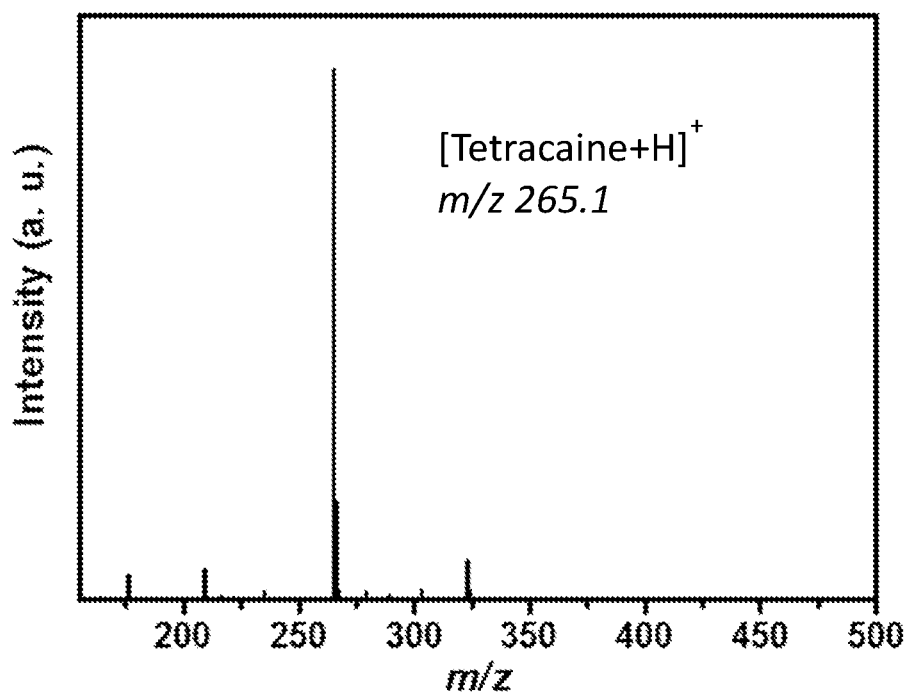
Figure 3C:
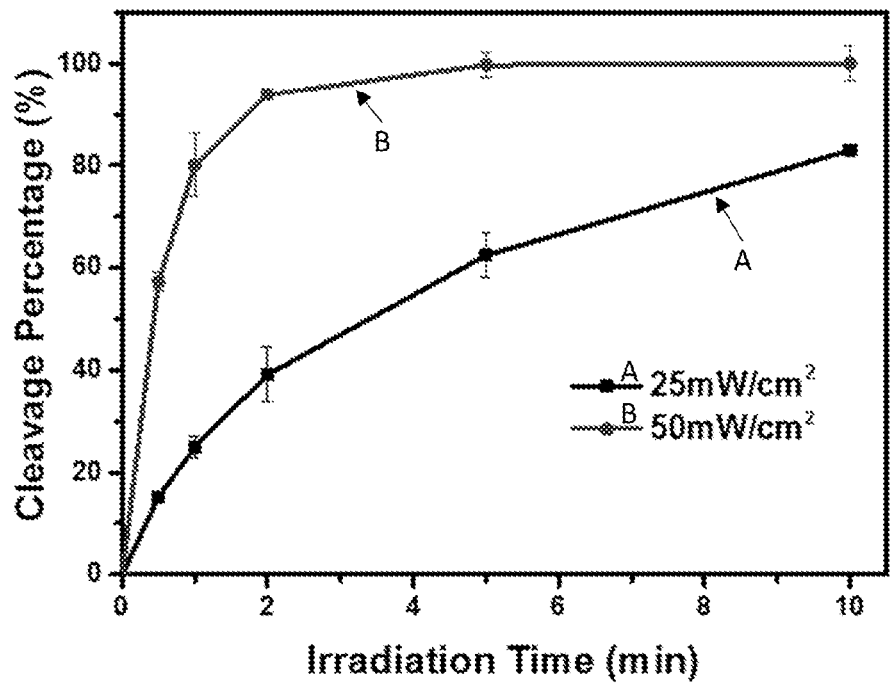

The ability of P407-CM-T to release tetracaine under 400 nm light was studied in vitro (FIG. 3A). Irradiation of P407-CM-T (10 mg/mL) with 400 nm light at 50 mW/cm$^2$ revealed a peak on liquid chromatography that was not seen in unirradiated P407-CM-T and that co-migrated with free tetracaine. The small molecule released from P407-CM-T after irradiation had the molecular weight of tetracaine ion (m/z of 265.1) by liquid chromatography-mass spectroscopy (LC-MS) (FIG. 3B), indicating that P407-CM-T can release tetracaine in its native form. Almost all the conjugated drug was cleaved from P407-CM-T (10 mg/mL) within 120 s of irradiation at 50 mW/cm$^2$, and approximately 40% of cleavage occurred within 120 s at 25 mW/cm$^2$ (FIG. 3C). When P407-CM-T solution was kept in the dark at 37° C. for two weeks, no tetracaine was released, indicating good stability in the dark.

Figure 4A:
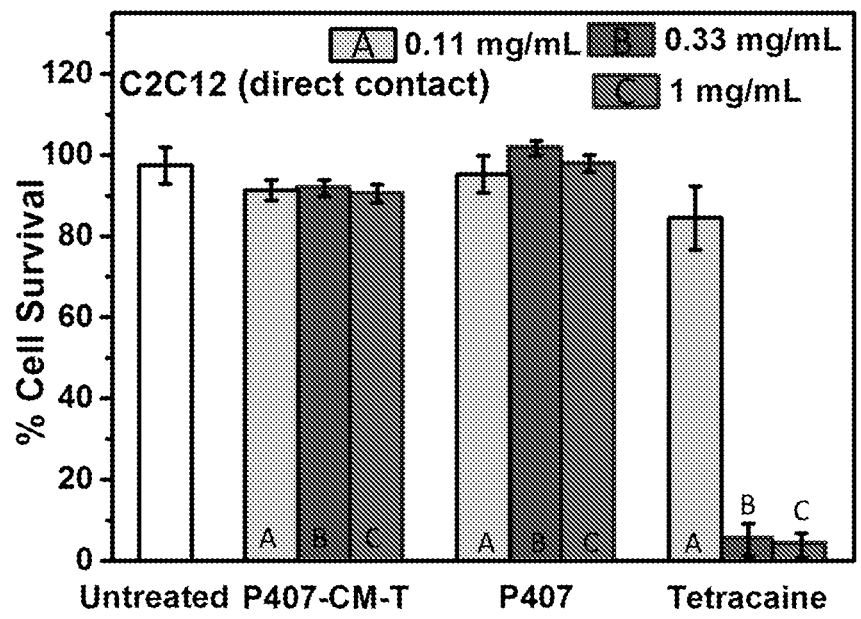
FIGS. 4A-4D show the cytotoxicity of P407-CM-T.
Figure 4B:
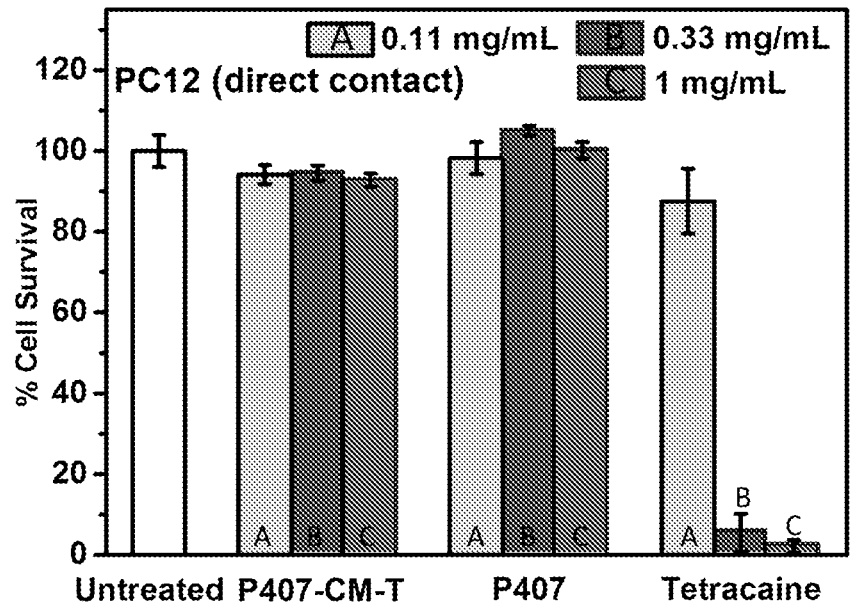
Figure 4C:
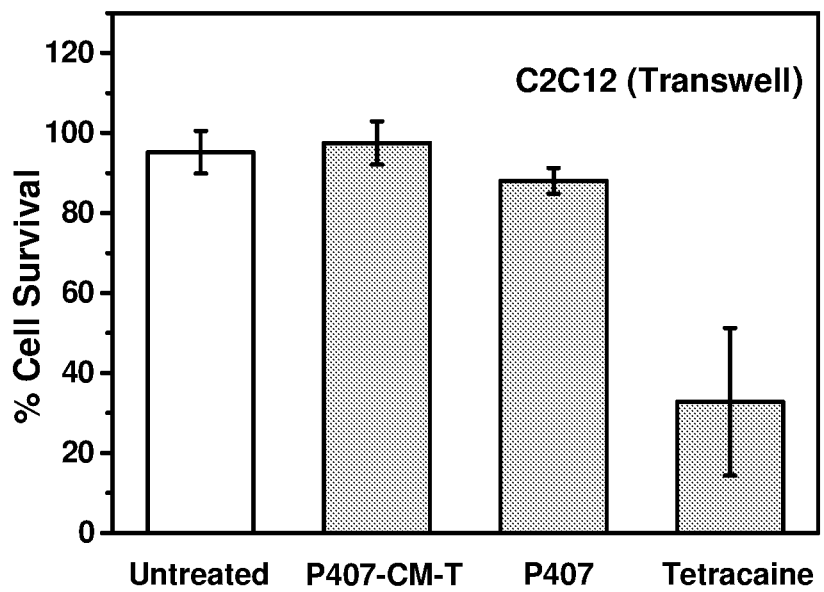
Figure 4D:
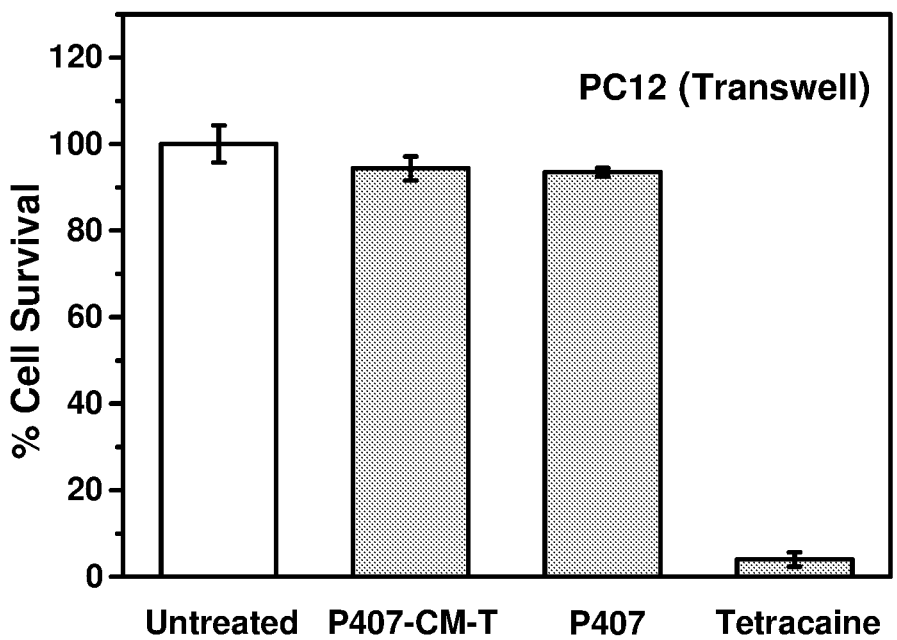

Before testing the material in vivo, test materials were evaluated in vitro with C2C12 and PC12 cells to assess cytotoxicity to muscle and nerve cells respectively. Different compounds were directly added into the cell culture media (1 mg/mL, 0.33 mg/mL and 0.11 mg/mL) and incubated in the media bathing the cells (i.e. in direct contact with them) in conventional cell culture wells. After 24 h, cell viabilities were evaluated with the MTS assay, and their survival expressed as percentages of results in untreated cells. Free tetracaine showed high cytotoxicity in both cell lines, while P407 and P407-CM-T showed little cytotoxicity (FIGS. 4A-4B). Due to the high molecular weight of the polymer-containing samples, their molar concentrations were perforce lower than that of the small molecule tetracaine. It would not be practical to culture cells in media containing the polymer concentration to be used in vivo (20 wt %), which would be very viscous. Therefore, test materials were placed in Transwell® inserts such that they were in continuity with the cell culture media. Here, also both P407 and P407-CM-T had no effect on cell viability (p>0.05 compared to untreated cells) while tetracaine greatly reduced cell survival (p<0.05 compared to untreated cells) in both cell lines (FIGS. 4C-4D). These results indicated that covalently linking tetracaine onto P407 can effectively reduce its cytotoxicity, presumably because there was little free tetracaine.

The effectiveness of light-triggered anesthesia using P407-CM-T was assessed in vivo after footpad injection in the rat (Table 1);[17, 28-32] this model was selected because it was anticipated that 400 nm light would not penetrate deeply into tissue.[33]

TABLE 1

Duration of block for different compounds without or with a single irradiation event

| Compound | Irradiance (W/cm$^2$) | Irradiation Duration (min) | Duration of Block (min) |
|---|---|---|---|
| Tetracaine | 0 | 0 | 28.6 ± 7.1 |
| CM-T | 0 | 0 | 43.9 ± 11.4 |
| P407-CM-T | 0 | 0 | 0 |
| P407-CM-T | 0.2 | 2 | 19.5 ± 4.5 |
| P407-CM-T | 0.3 | 2 | 36.5 ± 8.9 |
| P407-CM-T | 0.3 | 5 | 66.7 ± 24 |
| saline | 0.3 | 2 | 0 |

Figure 5A:
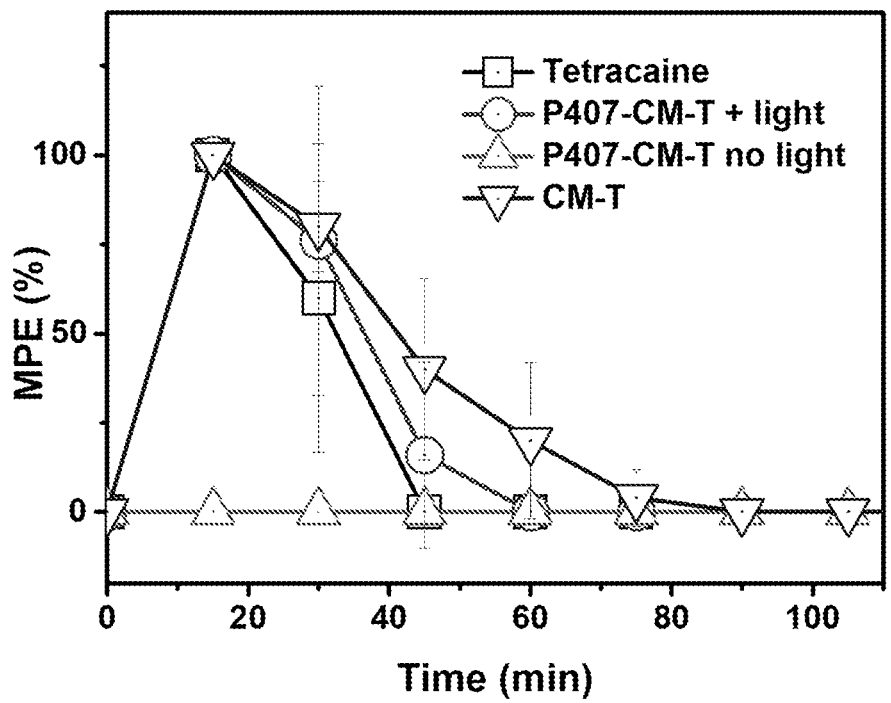
FIGS. 5A-5E show the phototriggered local anesthesia in the rat footpad.
Figure 5B:
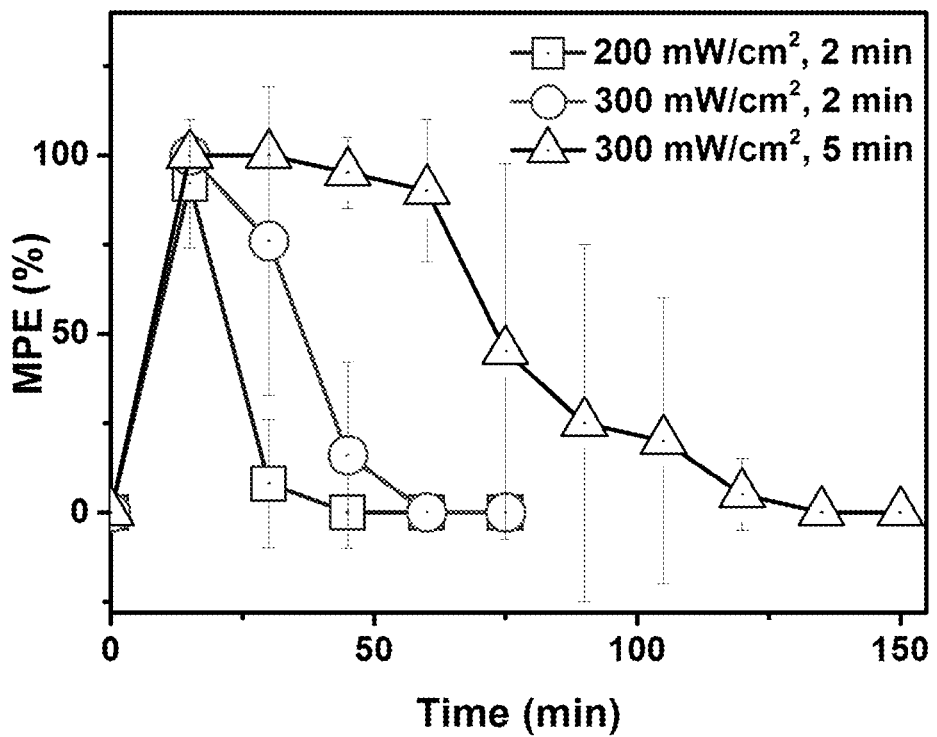
Figure 5C:
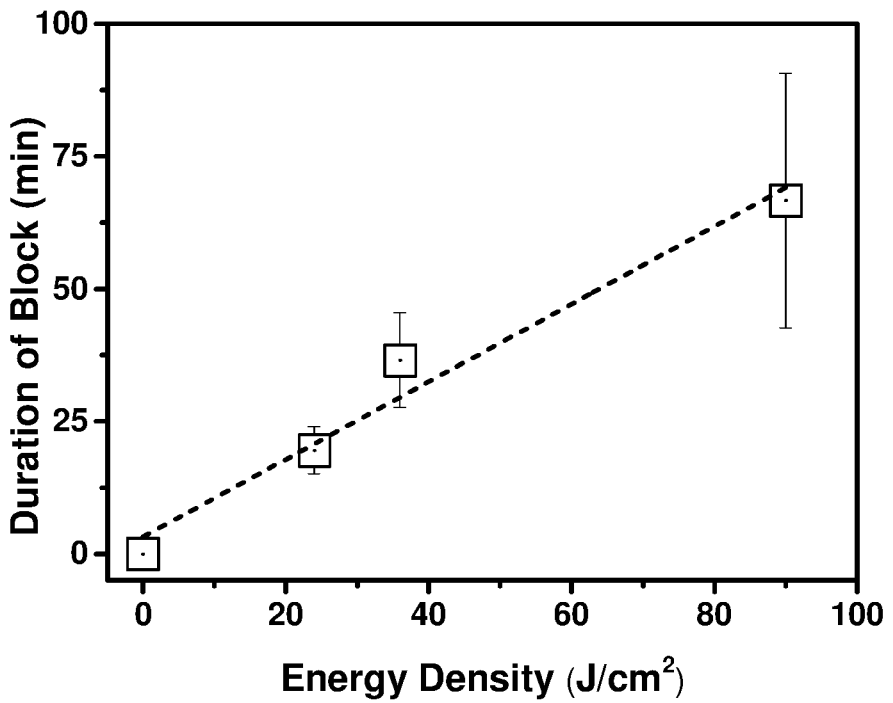
Figure 5D:
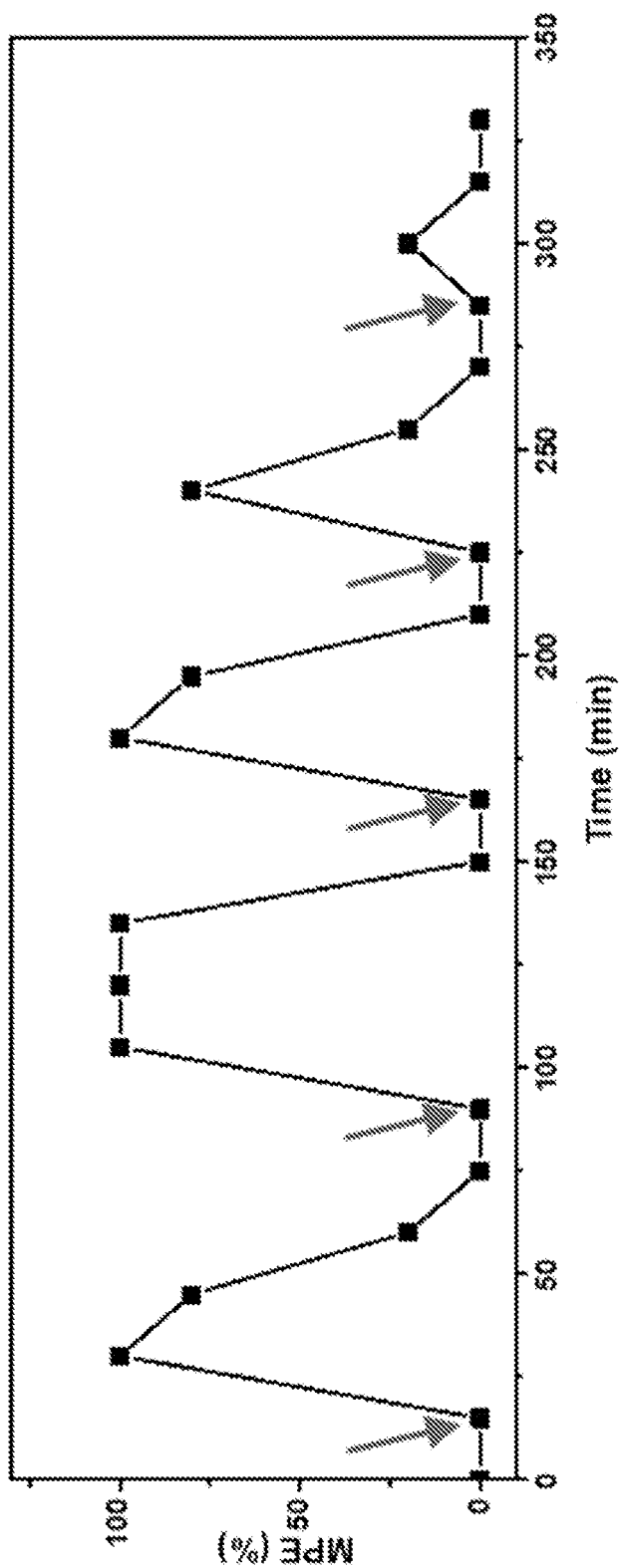
Figure 8:
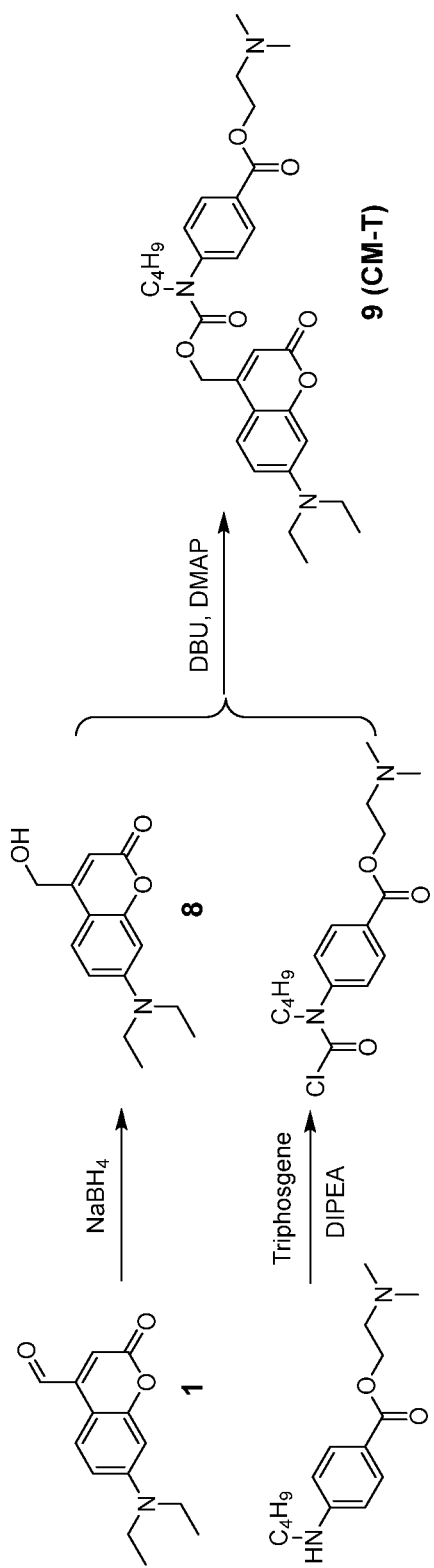
FIG. 8 shows the exemplary synthetic route to CM-T. The conditions for the reactions are depicted.
Figure 9:
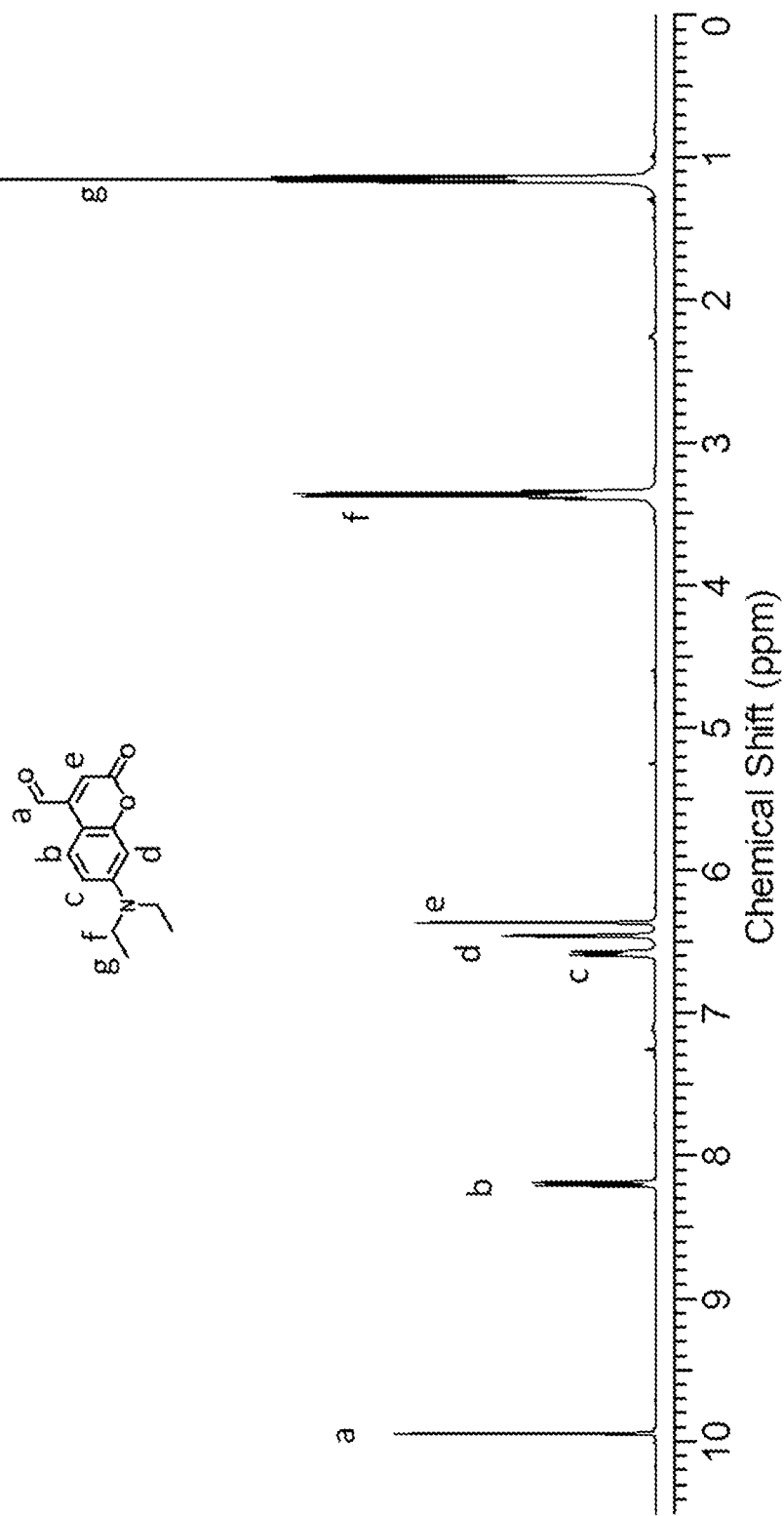
FIG. 9 shows the $^1$H NMR spectrum of compound 1 (shown in FIG. 7).
Figure 10:
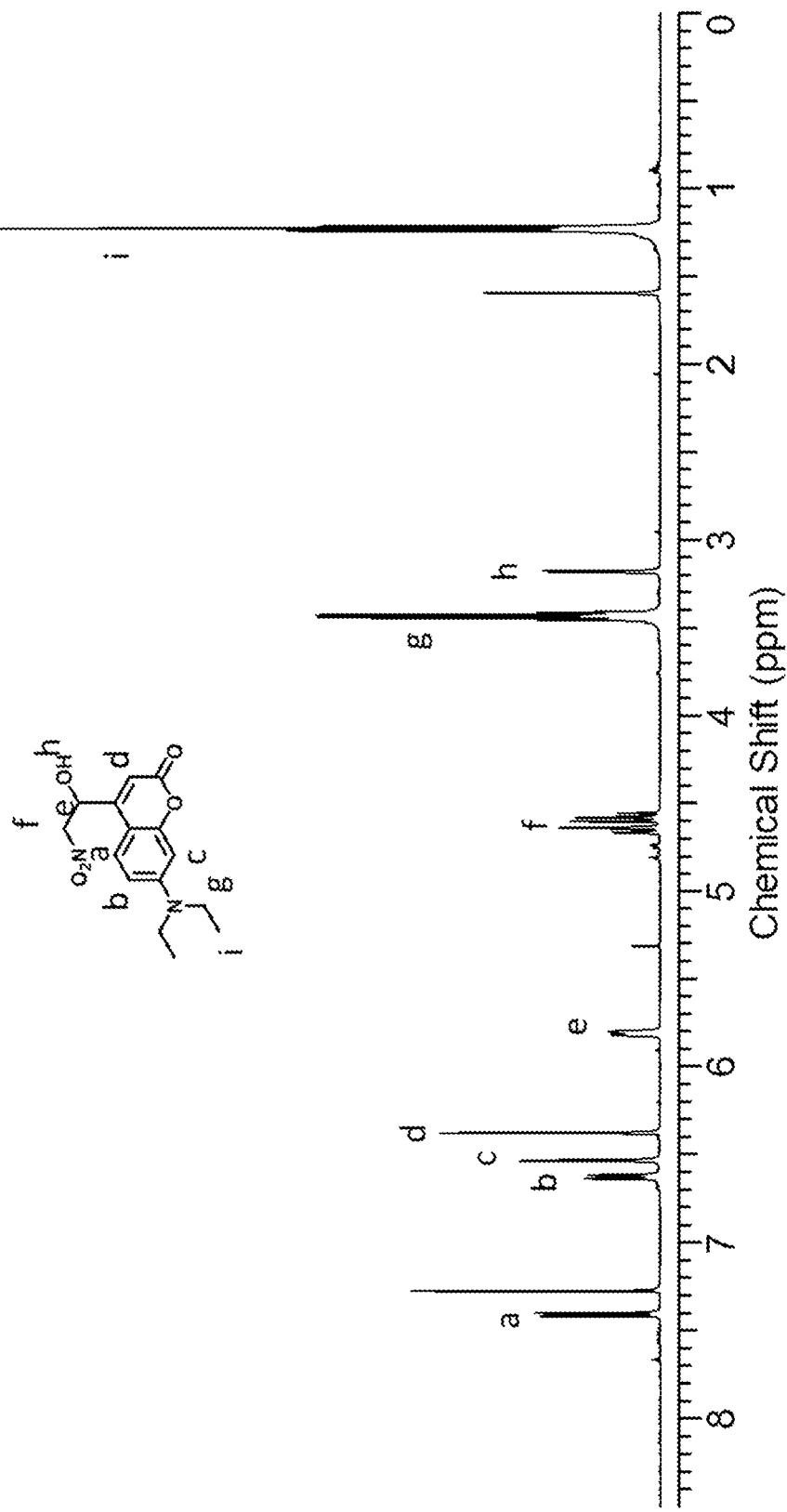
FIG. 10 shows the $^1$H NMR spectrum of compound 2 (shown in FIG. 7).
Figure 11:
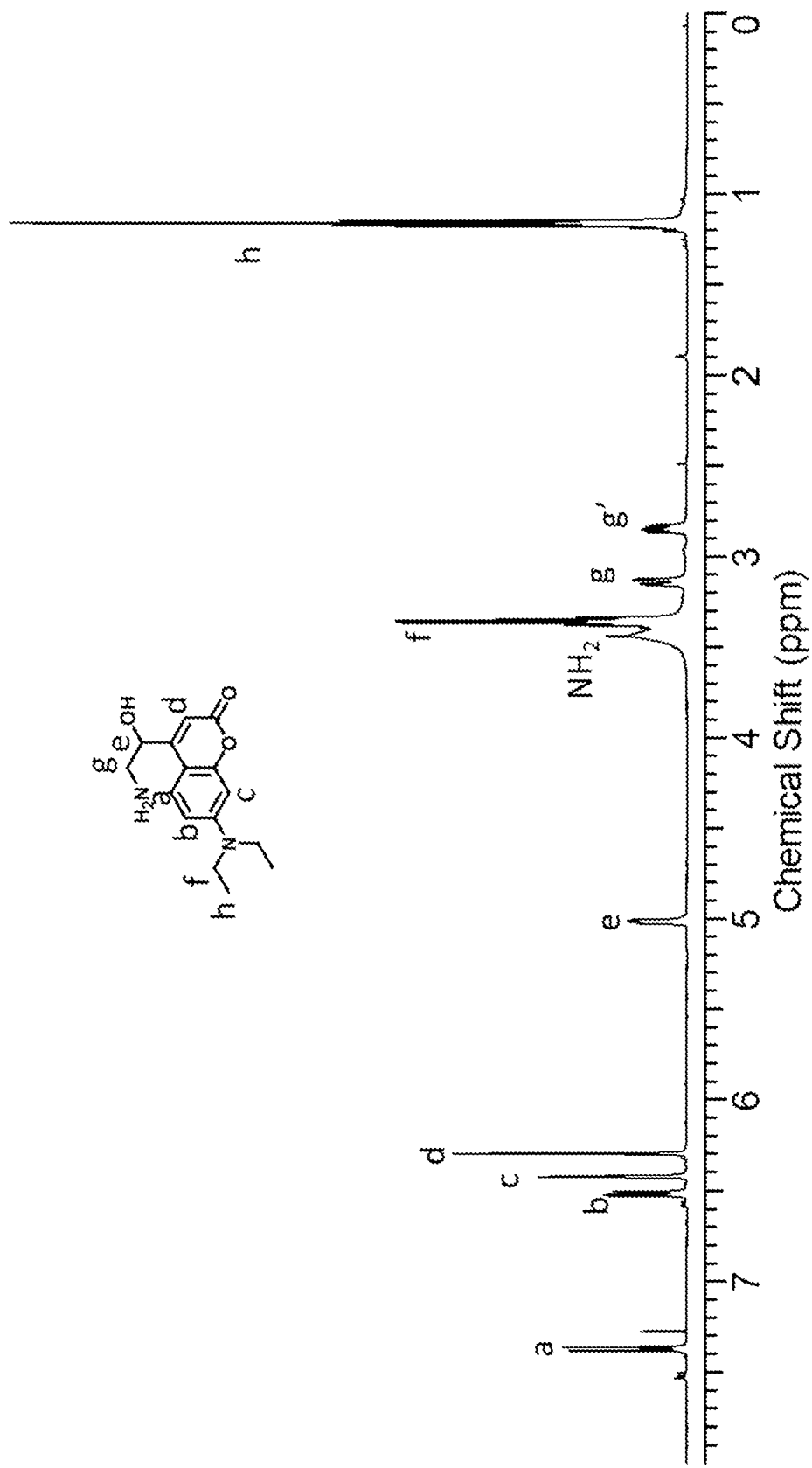
FIG. 11 shows the $^1$H NMR spectrum of compound 3 (shown in FIG. 7).
Figure 12:
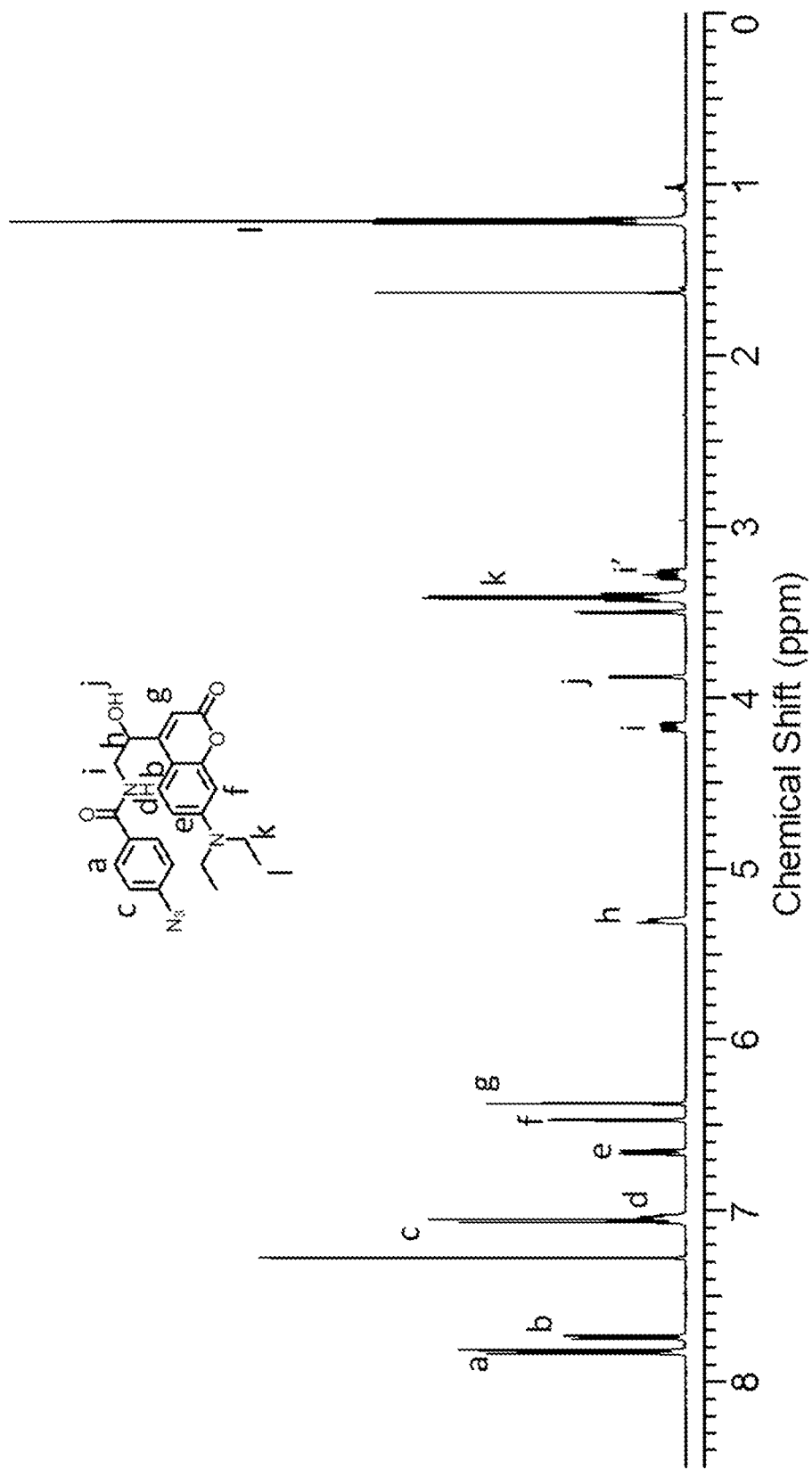
FIG. 12 shows the $^1$H NMR spectrum of compound 4 (shown in FIG. 7).
Figure 13:
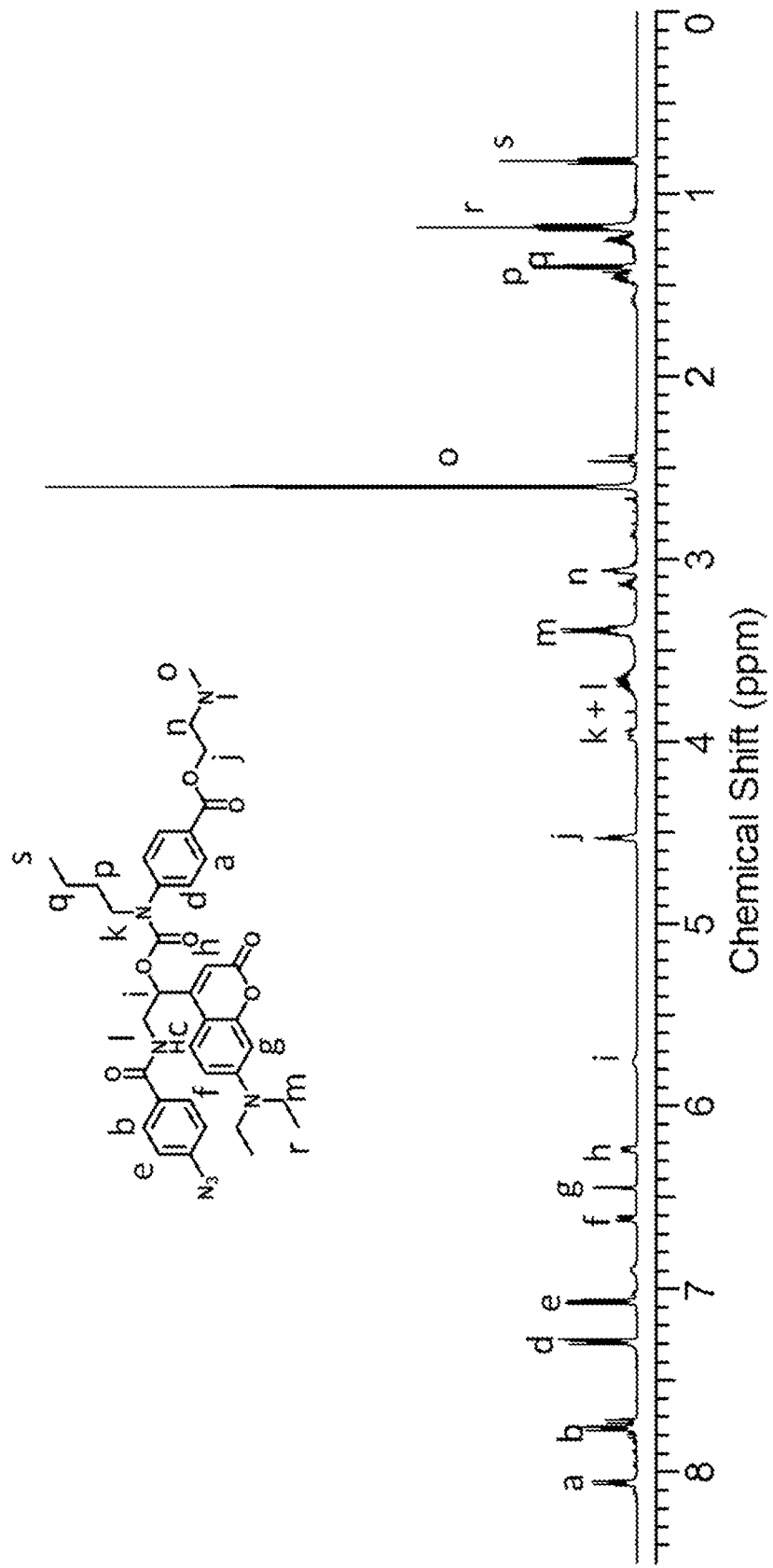
FIG. 13 shows the $^1$H NMR spectrum of compound 5 (shown in FIG. 7).
Figure 14:
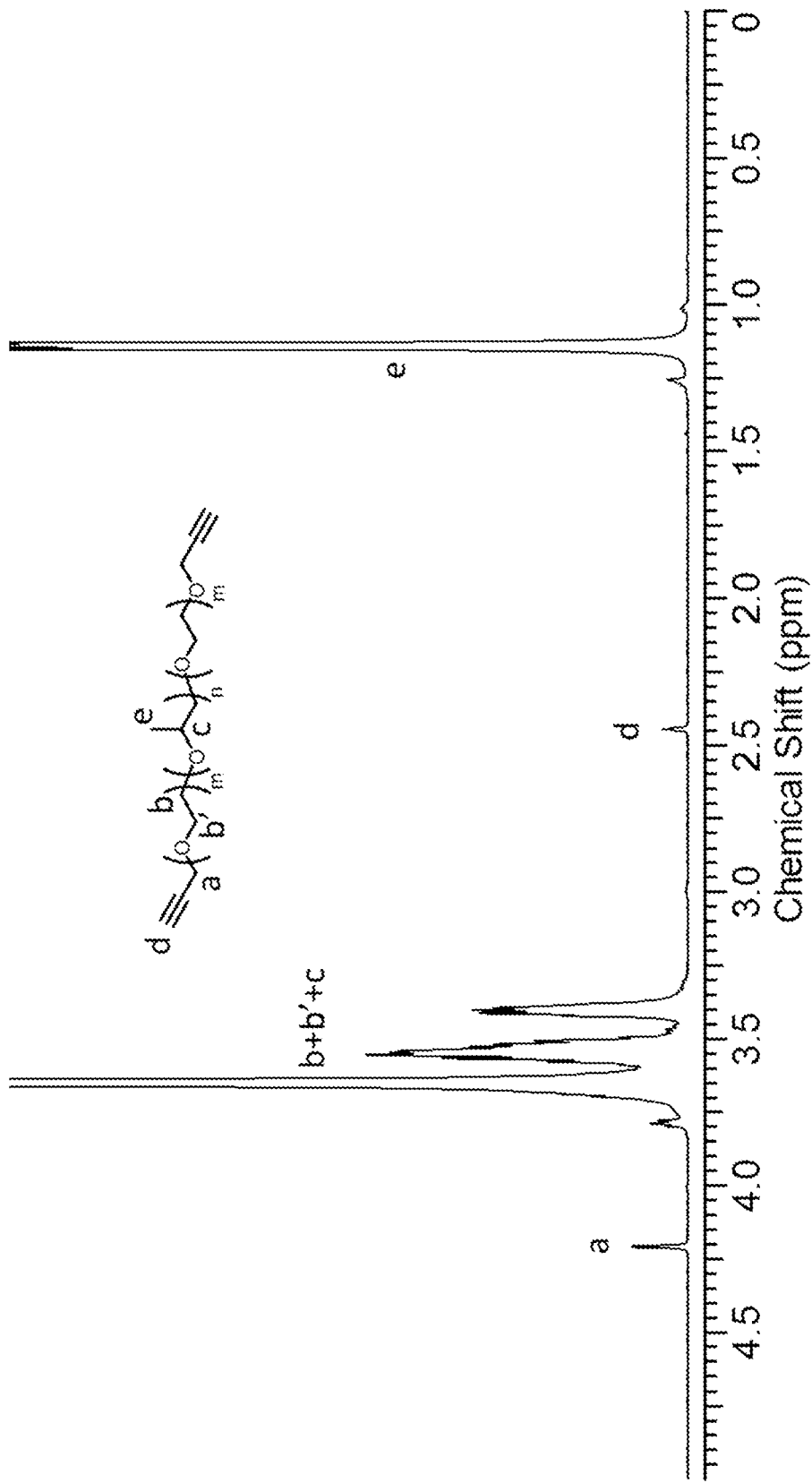
FIG. 14 shows the $^1$H NMR spectrum of compound 6 (shown in FIG. 7).

A hundred microliters of 20 wt % P407-CM-T were injected into the plantar aspect of the rat hind paw. Neurobehavioral testing was performed by stimulating the rat footpad with a Touch Test sensory evaluator and noting the vocal and/or motor response (foot withdrawal) of the rat, maximum peak effect (MPE) and duration of block was calculated.[17, 28] In the absence of irradiation, P407-CM-T did not cause local anesthesia (FIG. 5A). Irradiation of the site of administration immediately after injection with a 400 nm LED at 200 mW/cm$^2$ for two minutes caused local anesthesia lasting 19.5±4.5 min (FIGS. 5A-5B). Local anesthesia was prolonged to 36.5±8.9 min (FIG. 5B) by increasing the irradiance to 300 mW/cm$^2$ also for 2 minutes (p<0.05 compared to 200 mW/cm$^2$). Extending the irradiation time to five minutes at 300 mW/cm$^2$ further extended local anesthesia to 66.7±24 min (p<0.05 compared to 300 mW/cm$^2$ for 2 min, FIG. 5B). Tetracaine conjugated to coumarin without P407 (chemical structure shown in FIG. 8) produced local anesthesia slightly longer than from tetracaine (p<0.05), possibly due to the large hydrophobic addition to the tetracaine. This indicated that conjugation of the polymer is necessary to inactivate the drug. The duration of local anesthesia bore an almost linear relationship to the irradiation energy density (the product of irradiance and irradiation duration; FIG. 4C), suggesting that the degree of anesthesia could be modulated by varying the irradiance and/or irradiation duration according to patients' changing needs.

Figure 5E:
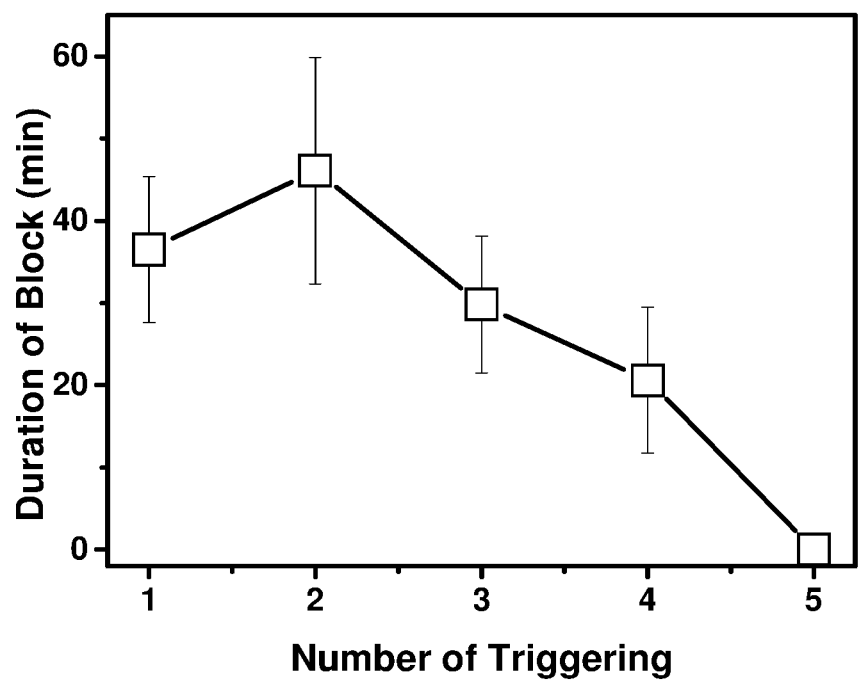

It would be important for a light-triggerable local anesthetic system to be triggered repeatedly, so as to be able to treat pain over an extended period. To assess the ability of P407-CM-T to provide repeated on-demand local anesthesia, animals were injected in the footpad with 0.1 mL of 20 wt % P407-CM-T (FIG. 4D). No nerve block ensued. The animal was then irradiated at the site of injection with 400 nm light at 300 mW/cm$^2$ for 2 min. Subsequently, irradiation was repeated five times, fifteen min after the anesthetic effect from the preceding irradiation event wore off. The duration of block generally decreased with successive triggering events (FIG. 5E). This was possibly because of drug depletion after each triggering event. Triggering could also be delayed for 2 h or 6 h after injection; there was no nerve block until irradiation occurred. Delays in triggering led to fewer triggerable peaks, presumable because of the polymer depletion and loss of triggerable material.

Figure 6:
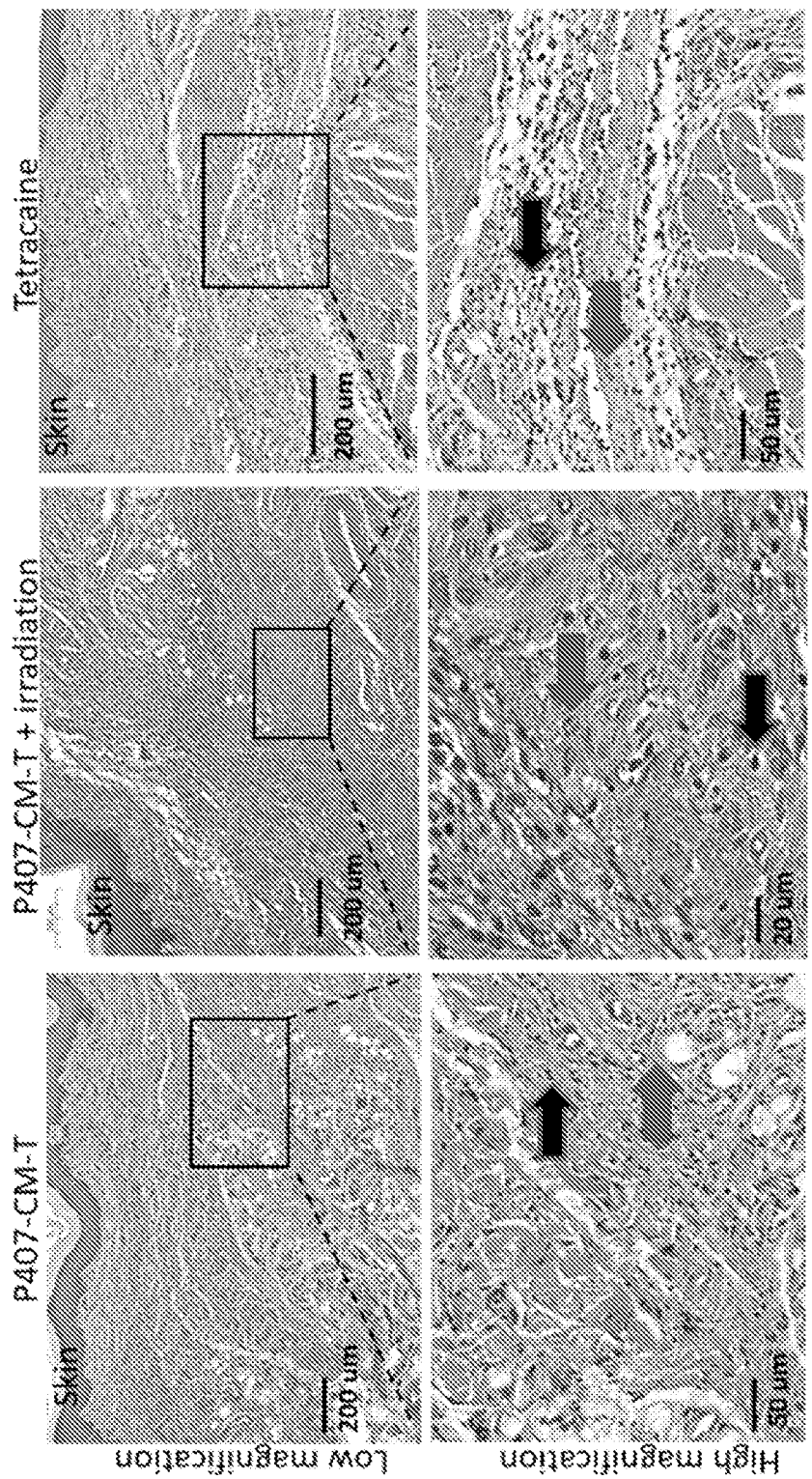
FIG. 6 shows the tissue reaction to rat foot pad injections on day 4 after injection of P407-CM-T (with/without irradiation) or tetracaine. Inflammation at the injection site was characterized by lymphocytes and macrophages extending from the sub-epidermal layers into the deeper muscular layer.
Figure 7:
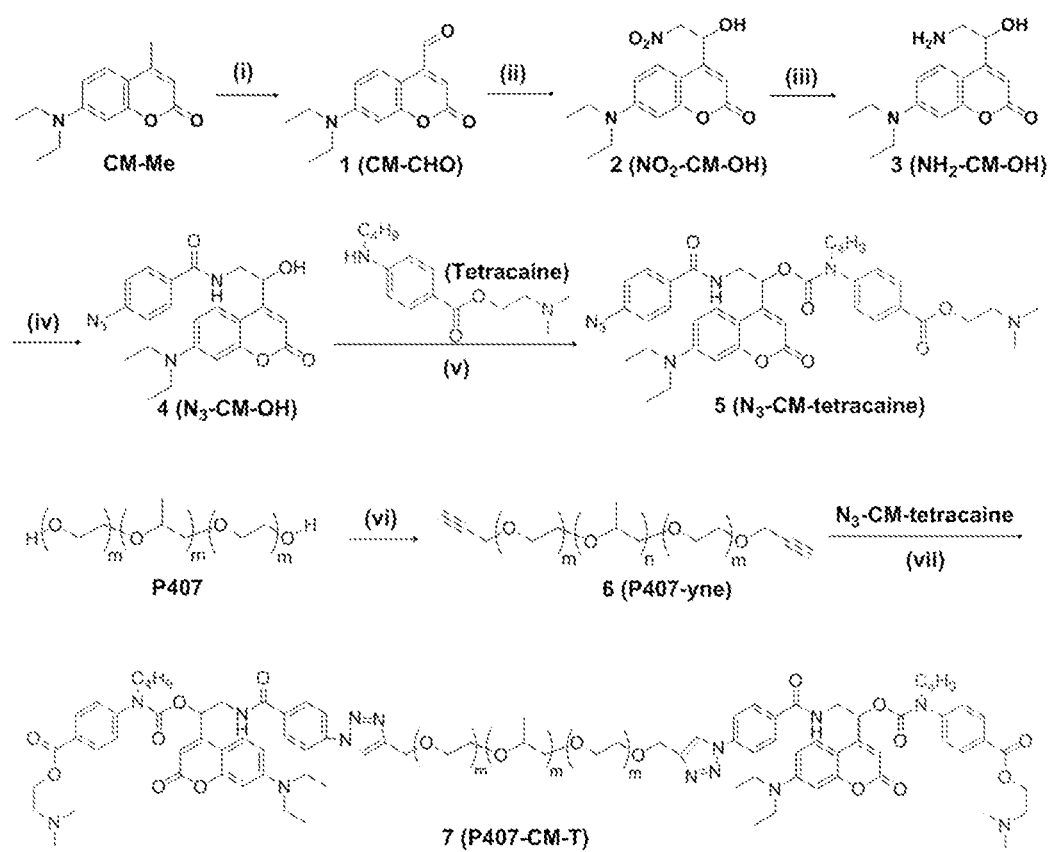
FIG. 7 shows the exemplary synthetic route to P407-CM-T. The conditions for the reactions are: (i) SeO$_2$, 1,4-dioxane, reflux; (ii) CH$_3$NO$_2$, N,N,N'N'-tetramethylethylenediamine, THF; (iii) Zn, acetic acid; (iv) 4-azidobenzoic acid, DIC, DMAP, DCM; (v) tetracaine, triphosgene, DIPEA, DBU, DCM; (vi) sodium hydride, THF; (vii) Copper (II) sulfate pentahydrate, (+)-sodium L-ascorbate, methanol/H$_2$O.

To assess tissue reaction to the formulations, rats were euthanized 4 days and 14 days after injections, and their foot pads were harvested. Saline injections resulted in a very mild localized chronic inflammation (i.e. lymphocytes and macrophages) in the subcutaneous layer on day 4 which decreased to a minimal chronic inflammation with mild fibrosis by day 14. P407-CM-T injections without irradiation caused mild-moderate chronic inflammation on days 4 (FIG. 6) and decreased to very mild inflammation with fibrosis on day 14, which was similar to that from P407 injections. P407-CM-T injections with irradiation on the first day caused moderate chronic inflammation on day 4 extending from the sub-epidermal layers into the deeper muscular layers (FIG. 6). This inflammation also decreased to mild by day 14. The greater inflammation in animals P407-CM-T that were irradiated was probably due to the release of tetracaine since the tissue reaction was similar to that of tetracaine injection (FIG. 6).

Triggered local anesthesia would allow patients to adjust their pain relief as needed without needing systemic medications such as opioids or procedures requiring skilled personnel (at least after the initial application). Light, due to its tunable wavelength, irradiance, area and duration of exposure, is a suitable trigger. Laser sources are commonly used in light-triggered drug delivery systems due to their monochromaticity, coherence and high intensity. However, laser sources can be expensive and relatively bulky, and their high intensity can cause tissue injury. Light from LEDs is not monochromatic, coherent, and is generally comparatively low in intensity. However, LEDs are cheaper and can be small, efficient, and inexpensive. The light source in the current exemplary system was a blue light LED so that it could be potentially used on a larger scale, making them suitable for real-world applications. In certain embodiments, LEDs at 400 nm light do not penetrate deeply into tissue. However, demonstrated here was that the light that penetrated through the skin was sufficient to cleave the bonds between tetracaine and coumarin and release the free drug. Described herein is a macromolecular prodrug of tetracaine that did not cause local anesthesia in the absence of photo-triggering, and provided LED-triggered local anesthesia in proportion to the intensity and duration of irradiation.

Materials and Characterizations

Materials

The other chemical and solvents were used as received: 7-diethylamino-4-methylcoumarin (Sigma-Aldrich, 99%), selenium dioxide (Sigma-Aldrich, 99.8%), celite (Sigma-Aldrich), nitromethane (Alfa Aesar, 98%), N,N,N'N'-tetramethylethylenediamine (Alfa Aesar, 99%), acetic acid (Sigma-Aldrich, 99%), zinc (purum, powder, Sigma-Aldrich), sodium carbonate (Sigma-Aldrich, 99%), sodium chloride (Sigma-Aldrich, 99%), sodium sulfate anhydrous (Sigma-Aldrich, 99%), 4-azidobenzoic acid (TCI America, 97%), triethylamine (TCI America, 99%), O-(7-Azabenzotriazol-1-yl)-N,N,N',N'-tetramethyluronium hexafluorophosphate (HATU, Chem-Impex International, 99%), triphosgene (Chem-Impex International, 99%), N,N-diisopropylethylamine (DIPEA, Sigma-Aldrich, 99%), 1,8-diazabicyclo[5.4.0]undec-7-ene (Alfa Aesar, 99%), Poloxamer 407 (from BASF), sodium hydride (Sigma-Aldrich, dry, 90%), propargyl bromide (Sigma-Aldrich, 80 wt % in toluene), Copper (II) sulfate pentahydrate (Sigma-Aldrich, 99%), sodium (+)-L-ascorbate (Sigma-Aldrich, 99%), sodium borohydride (Sigma-Aldrich, 98%), tetracaine (Sigma-Aldrich, 98%), tetracaine hydrochloride (Sigma-Aldrich, meets United States Pharmacopeia specifications), dichloromethane (Sigma-Aldrich, 99% or anhydrous), hexane (Sigma-Aldrich, mixture of isomers, 99%), ethyl acetate (Sigma-Aldrich, 99%), dioxane (Sigma-Aldrich, 99%), tetrahydrofuran (Sigma-Aldrich, 99%), diethyl ether (Sigma-Aldrich, 99%), methanol (Sigma-Aldrich, 99%), d-chloroform (Cambridge Isotope Laboratories Inc., 99%). NO2-CM-OH was synthesized according previously reported method with some modifications.

Characterizations $^1$H and $^{13}$C NMR experiments were measured on a Varian 400 M or 500 NMR spectrometer. The spectra were referenced to the residual solvent peak in CDCl$_3$ at δ 7.27 ppm for $^1$H proton and δ 77.00 ppm for $^{13}$C, respectively.

An Agilent 1260 series High Performance Liquid Chromatography (HPLC) with a UV-vis detector was used for analyzing the released drug in the releasing experiments. The mobile phase was 40/60 acetonitrile/water with flow rate of 0.5 mL/min. An Anilent 1200 Series Liquid chromatography-mass spectrometry (LC-MS) with a 6130 Quadrupole MS detector was used for the LC-MS experiments. Gel permeation chromatography (GPC) were measured in THF at 35° C. on Tosoh EcoSEC instrument. The flow rate was 0.35 mL/min.

UV-vis absorption spectra were measured on an Agilent 8453 UV-vis G1103A spectrometry.

Photo-triggering experiments were performed using a BLS-13000-1 LED driver and an LCS-0405-50-XX lamp from MIGHTEX.

Rheology experiments were tested on a TA DHR-2 rheometer with a frequency of 1 Hz, shear strain of 1% and a temperature ramp between 10° C. and 45° C.

Sample preparation. Tetracaine hydrochloride, P407 or P407-CM-T were direct dissolved in water. CM-T was dissolved in a small amount of ethanol, and equal molar of HCl (2 M in ethanol) was added. The solvent was completely removed by a rotatory evaporator and oil pump, and the resulted CM-T hydrochloride salt was re-dissolved in water.

Photocleavage of P407-CM-T in vitro. To demonstrate the capability of P407-CM-T to release tetracaine in the native form, 100 uL P407-CM-T solution (10 mg/mL) was placed in a 2 mL centrifuge tube and irradiated with 400 nm LED light with designed intensity and time. The solution was then diluted into 1 mL for HPLC or LC-MS measurements to verify the release of tetracaine and determine the concentrations. Dark stability of P407-CM-T was evaluated by placing the solution of P407-CM-T in a 37° C. oven for designed days, followed by HPLC measurements.

Cytotoxicity analysis. For the "direct contact" experiments, the cells were incubated in 48-well plates with concentration of formulations of 1, 0.33, 0.11 mg/mL in the media for all samples. For the "indirect contact" experiments, the cells were incubated in 24-well plates with a transwell in each well, in which 50 μL of tetracaine (0.5% wt %) or P407 (20% wt %) or P407-CM-T (20% wt %) was applied. After 24 h, the cell viabilities were evaluated with MTS assay as percentages of the control.

Animal studies. Animal studies were performed according to standard protocols approved by the Boston Children's Hospital Animal Care and Use Committee. Adult Sprague-Dawley rats (300-400 g, from Charles River Laboratories)

were housed in groups under a 12 h/12 h light/dark cycle. Under brief isoflurane-oxygen anesthesia, 100 µL of solution were injected into the plantar aspect of the rat hind paw. Neurobehavioral testing was performed at predetermined intervals according to previously reported method by stimulating the rat footpad with Touch Test sensory evaluators (filament with target force of 180 g) and noting the vocal or motor response (foot withdrawal) of the rat according to previous reports,[34,35] modified from previous reports.[36-39] An absence of vocalization or withdrawal after five trials was defined as complete nerve block or 100% maximum possible effect (MPE). In photo triggered anesthesia experiments, the hind paw of the rat with injected formulations was irradiated by the LED at designed intensity for 2-5 min under brief isoflurane-oxygen anesthesia.

Statistics. Data were described with means and standard deviations calculated from Microsoft excel.

Histology. The rats were euthanized with carbon dioxide 4 days or 14 days after injection. The rat foot pads were dissected, fixed by formalin, embedded in paraffin and underwent standard haematoxylin and eosin (H&E) stain.

REFERENCES

1. McAlvin, J. B. & Kohane, D. S. in Focal Controlled Drug Delivery. (eds. A. J. Domb & W. Khan) 653-677 (Springer US, Boston, MA; 2014).
2. Rwei, A. Y., Sherburne, R. T., Zurakowski, D., Wang, B. & Kohane, D. S. Prolonged Duration Local Anesthesia Using Liposomal Bupivacaine Combined With Liposomal Dexamethasone and Dexmedetomidine. Anesthesia & Analgesia 126 (2018).
3. Weldon, C. et al. Nanoscale Bupivacaine Formulations To Enhance the Duration and Safety of Intravenous Regional Anesthesia. ACS Nano 13, 18-25 (2019).
4. Torchilin, V. P. Multifunctional, stimuli-sensitive nanoparticulate systems for drug delivery. Nature Reviews Drug Discovery 13, 813 (2014).
5. Wang, Y. & Kohane, D. S. External triggering and triggered targeting strategies for drug delivery. Nature Review Materials 2, 17020 (2017).
6. Fleige, E., Quadir, M. A. & Haag, R. Stimuli-responsive polymeric nanocarriers for the controlled transport of active compounds: Concepts and applications. Advanced Drug Delivery Reviews 64, 866-884 (2012).
7. Linsley, C. S. & Wu, B. M. Recent advances in light-responsive on-demand drug-delivery systems. Therapeutic delivery 8, 89-107 (2017).
8. Xiao, P., Zhang, J., Zhao, J. & Stenzel, M. H. Light-induced release of molecules from polymers. Progress in Polymer Science 74, 1-33 (2017).
9. Rwei, A. Y., Wang, W. & Kohane, D. S. Photoresponsive nanoparticles for drug delivery. Nano Today 10, 451-467 (2015).
10. Wong, P. T. et al. Modular Integration of Upconverting Nanocrystal-Dendrimer Composites for Folate Receptor-Specific NIR Imaging and Light-Triggered Drug Release. Small 11, 6078-6090 (2015).
11. Yan, F. et al. Paclitaxel-liposome-microbubble complexes as ultrasound-triggered therapeutic drug delivery carriers. Journal of Controlled Release 166, 246-255 (2013).
12. Rwei, A. Y. et al. Ultrasound-triggered local anaesthesia. Nature Biomedical Engineering 1, 644-653 (2017).
13. Schleich, N. et al. Comparison of active, passive and magnetic targeting to tumors of multifunctional paclitaxel/SPIO-loaded nanoparticles for tumor imaging and therapy. Journal of Controlled Release 194, 82-91 (2014).
14. Mosayebi, J., Kiyasatfar, M. & Laurent, S. Synthesis, Functionalization, and Design of Magnetic Nanoparticles for Theranostic Applications. Advanced Healthcare Materials 6, 1700306 (2017).
15. Klan, P. et al. Photoremovable Protecting Groups in Chemistry and Biology: Reaction Mechanisms and Efficacy. Chemical Reviews 113, 119-191 (2013).
16. Rwei, A. Y. et al. Repeatable and adjustable on-demand sciatic nerve block with phototriggerable liposomes. Proceedings of the National Academy of Sciences 112, 15719-15724 (2015).
17. Zhan, C. et al. Ultrasensitive Phototriggered Local Anesthesia. Nano Letters 17, 660-665 (2017).
18. Rwei, A. Y., Wang, B. Y., Ji, T., Zhan, C. & Kohane, D. S. Enhanced Triggering of Local Anesthetic Particles by Photosensitization and Photothermal Effect Using a Common Wavelength. Nano Letters 17, 7138-7145 (2017).
19. Pardo, M. & Miller, R. D. Basics of Anesthesia E-Book. (Elsevier Health Sciences, 2017).
20. Dumortier, G., Grossiord, J. L., Agnely, F. & Chaumeil, J. C. A Review of Poloxamer 407 Pharmaceutical and Pharmacological Characteristics. Pharmaceutical Research 23, 2709-2728 (2006).
21. Gao, Z. et al. Photo-controlled release of fipronil from a coumarin triggered precursor. Bioorganic & Medicinal Chemistry Letters 27, 2528-2535 (2017).
22. Zhang, W. et al. Rationally Controlling the Self-Assembly Behavior of Triarmed POSS-Organic Hybrid Macromolecules: From Giant Surfactants to Macroions. Macromolecules 50, 5042-5050 (2017).
23. Zhang, W. et al. Toward Controlled Hierarchical Heterogeneities in Giant Molecules with Precisely Arranged Nano Building Blocks. ACS Central Science 2, 48-54 (2016).
24. Wang, W. et al. Efficient Triplet-Triplet Annihilation-Based Upconversion for Nanoparticle Phototargeting. Nano Letters 15, 6332-6338 (2015).
25. Yang, R. et al. Treatment of otitis media by transtympanic delivery of antibiotics. Science Translational Medicine 8, 356ra120 (2016).
26. Wang, Y. et al. Intravenous treatment of choroidal neovascularization by photo-targeted nanoparticles. Nature Communications 10, 804 (2019).
27. Paavola, A. et al. Controlled release of lidocaine from injectable gels and efficacy in rat sciatic nerve block. Pharm Res 12, 1997-2002 (1995).
28. Zhan, C. et al. Phototriggered Local Anesthesia. Nano Letters 16, 177-181 (2016).
29. Khan, M. A., Gerner, P. & Wang, G. K. Amitriptyline for prolonged cutaneous analgesia in the rat. Anesthesiology: The Journal of the American Society of Anesthesiologists 96, 109-116 (2002).
30. Kayser, V. r. & Guilbaud, G. I. The analgesic effects of morphine, but not those of the enkephalinase inhibitor thiorphan, are enhanced in arthritic rats. Brain Research 267, 131-138 (1983).
31. Kayser, V. & Guilbaud, G. Differential effects of various doses of morphine and naloxone on two nociceptive test thresholds in arthritic and normal rats. Pain 41, 353-363 (1990).
32. Fletcher, D., Kayser, V. & Guilbaud, G. Influence of timing of administration on the analgesic effect of bupivacaine infiltration in carrageenin-injected rats. Anesthesiology: The Journal of the American Society of Anesthesiologists 84, 1129-1137 (1996).

33. Fodor, L., Ullmann, Y. & Elman, M. in Aesthetic Applications of Intense Pulsed Light 11-20 (Springer London, London; 2011).
34. Zhan, C. et al. Phototriggered Local Anesthesia. Nano Letters 16, 177-181 (2016).
35. Zhan, C. et al. Ultrasensitive Phototriggered Local Anesthesia. Nano Letters 17, 660-665 (2017).
36. Kayser, V. r. & Guilbaud, G. l. The analgesic effects of morphine, but not those of the enkephalinase inhibitor thiorphan, are enhanced in arthritic rats. Brain Research 267, 131-138 (1983).
37. Kayser, V. & Guilbaud, G. Differential effects of various doses of morphine and naloxone on two nociceptive test thresholds in arthritic and normal rats. Pain 41, 353-363 (1990).
38. Fletcher, D., Kayser, V. & Guilbaud, G. Influence of timing of administration on the analgesic effect of bupivacaine infiltration in carrageenin-injected rats. Anesthesiology: The Journal of the American Society of Anesthesiologists 84, 1129-1137 (1996).
39. Khan, M. A., Gerner, P. & Wang, G. K. Amitriptyline for prolonged cutaneous analgesia in the rat. Anesthesiology: The Journal of the American Society of Anesthesiologists 96, 109-116 (2002).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A composition comprising a compound of Formula (I):

or a pharmaceutically acceptable salt, co-crystal, tautomer, stereoisomer, solvate, hydrate, polymorph, or an isotopically enriched derivative thereof, wherein:
n is an integer of 1 or more;
each instance of X is independently an anesthetic compound, wherein at least one instance of X is of formula:

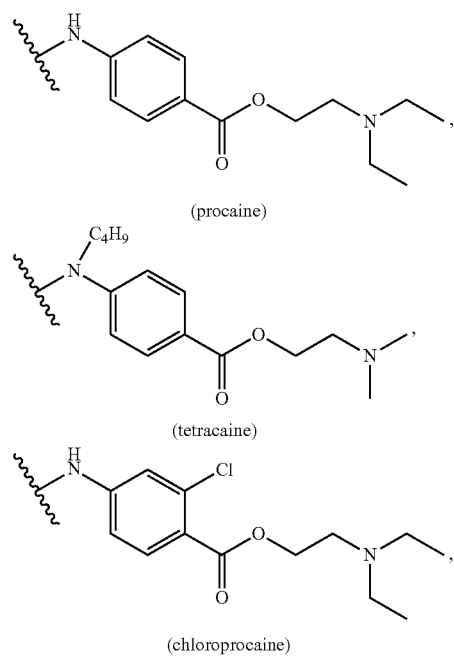

109
-continued

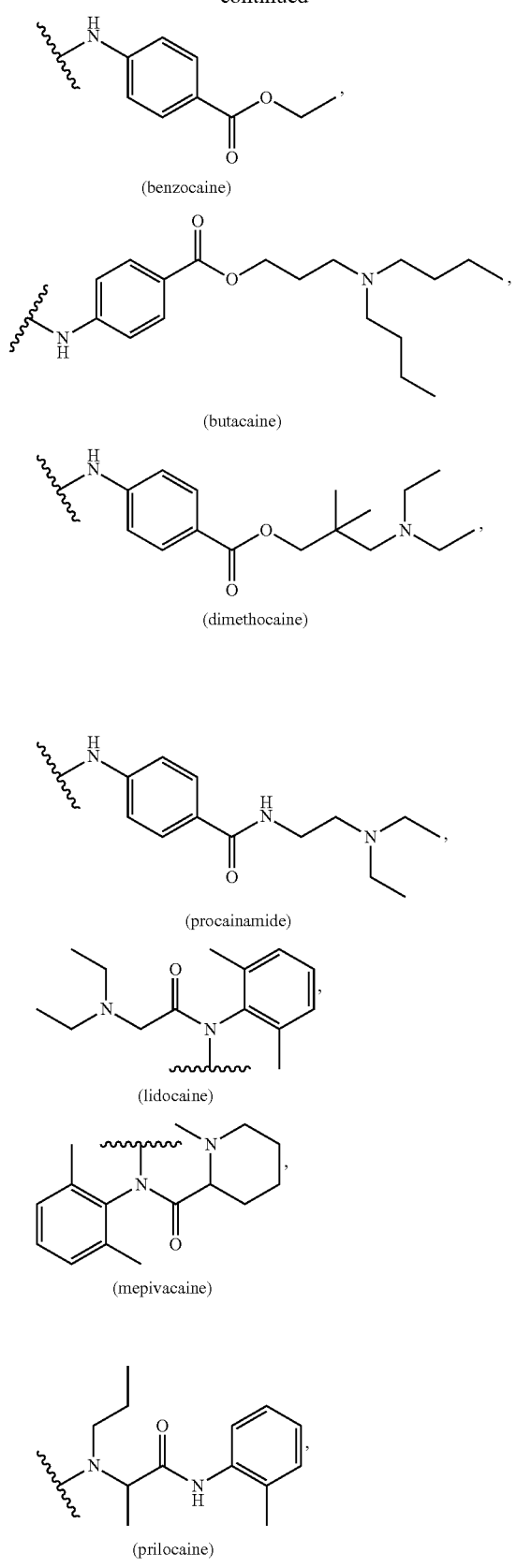

110
-continued

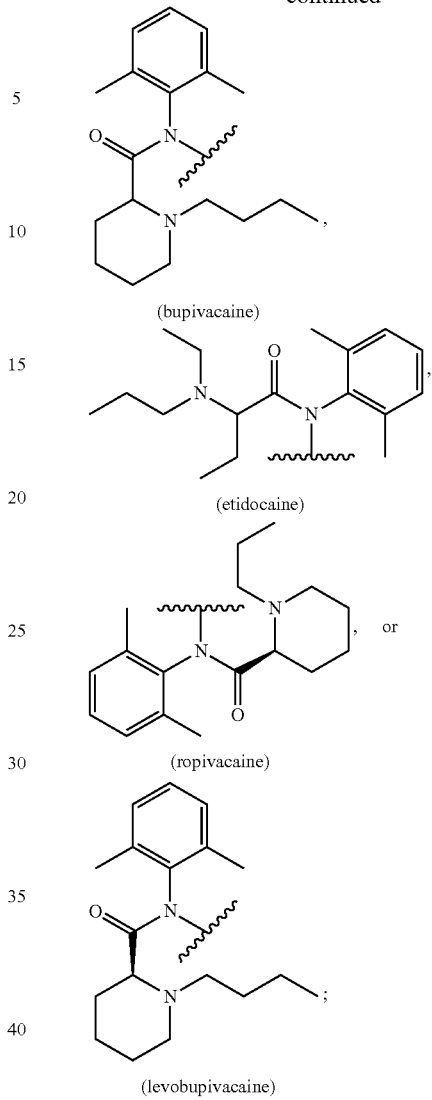

each instance of L is independently a photocleavable linker, wherein at least one instance of L comprises coumarin, o-nitrobenzyl, benzoin, 7-nitroindoline, or p-hydroxyphenacyl; and P is a block copolymer comprising at least one polyether.

2. The composition of claim 1, wherein the compound is of Formula (I-A):

X-L-P-L-X  (I-A), or a pharmaceutically acceptable salt, co-crystal, tautomer, stereoisomer, solvate, hydrate, polymorph, or an isotopically enriched derivative thereof.

3. The composition of claim 1, wherein the bond between each instance of L and each instance of X is cleaved upon illumination with light at an absorption wavelength between approximately 200 nm to 500 nm.

4. The composition of claim 1, wherein P is a block copolymer comprising a poloxamer.

5. The composition of claim 4, wherein the poloxamer is poloxamer P407, poloxamer P331, poloxamer P188, poloxamer P182, poloxamer P124, poloxamer P338, or poloxamer P237 (F87).

6. The composition of claim 1, wherein at least one instance of the moiety

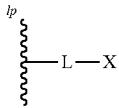

is of formula:

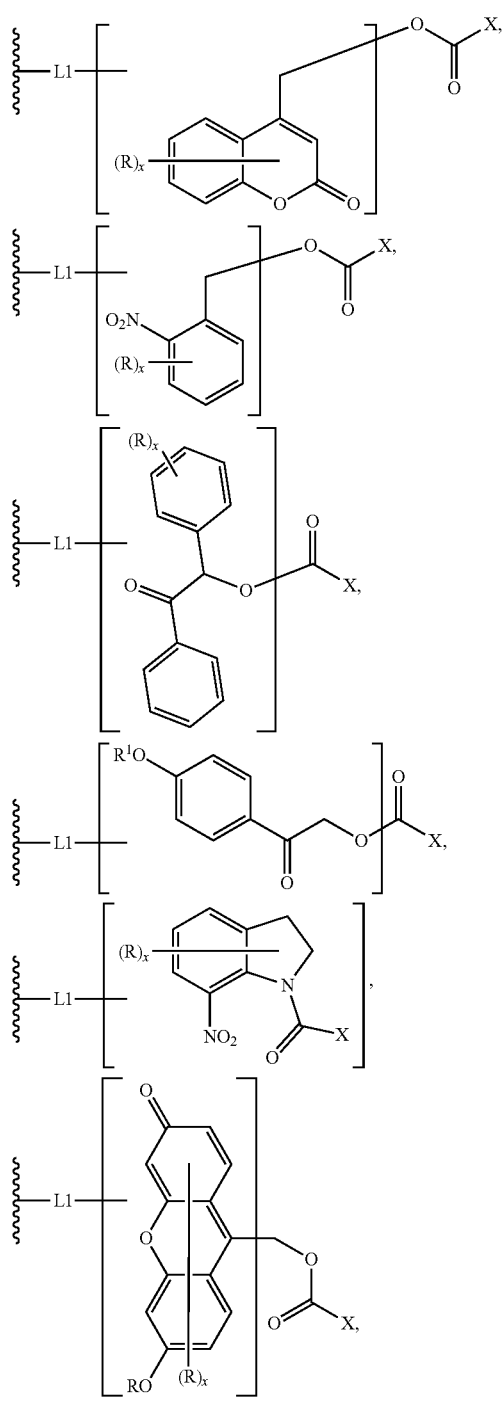

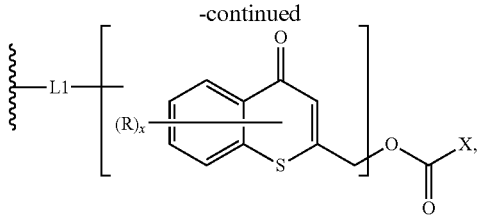

wherein L1 is an alkylene linker wherein one or more carbon atoms of the hydrocarbon chain are optionally replaced with —O—, —N(R$^a$)—, —C(=O)—, optionally substituted phenyl, or

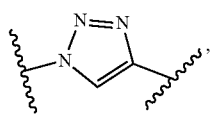

lp indicates the attachment to P;
R$^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;
R$^a$ is hydrogen, optionally substituted acyl, optionally substituted alkyl, optionally substituted alkenyl, optionally substituted alkynyl, or a nitrogen protecting group;
each instance of R is independently halogen, optionally substituted acyl, optionally substituted alkyl, optionally substituted heteroalkyl, optionally substituted alkenyl, optionally substituted alkynyl, optionally substituted carbocyclyl, optionally substituted heterocyclyl, optionally substituted aryl, optionally substituted heteroaryl, —OR$^{c1}$, —NO$^2$, —N(R$^{c2}$)$_2$, —SR$^{c1}$, or —CN;
R$^{c1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;
each instance of R$^{c2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of R$^{c2}$ are taken together with their intervening atoms to form a substituted or unsubstituted heterocyclic or substituted or unsubstituted heteroaryl ring; and
x is 0, 1, 2, 3, 4, 5, 6, or 7, as valency permits.

7. The composition of claim 6, wherein at least one instance of the moiety

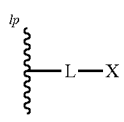

is of the formula:

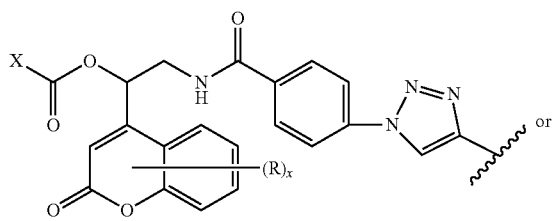

or

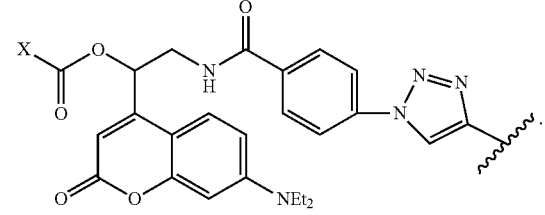

8. The composition of claim 6, wherein at least one instance of the moiety

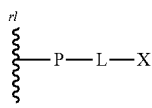

is of the formula:

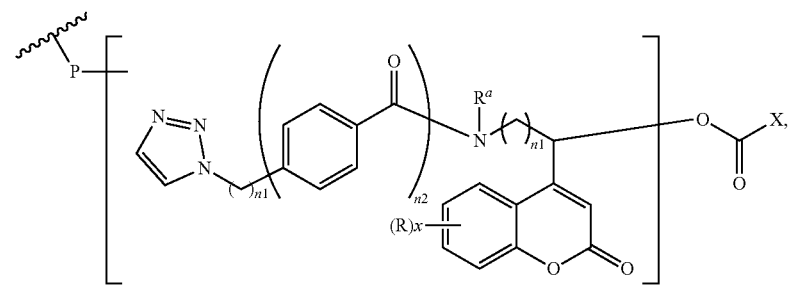

wherein:
 rl indicates the attachment to another instance of L;
 each instance of n1 is independently 0 or 1; and
 n2 is 0 or 1;

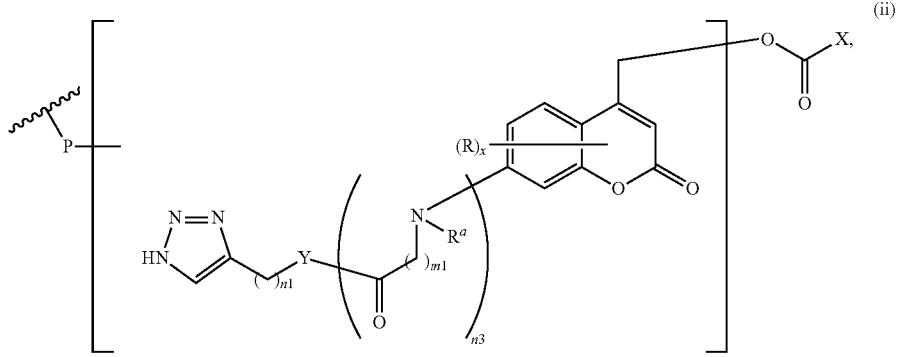

wherein:
 rl indicates the attachment to another instance of L;
 Y is —O— or —NR$^a$—;
 R$^a$ is hydrogen, optionally substituted acyl, or optionally substituted alkyl;
 m1 is 0 or 1;
 n1 is 0 or 1; and
 n3 is 0 or 1;

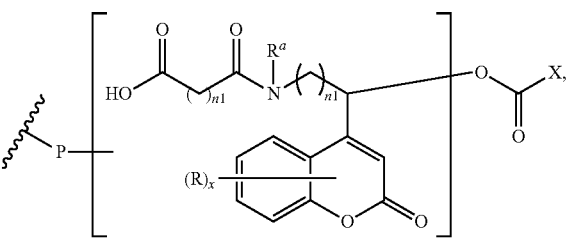

wherein:
 rl indicates the attachment to another instance of L;
 R$^a$ is hydrogen, optionally substituted acyl, or optionally substituted alkyl;

and n1 is 0, 1, or 2; or
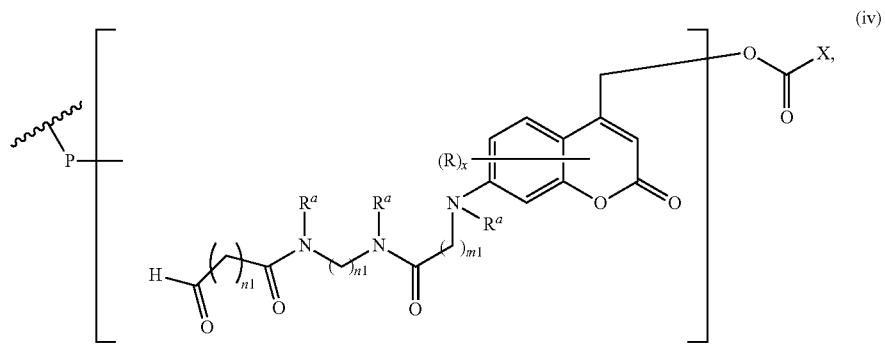
(iv)
wherein:
 r1 indicates the attachment to another instance of L;
 $R^a$ is hydrogen, optionally substituted acyl, or optionally substituted alkyl;
 m1 is 0 or 1; and
 n1 is 0, 1, or 2.
9. The composition of claim 6, wherein at least one instance of the moiety
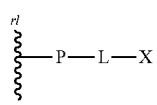
is of the formula:
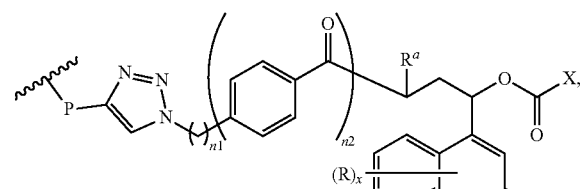
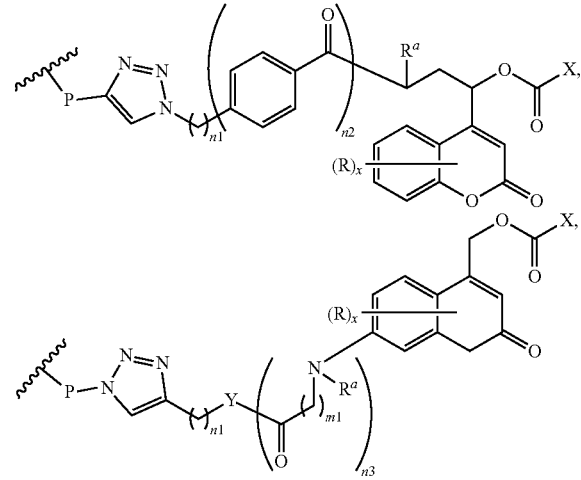
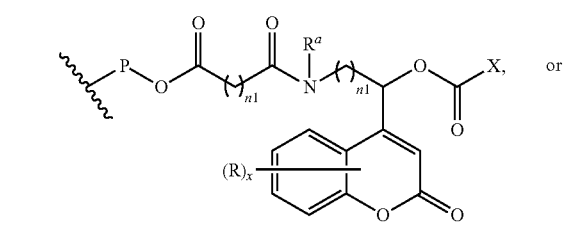
-continued
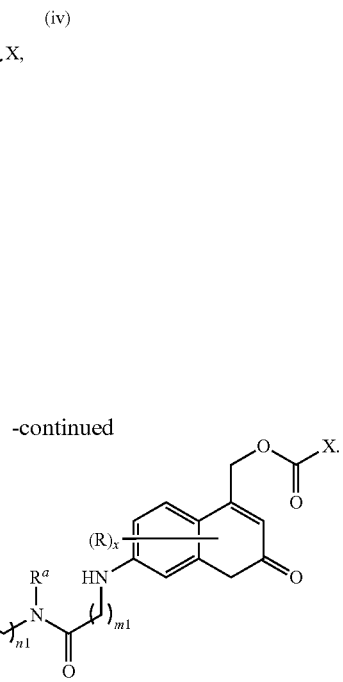
10. The composition of claim 6, wherein at least one instance of the moiety
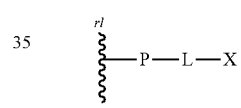
is of the formula:
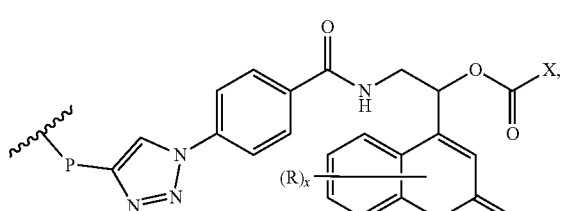
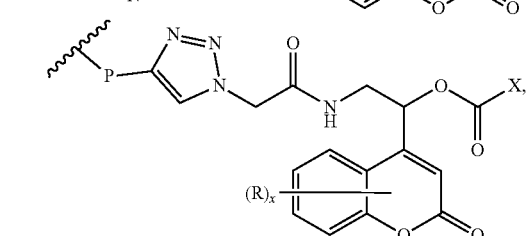
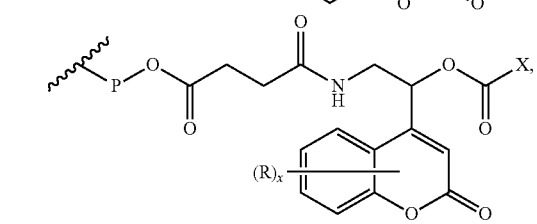

117
-continued

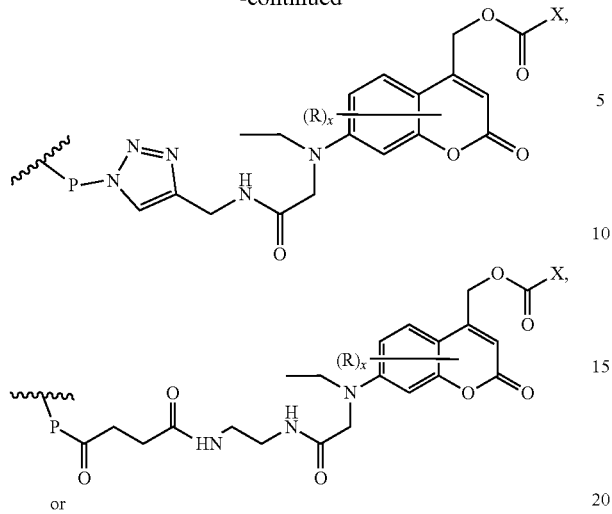

118
-continued

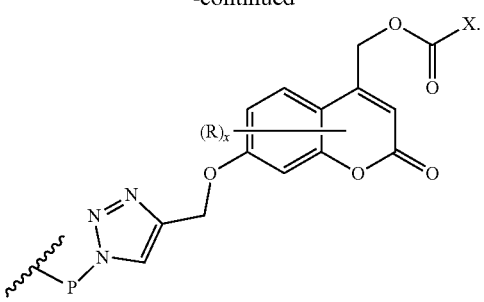

11. The composition of claim 6, wherein the compound of Formula (I) is of formula (I-a):

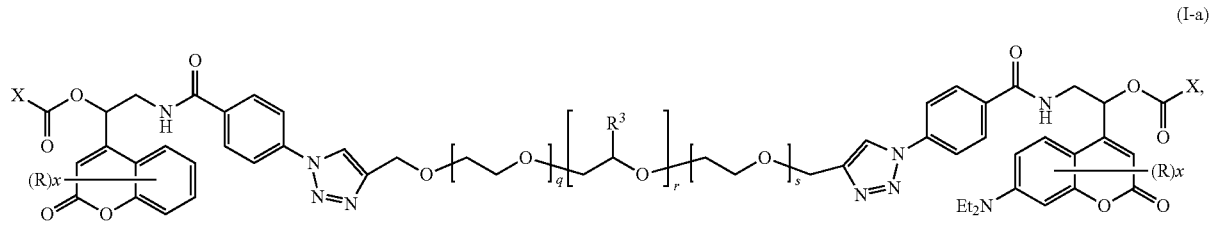

(I-a)

or a pharmaceutically acceptable salt, co-crystal, tautomer, stereoisomer, solvate, hydrate, polymorph, or an isotopically enriched derivative thereof, wherein:

each instance of $R^3$ is independently optionally substituted alkyl, optionally substituted alkenyl, optionally substituted alkynyl, optionally substituted aryl, optionally substituted heteryaryl, optionally substituted acyl, —$OR^b$, or —$N(R^b)_2$;

each instance of Rb is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two Rb taken together with the nitrogen to which they are attached form an optionally substituted heterocyclic or optionally substituted heteroaryl ring;

each of q, r, and s is independently an integer between 0 and 200; and the sum of q, r, and s is at least 1.

12. The composition of claim 6, wherein the compound of Formula (I) is of formula:

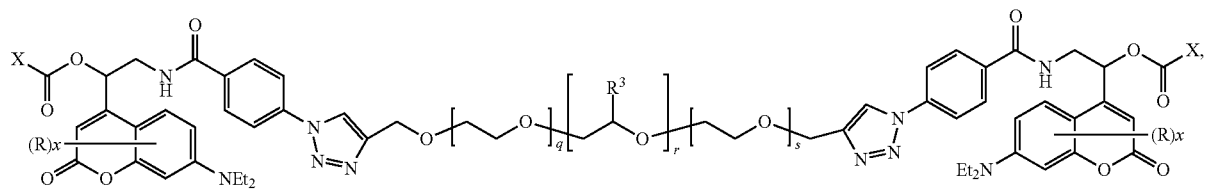
or
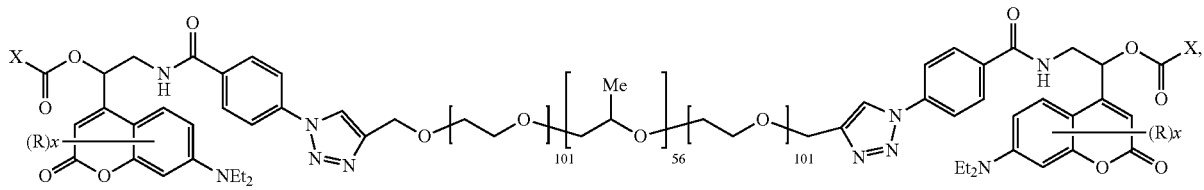
or a pharmaceutically acceptable salt, co-crystal, tautomer, stereoisomer, solvate, hydrate, polymorph, or an isotopically enriched derivative thereof.
13. The composition of claim 1, wherein the compound of Formula (I) is of formula:

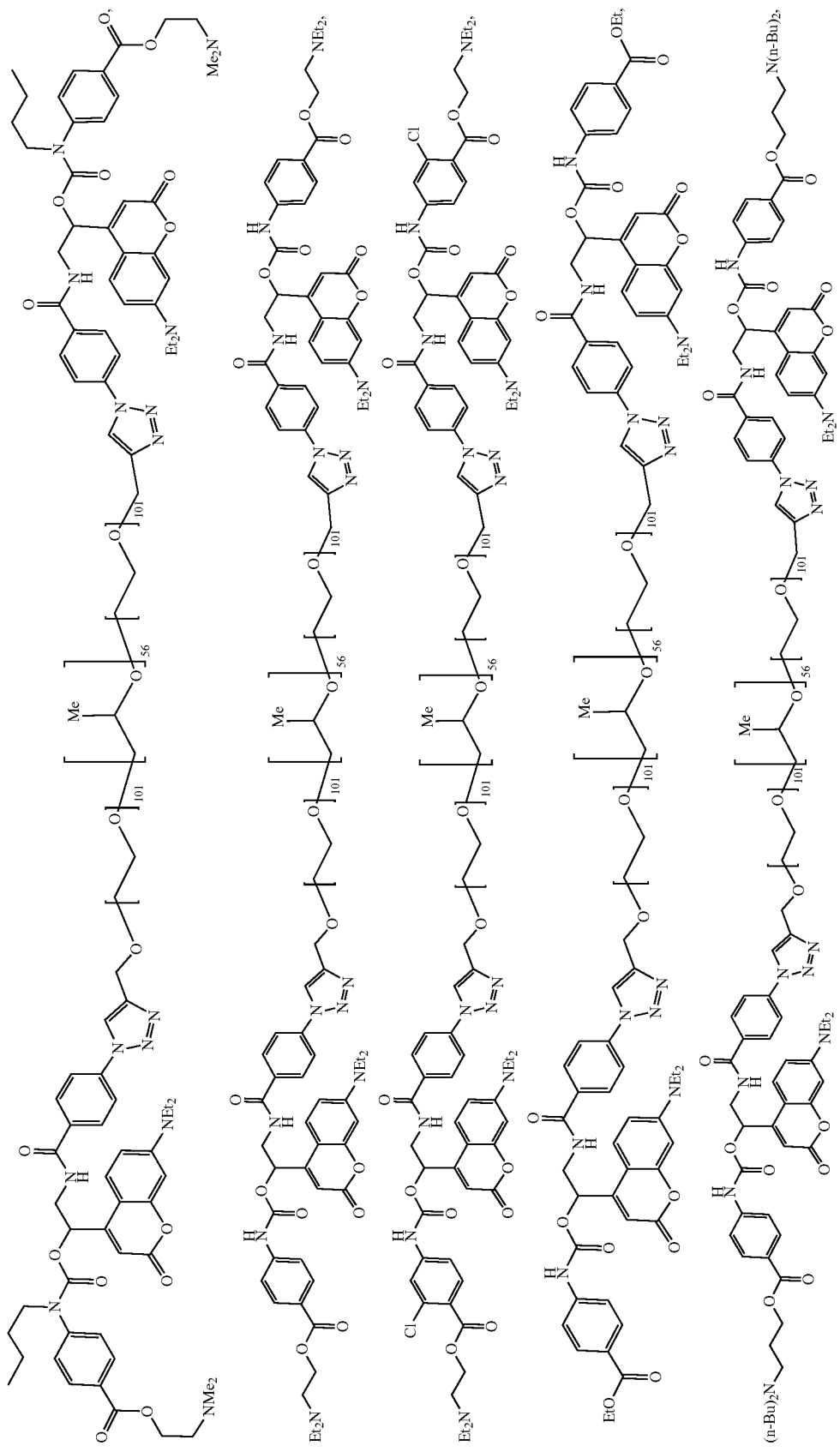

-continued
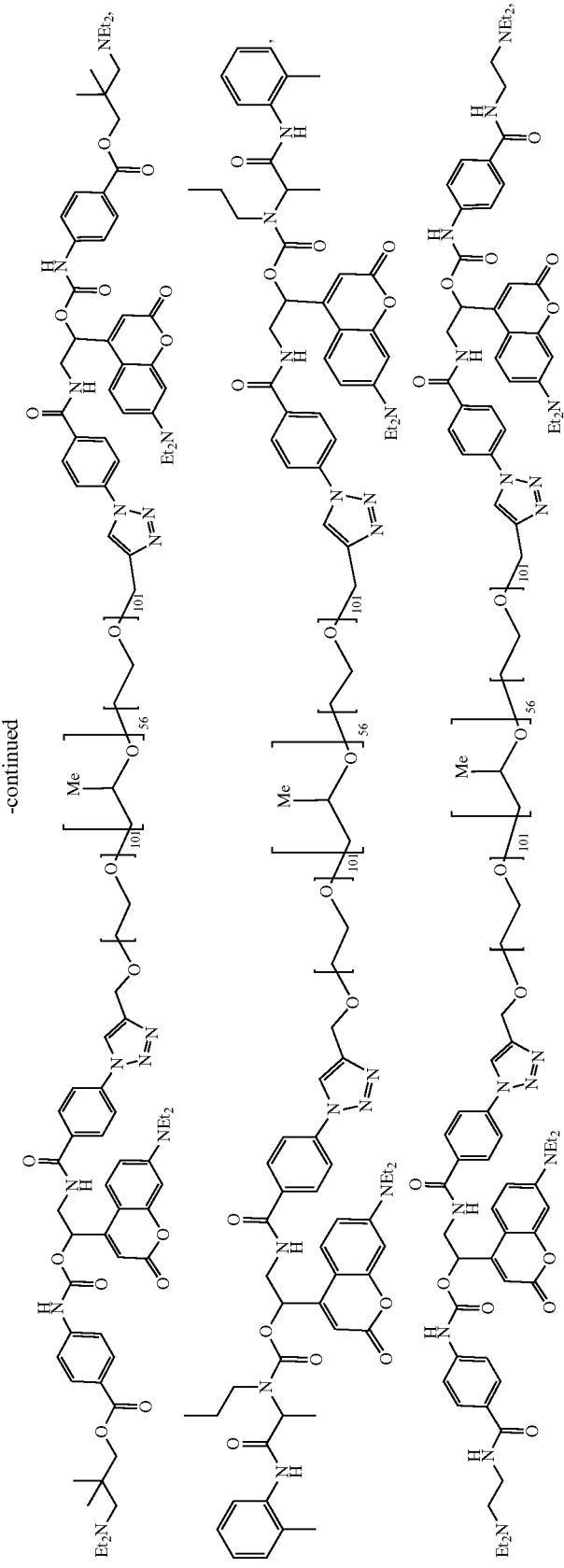

or a pharmaceutically acceptable salt, co-crystal, tautomer, stereoisomer, solvate, hydrate, polymorph, or an isotopically enriched derivative thereof.

14. A pharmaceutical composition comprising a composition of claim 1, and optionally a pharmaceutically acceptable excipient.

15. A method of treating pain in a subject in need thereof, the method comprising administering to the subject a therapeutically effective amount of a composition of claim 1.

16. A kit comprising a container and a composition of claim 1.

* * * * *